US012790589B2

(12) United States Patent
Bobisse et al.

(10) Patent No.: US 12,790,589 B2

(45) Date of Patent: Nov. 10, 2026

(54) METHOD FOR EXPANSION OF LYMPHOCYTES

(71) Applicant: LUDWIG INSTITUTE FOR CANCER RESEARCH LTD, Zurich (CH)

(72) Inventors: Sara Bobisse, Épalinges (CH); Alexandre Harari, Épalinges (CH); George Coukos, Épalinges (CH)

(73) Assignee: LUDWIG INSTITUTE FOR CANCER RESEARCH LTD, Zurich (CH)

( * ) Notice: Subject to any disclaimer, the term of this patent is extended or adjusted under 35 U.S.C. 154(b) by 641 days.

(21) Appl. No.: 16/761,711

(22) PCT Filed: Nov. 6, 2018

(86) PCT No.: PCT/EP2018/080343

§ 371 (c)(1),
(2) Date: May 5, 2020

(87) PCT Pub. No.: WO2019/086711

PCT Pub. Date: May 9, 2019

(65) Prior Publication Data

US 2020/0338125 A1 Oct. 29, 2020

Related U.S. Application Data

(60) Provisional application No. 62/582,163, filed on Nov. 6, 2017.

(51) Int. Cl.

*C12N 5/0781* (2010.01)
*A61K 40/11* (2025.01)
*A61K 40/42* (2025.01)
*C12N 5/0783* (2010.01)

(52) U.S. Cl.

CPC ............ *C12N 5/0635* (2013.01); *A61K 40/11* (2025.01); *A61K 40/4201* (2025.01); *C12N 5/0638* (2013.01); *C12N 2501/2302* (2013.01); *C12N 2501/2304* (2013.01); *C12N 2501/2321* (2013.01); *C12N 2501/515* (2013.01); *C12N 2501/52* (2013.01); *C12N 2502/1107* (2013.01)

(58) Field of Classification Search

CPC ..... A61K 35/17; C12N 5/0635; C12N 5/0638
See application file for complete search history.

(56) References Cited

U.S. PATENT DOCUMENTS

| | | | | |
|---|---|---|---|---|
| 8,287,857 | B2 | 10/2012 | Dudley et al. | |
| 2011/0052530 | A1* | 3/2011 | Dudley .............. | A61K 31/7076 424/85.2 |
| 2015/0017723 | A1 | 1/2015 | Rooney et al. | |
| 2017/0107490 | A1* | 4/2017 | Maeurer ............ | A61K 39/0011 |
| 2017/0160269 | A1 | 6/2017 | Linnemann et al. | |
| 2017/0218042 | A1 | 8/2017 | Tran et al. | |
| 2017/0224800 | A1* | 8/2017 | Tran ................... | A61K 40/4272 |
| 2017/0246277 | A1* | 8/2017 | Schneck ................ | C12N 13/00 |
| 2018/0127715 | A1 | 5/2018 | Veerapathran et al. | |
| 2019/0224236 | A1* | 7/2019 | Riddell .............. | A61K 39/4622 |

FOREIGN PATENT DOCUMENTS

| | | | |
|---|---|---|---|
| CN | 106574244 | | 4/2017 |
| JP | 2017-525754 | | 9/2017 |
| WO | 2011143656 | A2 | 11/2011 |
| WO | 2015189356 | | 12/2015 |
| WO | 2015189357 | | 12/2015 |
| WO | 2016145578 | A1 | 9/2016 |

OTHER PUBLICATIONS

Wu et al. "Adoptive T-cell therapy using autologous tumor-infiltrating lymphocytes for metastatic melanoma: current status and future outlook", Cancer J. Mar.-Apr. 2012;18(2):160-75. (Year: 2012).*

Tran et al. "Cancer immunotherapy based on mutation-specific CD4+ T cells in a patient with epithelial cancer", Science. May 9, 2014;344(6184):641-5. (Year: 2014).*

Ott et al. "An immunogenic personal neoantigen vaccine for patients with melanoma", Nature. Jul. 13, 2017;547(7662):217-221 (Year: 2017).*

Schultze et al. "CD40-activated human B cells: an alternative source of highly efficient antigen presenting cells to generate autologous antigen-specific T cells for adoptive immunotherapy", J Clin Invest. Dec. 1, 1997;100(11):2757-65 (Year: 1997).*

Friedman et al. "Augmented lymphocyte expansion from solid tumors with engineered cells for costimulatory enhancement", J Immunother. Nov.-Dec. 2011;34(9):651-61. (Year: 2011).*

Office Action issued Aug. 29, 2022 in connection with Japanese Application No. 2020-524540.

Shin C. et al., "Co-expression of CD40L with CD70 or OX40L increases B-cell viability and antitumor efficacy" Oncotarget, 2016, vol. 7, No. 29, p. 46173-46186.

Lee J. et al., "Activated B cells modified by electroporation of multiple mRNAs encoding immune stimulatory molecules are comparable to mature dendritic cells in inducing in vitro antigen-specific T-cell responses" Immunology, 2008, vol. 125, p. 229-240.

Communication (International Search Report) issued by the International Searching Authority in International Application No. PCT/EP2018/080343 dated Feb. 20, 2019, 5 pages total.

(Continued)

*Primary Examiner* — Peter Johansen

(74) *Attorney, Agent, or Firm* — Troutman Pepper Locke LLP

(57) ABSTRACT

The invention relates to a method for expanding antigen-specific lymphocytes by culturing samples from a subject containing lymphocytes or lymphocytes derived from the sample in the presence of one or more peptides comprising antigens and/or in the presence of an antigen presenting cell presenting antigens. Also disclosed is the use of such method for improving personalized immunotherapy (e.g., tumor immunotherapy).

15 Claims, 35 Drawing Sheets

Specification includes a Sequence Listing.

(56) References Cited

OTHER PUBLICATIONS

Communication (Written Opinion) issued by the International Searching Authority in International Application No. PCT/EP2018/080343 dated Feb. 20, 2019, 6 pages total.
Bobisse, S. et al., "Neoantigen-Based Cancer Immunotherapy" Annals of Translational Medicine (2016) vol. 4, No. 14, 9 pages total.
Ophir, E. et al., "Personalized Approaches to Active Immunotherapy in Cancer" Biochimica et Biophysica Acta (2016) vol. 1865, pp. 72-82.
Office Action issued Mar. 15, 2023 in connection with Canadian Application No. 3,081,479; 7 pages.
Arnaud M. et al., "Sensitive identification of neoantigens and cognate TCRs in human solid tumors" Nature Biotechnology, vol. 40, May 2022, pp. 656-660.
Chevalier, M.F. et al., "High-Throughput Monitoring of Human Tumor-Specific T-Cell Responses with Large Peptide Pools" Oncoimmunology (2015) vol. 4, Issue. 10, 8 pages total.
Bobisse, S. et al. Sensitive and frequent identification of high avidity neo-epitope specific CD8+ T cells in immunotherapy-naive ovarian cancer. Nat. Commun. 9, 1092 (2018).
Harari A. et al., "An HIV-1 clade C DNA prime, NYVAC boost vaccine regimen induces reliable, polyfunctional, and long-lasting T cell responses", JEM, vol. 205, No. 1, Jan. 21, 2008, pp. 63-77.
Office Action issued Jun. 18, 2024 in connection with Canadian Application No. 3,081,479.
Ye, Q et al., "Engineered artificial antigen presenting cells facilitate direct and efficient expansion of tumor infiltrating lymphocytes", J Transl Med., 9, p. 131, Aug. 9, 2011 (Sep. 8, 2011).
Kim et al., The ABCs of artificial antigen presentation, Nature Biotechnology (Apr. 2004), 22(4):403-410.

* cited by examiner

FIG. 7

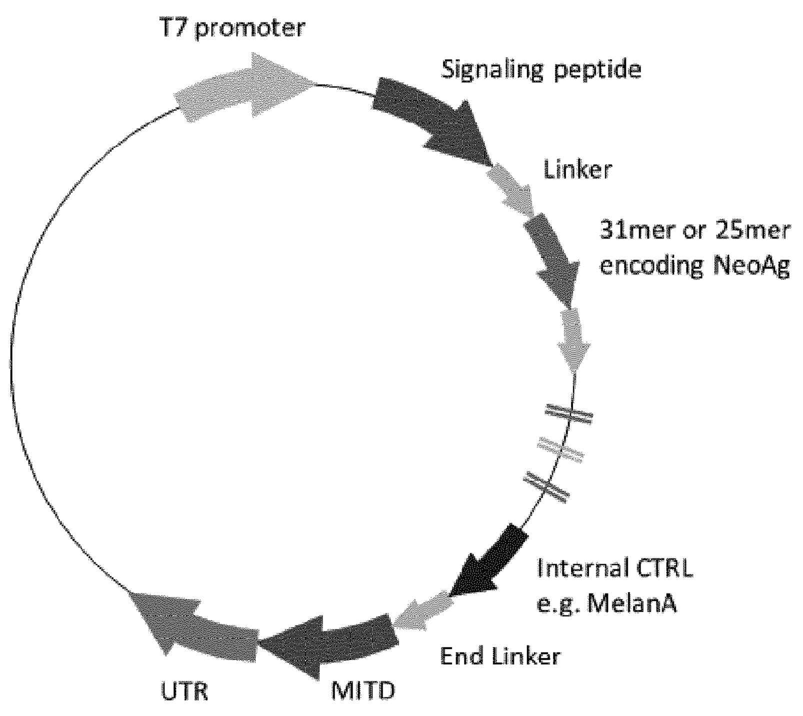

Signaling peptide: MRVTAPRTLILLLSGALALTETWAGS

Linkers (peptide): GGSGGGGSGG

End Linker (peptide): GGSLGGGGSG

MITD (MHC-I trafficking signal peptide):
IVGIVAGLAVLAVVVIGAVVATVMCRRKSSGGKGGSYSQAASSDSAQGSDVSL
TA UTR (nucleotide sequence):
GCTCGCTTTCTTGCTGTCCAATTTCTATTAAAGGTTCCTTTGTTCCCTAAGTC
CAACTACTAAACTGGGGGATATTATGAAGGGCCTTGAGCATCTGGATTCTGC
CTAATAAAAAACATTTATTTTCATTG (X2)

FIG. 12
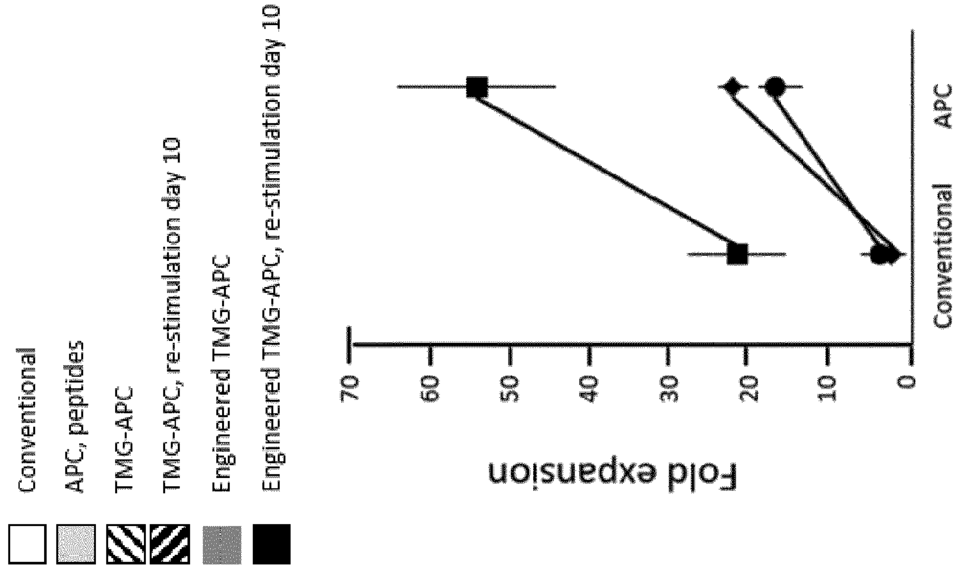
FIG. 13

Fig. 14 cont.
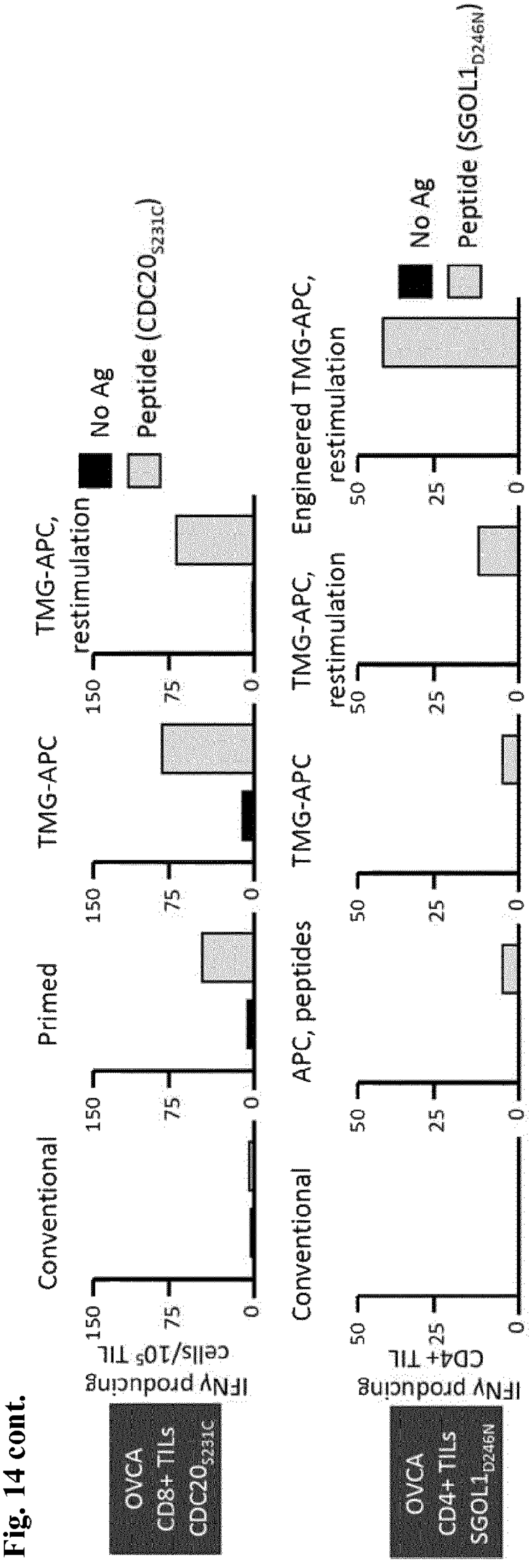
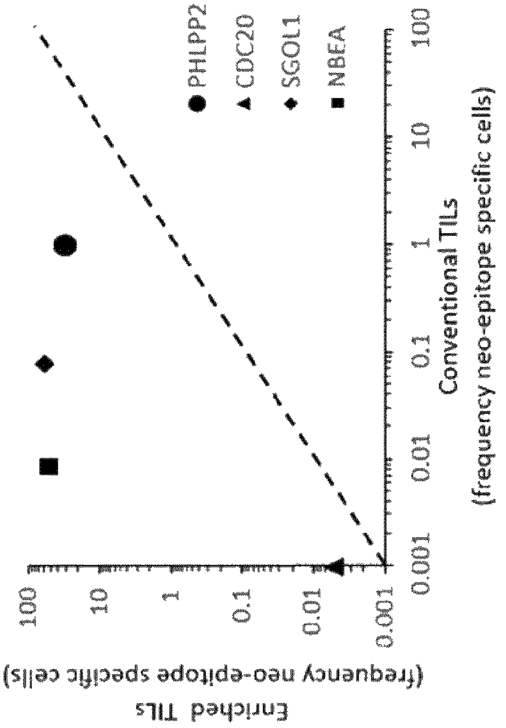
FIG. 15

FIG. 17

Non-Limiting Example of a Tandem Minigene

Nucleotide sequence that will be translated and processed upon introduction into APC:

ATGAGAGTGACAGCCCCTAGAACACTGATCCTGCTGCTGTCTGGTGCCCTGGCT
CTGACAGAAACATGGGCTGGAAGCTCTAGAGGAGGATCTGGCGGAGGTGGTAG
TGGCGGATCTGAATTTCAGGCCGCTCTGTCCAGAAAGGTGGCCGAGCTGGTGC
ACTTTCTGCTGCTGAAGTACCGGGCCAGAGAACCCGTGACAAAAGCTGGTGGT
TCTGGCGGTGGCGGTAGCGGAGGAACATACGTGCTGAGCATTGTGCCTAGCGG
CCCTCTGAAGGCCGAGATTGCTCAGAGACTGGAAGATGTGTTCGCCGGCAAGA
ACACCGATCTCGGAGGCAGCGGCGGAGGCGGCTCTGGTGGAAAAACAAGACCC
ATTCTGAGCCCTCTGACCAAGGGCATCCTGGGCTTCGTGTTCACCCTGACAGTG
CCATCTGAGAGAGGCCTGCAGAGAAGAGGTGGCAGCGGAGGCGGTGGATCAGG
CGGAAAAGGACACGGCCACAGCTACACCACAGCCGAAGAAGCCGCCGGAATCG
GAATCCTGACCGTGATTCTGGGAGTGCTGCTGCTCATCGGCTGTTGGGGCGGA
AGTGGTGGCGGTGGAAGCGGCGGAAACAAGATCACATATGGCGCCTGTCCTAA
ATACGTGAAGCAGAACACCCTGAAGCTGGCCACCGGCATGAGAAACGTGCCAG
AGAAACAGACAGGCGGCAGCCTTGGAGGCGGAGGTAGTGGAATCGTGGGAATT
GTGGCTGGCCTGGCTGTGCTGGCCGTGGTGGTTATTGGAGCTGTGGTGGCCACA
GTGATGTGCAGAAGAAAGTCCAGCGGCGGCAAAGGCGGAAGCTATTCTCAGGC
CGCCAGCAGCGATTCTGCCCAGGGATCTGATGTGTCCCTGACCGCT

Corresponding amino-acid sequence:

MRVTAPRTLILLLSGALALTETWAGSSRGGSGGGGSGGSEFQAALSRKVAELVH
FLLLKYRAREPVTKAGGSGGGGSGGTYVLSIVPSGPLKAEIAQRLEDVFAGKNTD
LGGSGGGGSGGKTRPILSPLTKGILGFVFTLTVPSERGLQRRGGSGGGGSGGKGH
GHSYTTAEEAAGIGILTVILGVLLLIGCWGGSGGGGSGGNKITYGACPKYVKQNTL
KLATGMRNVPEKQTGGSLGGGGSGIVGIVAGLAVLAVVVIGAVVATVMCRRKSS
GGKGGSYSQAASSDSAQGSDVSLTA

FIG. 18

Non-Limiting Example of a Tandem Minigene (CTE-006)

Nucleotide sequence that will be translated and processed upon introduction into APC:

ATGAGAGTGACAGCCCCTCGGACACTGATCCTGCTGCTTTCTGGTGCCCTGGCT
CTGACAGAAACATGGGCTGGAAGCTCTAGAGGAGGATCTGGCGGAGGTGGAAG
TGGCGGAGAAAGACCCGTGCGGTACATCAGAAAGCCCATCGACTACACCATCG
TGGACGACATCGGACACGGCGTGAAGTGGCTGCTGAGATTCAAAGTTGGCGGC
TCTGGTGGCGGAGGCAGCGGAGGAATTCTGCAGCTGCTGCAAATGGAACAGCC
CGGCGAGTACATCTCCTGCGTGGCCTGGATCAAAGAGGGCAACTATCTGGCCGT
GGGCACATCAGGCGGTAGCGGCGGAGGCGGCTCAGGCGGAGGACCTTTGCCTA
GAGAAGGTTCTGGCGGCAGCACCAGCGATTACCTGAGCCAGAGCTACAGCTAC
AGCAGCATCCTGAACAAGAGCGAGACAGGCGGAAGCGGAGGCGGAGGAAGCGG
TGGAAGATTCAGACCCGACTTCAAGCGGAAGTTCGCCGACTTCTTCGAGATGG
ACACCATCAGCGAGTATATCTACCACTGCAACGCCCAGAATCCTGGCGGATCAG
GTGGTGGTGGCTCCGGTGGATGGTGGGTTACAGTTCAGCCTCCTGCCAGAAGA
ATGGGCTGGCTGTCTCTGCTGCTGCTCCTGACACAGTGTCTGGGAGTGCCAGGA
CAGAGAGGCGGATCTCTTGGAGGTGGCGGATCTGGCATCGTGGGAATTGTGGC
TGGACTGGCTGTGCTGGCAGTGGTGGTTATTGGAGCCGTGGTGGCCACAGTGA
TGTGCAGAAGAAAGAGCAGCGGCGGCAAAGGCGGCAGCTATTCTCAGGCCGCC
TCTAGCGATTCTGCCCAGGGCTCTGATGTGTCTCTGACAGCT

Corresponding amino-acid sequence:

MRVTAPRTLILLLSGALALTETWAGSSRGGSGGGGSGGERPVRYIRKPIDYTIVD
DIGHGVKWLLRFKVGGSGGGGSGGILQLLQMEQPGEYISCVAWIKEGNYLAVGT
SGGSGGGGSGGGPLPREGSGGSTSDYLSQSYSYSSILNKSETGGSGGGGSGGRFRP
DFKRKFADFFEMDTISEYIYHCNAQNPGGSGGGGSGGWWVTVQPPARRMGWL
SLLLLLTQCLGVPGQRGGSLGGGGSGIVGIVAGLAVLAVVVIGAVVATVMCRRKS
SGGKGGSYSQAASSDSAQGSDVSLTA

FIG. 19

Non-Limiting Example of a Tandem Minigene (CTE-007)

Nucleotide sequence that will be translated and processed upon introduction into APC:

ATGAGAGTGACAGCCCCTCGGACACTGATCCTGCTGCTTTCTGGTGCCCTGGCT
CTGACAGAAACATGGGCTGGAAGCTCTAGAGGAGGATCTGGCGGAGGTGGAAG
TGGCGGAGCTGCTAAACAGCTGACACCTGAAGTTCGGGCCCTGCTGACCCAGTA
TGAGACAGGCGGTTCTGGTGGCGGAGGCAGCGGAGGCGGAGGATTTGTTCTGG
GACTGCTGTTTCTCGGAGCCGGCCTGTTCCTGTACTTCCGGAATCAGAAGGGCC
ACAGCGGCCTGCAACCTACTGGCGGTGGCTCAGGTGGTGGTGGTTCTGGCGGA
ACCGATCTGTGCTTCCTGAACAGCCCCATCTTCAAGCAGAAGAAGAACCTGCGG
CGGAGCAAGAAAAGAGCCCTGGAAGTCTCTCCTGCCAAAGGCGGTAGTGGTGG
TGGCGGATCAGGCGGAGAAGATGCCGATGAACCTGGCAGAGTGCCCACCGAGG
ACTACATGATCCACATCATCGAGAAGTGGGGCGGTAGTGGCGGCGGAGGAAGC
GGTGGACTTGAAAAATCTGCCGTGCTGCAAGAGGCCCGGATCTTCAACGAGAT
CCCCATCAATCCCAGACGGTGCCTGCACATCCTGACCAAGATTCTCGGCGGCTC
TCTTGGAGGTGGCGGCTCTGGTATTGTGGGAATTGTGGCTGGACTGGCCGTGC
TGGCTGTGGTGGTTATTGGAGCAGTGGTGGCCACAGTGATGTGCAGAAGAAAG
AGCAGCGGCGGCAAAGGCGGCAGCTATTCTCAGGCCGCTAGCAGCGATTCTGCC
CAGGGATCTGATGTGTCTCTGACCGCT

Corresponding amino-acid sequence:

MRVTAPRTLILLLSGALALTETWAGSSRGGSGGGGSGGAAKQLTPEVRALLTQY
ETGGSGGGGSGGGGFVLGLLFLGAGLFLYFRNQKGHSGLQPTGGGSGGGGSGGT
DLCFLNSPIFKQKKNLRRSKKRALEVSPAKGGSGGGGSGGEDADEPGRVPTEDY
MIHIIEKWGGSGGGGSGGLEKSAVLQEARIFNEIPINPRRCLHILTKILGGSLGGGG
SGIVGIVAGLAVLAVVVIGAVVATVMCRRKSSGGKGGSYSQAASSDSAQGSDVSL
TA

FIG. 20

Non-Limiting Example of a Tandem Minigene (CrCp5)

Nucleotide sequence that will be translated and processed upon introduction into APC:

ATGAGAGTGACAGCCCCTCGGACACTGATCCTGCTGCTTTCTGGTGCCCTGGCT
CTGACAGAAACATGGGCTGGAAGCTCTAGAGGAGGATCTGGCGGAGGTGGAAG
TGGCGGAGCTGCTAAACAGCTGACACCTGAAGTTCGGGCCCTGCTGACCCAGTA
TGAGACAGGCGGTTCTGGTGGCGGAGGCAGCGGAGGCGGAGGATTTGTTCTGG
GACTGCTGTTTCTCGGAGCCGGCCTGTTCCTGTACTTCCGGAATCAGAAGGGCC
ACAGCGGCCTGCAACCTACTGGCGGTGGCTCAGGTGGTGGTGGTTCTGGCGGA
ACCGATCTGTGCTTCCTGAACAGCCCCATCTTCAAGCAGAAGAACCTGCGG
CGGAGCAAGAAAAGAGCCCTGGAAGTCTCTCCTGCCAAAGGCGGTAGTGGTGG
TGGCGGATCAGGCGGAGAAGATGCCGATGAACCTGGCAGAGTGCCCACCGAGG
ACTACATGATCCACATCATCGAGAAGTGGGGCGGTAGTGGCGGCGGAGGAAGC
GGTGGACTTGAAAAATCTGCCGTGCTGCAAGAGGCCCGGATCTTCAACGAGAT
CCCCATCAATCCCAGACGGTGCCTGCACATCCTGACCAAGATTCTCGGCGGCTC
TCTTGGAGGTGGCGGCTCTGGTATTGTGGGAATTGTGGCTGGACTGGCCGTGC
TGGCTGTGGTGGTTATTGGAGCAGTGGTGGCCACAGTGATGTGCAGAAGAAAG
AGCAGCGGCGGCAAAGGCGGCAGCTATTCTCAGGCCGCTAGCAGCGATTCTGCC
CAGGGATCTGATGTGTCTCTGACCGCT

Corresponding amino-acid sequence:

MRVTAPRTLILLLSGALALTETWAGSSRGGSGGGGSGGAAKQLTPEVRALLTQY
ETGGSGGGGSGGGGFVLGLLFLGAGLFLYFRNQKGHSGLQPTGGGSGGGGSGGT
DLCFLNSPIFKQKKNLRRSKKRALEVSPAKGGSGGGGSGGEDADEPGRVPTEDY
MIHIIEKWGGSGGGGSGGLEKSAVLQEARIFNEIPINPRRCLHILTKILGGSLGGGG
SGIVGIVAGLAVLAVVVIGAVVATVMCRRKSSGGKGGSYSQAASSDSAQGSDVSL
TA

FIG. 21 pMA-RQ-hIL12-AB
CTAAATTGTAAGCGTTAATATTTTGTTAAAATTCGCGTTAAATTTTTGTTAAA
TCAGCTCATTTTTTAACCAATAGGCCGAAATCGGCAAAATCCCTTATAAATCA
AAAGAATAGACCGAGATAGGGTTGAGTGGCCGCTACAGGGCGCTCCCATTCGC
CATTCAGGCTGCGCAACTGTTGGGAAGGGCGTTTCGGTGCGGGCCTCTTCGCTA
TTACGCCAGCTGGCGAAAGGGGGATGTGCTGCAAGGCGATTAAGTTGGGTAAC
GCCAGGGTTTTCCCAGTCACGACGTTGTAAAACGACGGCCAGTGAGCGCGACGT
AATACGACTCACTATAGGGCGAATTGAAGGAAGGCCGTCAAGGCCGCATCGGA
TCCGCTAGCGCCACCATGTGGCCTCCTGGATCTGCTTCTCAGCCTCCTCCATCT
CCTGCCGCTGCTACAGGACTTCATCCTGCCGCAAGACCCGTGTCTCTGCAGTGC
AGACTGAGCATGTGCCCCGCCAGATCTCTGCTGCTGGTGGCTACACTGGTGCTG
CTGGATCATCTGAGCCTGGCCAGAAACCTGCCAGTGGCCACGCCTGATCCTGGC
ATGTTTCCTTGTCTGCACCACAGCCAGAACCTGCTGAGAGCCGTGTCCAACATG
CTGCAGAAGGCCAGACAGACCCTGGAATTCTACCCCTGCACCAGCGAGGAAATC
GACCACGAGGACATCACCAAGGACAAGACCAGCACCGTGGAAGCCTGCCTGCCT
CTGGAACTGACCAAGAACGAGAGCTGCCTGAACAGCAGAGAGACATCCTTCAT
CACCAACGGCTCTTGCCTGGCCTCCAGAAAGACCTCCTTCATGATGGCCCTGTG
CCTGAGCAGCATCTACGAGGACCTGAAGATGTACCAGGTGGAATTCAAGACCA
TGAACGCCAAGCTGCTGATGGACCCCAAGCGGCAGATCTTCCTGGACCAGAATA
TGCTGGCCGTGATCGACGAGCTGATGCAGGCCCTGAACTTCAACAGCGAGACA
GTGCCCCAGAAGTCCAGCCTGGAAGAACCCGACTTCTACAAGACCAAGATCAA
GCTGTGCATCCTGCTGCACGCCTTCCGGATCAGAGCCGTGACCATCGACAGAGT
GATGAGCTACCTGAACGCCAGCCCGCGGGCCACGAACTTCTCTCTGTTAAAGCA
AGCAGGAGACGTGGAAGAAAACCCCGGTCCTGCTAGCGCCACCATGTGTCACCA
GCAGCTGGTCATCAGCTGGTTCAGCCTGGTGTTCCTGGCCTCTCCTCTGGTGGC
CATCTGGGAGCTGAAGAAAGACGTGTACGTGGTGGAACTGGACTGGTATCCCG
ATGCTCCTGGCGAGATGGTGGTGCTGACCTGCGATACCCCTGAAGAGGACGGC
ATCACCTGGACACTGGATCAGTCTAGCGAGGTGCTCGGCAGCGGCAAGACCCTG
ACCATCCAAGTGAAAGAGTTTGGCGACGCCGGCCAGTACACCTGTCACAAAGG
CGGAGAAGTGCTGAGCCACAGCCTGCTGCTGCTCCACAAGAAAGAGGATGGCA
TTTGGAGCACCGACATCCTGAAGGACCAGAAAGAGCCCAAGAACAAGACCTTC
CTGAGATGCGAGGCCAAGAACTACAGCGGCCGGTTCACATGTTGGTGGCTGAC
CACCATCAGCACCGACCTGACCTTCAGCGTGAAGTCCAGCAGAGGCAGCAGTGA
TCCTCAGGGCGTTACATGTGGCGCCGCTACACTGTCTGCCGAAAGAGTGCGGGG
CGACAACAAAGAATACGAGTACAGCGTGGAATGCCAAGAGGACAGCGCCTGTC
CAGCCGCCGAAGAGTCTCTGCCTATCGAAGTGATGGTGGACGCCGTGCACAAGC
TGAAGTACGAGAACTACACCTCCAGCTTTTTCATCCGGGACATCATCAAGCCCG
ATCCTCCAAAGAACCTGCAGCTGAAGCCTCTGAAGAACAGCAGACAGGTGGAA
GTGTCCTGGGAGTACCCCGACACCTGGTCTACACCCCACAGCTACTTCAGCCTG

FIG. 21 cont.

ACCTTTTGCGTGCAAGTGCAGGGCAAGTCCAAGCGCGAGAAAAAGGACCGGGT
GTTCACCGACAAGACCAGCGCCACCGTGATCTGCAGAAAGAACGCCAGCATCAG
CGTCAGAGCCCAGGACCGGTACTACAGCAGCTCTTGGAGCGAATGGGCCAGCGT
GCCATGTTCTCCGCGGCTCGAGTAGTCTAGAGCTGGGCCTCATGGGCCTTCCTT
TCACTGCCCGCTTTCCAGTCGGGAAACCTGTCGTGCCAGCTGCATTAACATGGT
CATAGCTGTTTCCTTGCGTATTGGGCGCTCTCCGCTTCCTCGCTCACTGACTCG
CTGCGCTCGGTCGTTCGGGTAAAGCCTGGGGTGCCTAATGAGCAAAAGGCCAG
CAAAAGGCCAGGAACCGTAAAAAGGCCGCGTTGCTGGCGTTTTTCCATAGGCT
CCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTA
TCGCCACTGGCAGCAGCCACTGGTAACAGGATTAGCAGAGCGAGGTATGTAGG
CGGTGCTACAGAGTTCTTGAAGTGGTGGCCTAACTACGGCTACACTAGAAGAA
CAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTGAT
CTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAA
TGAAGTTTTAAATCAATCTAAAGTATATATGAGTAAACTTGGTCTGACAGTTA
TTAGAAAAATTCATCCAGCAGACGATAAAACGCAATACGCTGGCTATCCGGTG
CCGCAATGCCATACAGCACCAGAAAACGATCCGCCCATTCGCCGCCCAGTTCTT
CCGCAATATCACGGGTGGCCAGCGCAATATCCTGATAACGATCCGCCACGCCCA
GACGGCCGCAATCAATAAAGCCGCTAAAACGGCCATTTTCCACCATAATGTTCG
GCAGGCACGCATCACCATGGGTCACCACCAGATCTTCGCCATCCGGCATGCTCG
CTTTCAGACGCGCAAACAGCTCTGCCGGTGCCAGGCCCTGATGTTCTTCATCCA
GATCATCCTGATCCACCAGGCCCGCTTCCATACGGGTACGCGCACGTTCAATAC
GATGTTTCGCCTGATGATCAAACGGACAGGTCGCCGGGTCCAGGGTATGCAGA
CGACGCATGGCATCCGCCATAATGCTCACTTTTTCTGCCGGCGCCAGATGGCTA
GACAGCAGATCCTGACCCGGCACTTCGCCCAGCAGCAGCCAATCACGGCCCGCT
TCGGTCACCACATCCAGCACCGCCGCACACGGAACACCGGTGGTGGCCAGCCAG
CTCAGACGCGCCGCTTCATCCTGCAGCTCGTTCAGCGCACCGCTCAGATCGGTT
TTCACAAACAGCACCGGACGACCCTGCGCGCTCAGACGAAACACCGCCGCATCA
GAGCAGCCAATGGTCTGCTGCGCCCAATCATAGCCAAACAGACGTTCCACCCAC
GCTGCCGGGCTACCCGCATGCAGGCCATCCTGTTCAATCATACTCTTCCTTTTT
CAATATTATTGAAGCATTTATCAGGGTTATTGTCTCATGAGCGGATACATATT
TGAATGTATTTAGAAAAATAAACAAATAGGGGTTCCGCGCACATTTCCCCGAA
AAGTGCCAC

FIG. 22

>pcDNA6-hOX40L (5657 bp)
GACGGATCGGGAGATCTCCCGATCCCCTATGGTGCACTCTCAGTACAATCTGCT
CTGATGCCGCATAGTTAAGCCAGTATCTGCTCCCTGCTTGTGTGTTGGAGGTCG
CTGAGTAGTGCGCGAGCAAAATTTAAGCTACAACAAGGCAAGGCTTGACCGAC
AATTGCATGAAGAATCTGCTTAGGGTTAGGCGTTTTGCGCTGCTTCGCGATGT
ACGGGCCAGATATACGCGTTGACATTGATTATTGACTAGTTATTAATAGTAAT
CAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACG
TCAATAATGACGTATGTTCCCATAGTAACGCCAATAGGGACTTTCCATTGACG
TCAATGGGTGGAGTATTTACGGTAAACTGCCCACTTGGCAGTACATCAAGTGT
ATCATATGCCAAGTACGCCCCCTATTGACGTCAATGACGGTAAATGGCCCGCCT
GGCATTATGCCCAGTACATGACCTTATGGGACTTTCCTACTTGGCAGTACATCT
ACGTATTAGTCATCGCTATTACCATGGTGATGCGGTTTTGGCAGTACATCAAT
GGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCG
TAACAACTCCGCCCCATTGACGCAAATGGGCGGTAGGCGTGTACGGTGGGAGG
TCTATATAAGCAGAGCTCTCTGGCTAACTAGAGAACCCACTGCTTACTGGCTTA
TCGAAATTAATACGACTCACTATAGGGAGACCCAAGCTGGCTAGTTAAGCTTG
GTACCGAGCTCGGATCTATGGAAAGGGTCCAACCCCTGGAAGAGAATGTGGGA
AATGCAGCCAGGCCAAGATTCGAGAGGAACAAGCTATTGCTGGTGGCCTCTGT
AATTCAGGGACTGGGGCTGCTCCTGTGCTTCACCTACATCTGCCTGCACTTCTC
TGCTCTTCAGGTATCACATCGGTATCCTCGAATTCAAAGTATCAAAGTACAAT
TTACCGAATATAAGAAGGAGAAAGGTTTCATCCTCACTTCCCAAAAGGAGGAT
GAAATCATGAAGGTGCAGAACAACTCAGTCATCATCAACTGTGATGGGTTTTA
TCTCATCTCCCTGAAGGGCTACTTCTCCCAGGAAGTCAACATTAGCCTTCATTA
CCAGAAGGATGAGGAGCCCCTCTTCCAACTGAAGAAGGTCAGGTCTGTCAACT
CCTTGATGGTGGCCTCTCTGACTTACAAAGACAAAGTCTACTTGAATGTGACC
ACTGACAATACCTCCCTGGATGACTTCCATGTGAATGGCGGAGAACTGATTCT
TATCCATCAAAATCCTGGTGAATTCTGTGTCCTTTGAGAATTCTGCAGATATCC
AGCACAGTGGCGGCCGCTCGAGGTCACCCATTCGAACAAAAACTCATCTCAGAA
GAGGATCTGAATATGCATACCGGTCATCATCACCATCACCATTGAGTTTAAAC
CCGCTGATCAGCCTCGACTGTGCCTTCTAGTTGCCAGCCATCTGTTGTTTGCCC
CTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGG
GGGGTGGGGTGGGGCAGGACAGCAAGGGGGAGGATTGGGAAGACAATAGCAGG
CATGCTGGGGATGCGGTGGGCTCTATGGCTTCTGAGGCGGAAAGAACCAGCTG
GGGCTCTAGGGGGTATCCCCACGCGCCCTGTAGCGGCGCATTAAGCGCGGCGGG
TGTGGTGGTTACGCGCAGCGTGACCGCTACACTTGCCAGCGCCCTAGCGCCCGC

FIG. 22 cont.

TCCTTTCGCTTTCTTCCCTTCCTTTCTCGCCACGTTCGCCGGCTTTCCCCGTCAA
GCTCTAAATCGGGGGCTCCCTTTAGGGTTCCGATTTAGTGCTTTACGGCACCTC
GACCCCAAAAAACTTGATTAGGGTGATGGTTCACGTAGTGGGCCATCGCCCTG
ATAGACGGTTTTTCGCCCTTTGACGTTGGAGTCCACGTTCTTTAATAGTGGACT
CTTGTTCCAAACTGGAACAACACTCAACCCTATCTCGGTCTATTCTTTTGATTT
ATAAGGGATTTTGCCGATTTCGGCCTATTGGTTAAAAAATGAGCTGATTTAAC
AAAAATTTAACGCGAATTAATTCTGTGGAATGTGTGTCAGTTAGGGTGTGGAA
AGTCCCCAGGCTCCCCAGCAGGCAGAAGTATGCAAAGCATGCATCTCAATTAGT
CAGCAACCAGGTGTGGAAAGTCCCCAGGCTCCCCAGCAGGCAGAAGTATGCAA
AGCATGCATCTCAATTAGTCAGCAACCATAGTCCCGCCCCTAACTCCGCCCATC
CCGCCCCTAACTCCGCCCAGTTCCGCCCATTCTCCGCCCCATGGCTGACTAATTT
TTTTTATTTATGCAGAGGCCGAGGCCGCCTCTGCCTCTGAGCTATTCCAGAAGT
AGTGAGGAGGCTTTTTTGGAGGCCTAGGCTTTTGCAAAAAGCTCCCGGGAGCT
TGTATATCCATTTTCGGATCTGATCAGCACGTGTTGACAATTAATCATCGGCA
TAGTATATCGGCATAGTATAATACGACAAGGTGAGGAACTAAACCATGGCCAA
GCCTTTGTCTCAAGAAGAATCCACCCTCATTGAAAGAGCAACGGCTACAATCA
ACAGCATCCCCATCTCTGAAGACTACAGCGTCGCCAGCGCAGCTCTCTCTAGCG
ACGGCCGCATCTTCACTGGTGTCAATGTATATCATTTTACTGGGGGACCTTGTG
CAGAACTCGTGGTGCTGGGCACTGCTGCTGCTGCGGCAGCTGGCAACCTGACTT
GTATCGTCGCGATCGGAAATGAGAACAGGGGCATCTTGAGCCCCTGCGGACGG
TGCCGACAGGTGCTTCTCGATCTGCATCCTGGGATCAAAGCCATAGTGAAGGA
CAGTGATGGACAGCCGACGGCAGTTGGGATTCGTGAATTGCTGCCCTCTGGTT
ATGTGTGGGAGGGCTAAGCACTTCGTGGCCGAGGAGCAGGACTGACACGTGCT
ACGAGATTTCGATTCCACCGCCGCCTTCTATGAAAGGTTGGGCTTCGGAATCGT
TTTCCGGGACGCCGGCTGGATGATCCTCCAGCGCGGGGATCTCATGCTGGAGTT
CTTCGCCCACCCCAACTTGTTTATTGCAGCTTATAATGGTTACAAATAAAGCAA
TAGCATCACAAATTTCACAAATAAAGCATTTTTTTCACTGCATTCTAGTTGTG
GTTTGTCCAAACTCATCAATGTATCTTATCATGTCTGTATACCGTCGACCTCTA
GCTAGAGCTTGGCGTAATCATGGTCATAGCTGTTTCCTGTGTGAAATTGTTAT
CCGCTCACAATTCCACACAACATACGAGCCGGAAGCATAAAGTGTAAAGCCTG
GGGTGCCTAATGAGTGAGCTAACTCACATTAATTGCGTTGCGCTCACTGCCCGC
TTTCCAGTCGGGAAACCTGTCGTGCCAGCTGCATTAATGAATCGGCCAACGCGC
GGGGAGAGGCGGTTTGCGTATTGGGCGCTCTTCCGCTTCCTCGCTCACTGACTC
GCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCC

FIG. 22 cont.

CTCGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACAC
TAGAAGAACAGTATTTGGTATCTGCGCTCTGCTGAAGCCAGTTACCTTCGGAA
AAAGAGTTGGTAGCTCTTGATCCGGCAAACAAACCACCGCTGGTAGCGGTGGT
TTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAA
ATTAAAAATGAAGTTTTAAATCAATCTAAAGTATATATGAGTAAACTTGGTCT
GACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAG
GGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAG
TGGTCCTGCAACTTTATCCGCCTCCATCCAGTCTATTAATTGTTGCCGGGAAGC
TAGAGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCCGGTT
CCCAACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTTATCA
CTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTAT
GCGGCGACCGAGTTGCTCTTGCCCGGCGTCAATACGGGATAATACCGCGCCACA
TAGCAGAACTTTAAAAGTGCTCATCATTGGAAAACGTTCTTCGGGGCGAAAAC
TCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGTTGA
ATACTCATACTCTTCCTTTTTCAATATTATTGAAGCATTTATCAGGGTTATTG
TCTCATGAGCGGATACATATTTGAATGTATTTAGAAAAATAAACAAATAGGGG
TTCCGCGCACATTTCCCCGAAAAGTGCCACCTGACGTC

FIG. 23

>pCMV6-h41BBL (5643 bp)
AACAAAATATTAACGCTTACAATTTCCATTCGCCATTCAGGCTGCGCAACTGTT
GGGAAGGGCGATCGGTGCGGGCCTCTTCGCTATTACGCCAGCTGGCGAAAGGG
GGATGTGCTGCAAGGCGATTAAGTTGGGTAACGCCAGGGTTTTCCCAGTCACG
ACGTTGTAAAACGACGGCCAGTGCCAAGCTGATCTATACATTGAATCAATATT
GGCAATTAGCCATATTAGTCATTGGTTATATAGCATAAATCAATATTGGCTAT
TGGCCATTGCATACGTTGTATCTATATCATAATATGTACATTTATATTGGCTC
ATGTCCAATATGACCGCCATGTTGACATTGATTATTGACTAGTTATTAATAGT
AATCAATTACGGGGTCATTAGTTCATAGCCCATATATGGAGTTCCGCGTTACA
TAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTG
ACGTCAATGGGTGGAGTATTTACGGTAAACTGCCCACTTGGCAGTACATCAAG
TGTATCATATGCCAAGTCCGCCCCCTATTGACGTCAATGACGGTAAATGGCCCG
CCTGGCATTATGCCCAGTACATGACCTTACGGGACTTTCCTACTTGGCAGTACA
TCTACGTATTAGTCATCGCTATTACCATGGTGATGCGGTTTTGGCAGTACACCA
ATGGGCGTGGATAGCGGTTTGACTCACGGGGATTTCCAAGTCTCCACCCCATTG
ACGTCAATGGGAGTTTGTTTTGGCACCAAAATCAACGGGACTTTCCAAAATGT
CGTAATAACCCCGCCCCGTTGACGCAAATGGGCGGTAGGCGTGTACGGTGGGA
GGTCTATATAAGCAGAGCTCGTTTAGTGAACCGTCAGAATTTTGTAATACGAC
TCACTATAGGGCGGCCGGGAATTCGTCGACTGGATCCGGTACCGAGGAGATCT
GCCGCCGCGATCGCCATGGAATACGCCTCTGACGCTTCACTGGACCCCGAAGCC
CCGTGGCCTCCCGCGCCCCGCGCTCGCGCCTGCCGCGTACTGCCTTGGGCCCTGG
TCGCGGGGCTGCTGCTGCTGCTGCTGCTCGCTGCCGCCTGCGCCGTCTTCCTCGC
CTGCCCCTGGGCCGTGTCCGGGGCTCGCGCCTCGCCCGGCTCCGCGGCCAGCCCG
AGACTCCGCGAGGGTCCCGAGCTTTCGCCCGACGATCCCGCCGGCCTCTTGGAC
CTGCGGCAGGGCATGTTTGCGCAGCTGGTGGCCCAAAATGTTCTGCTGATCGAT
GGGCCCCTGAGCTGGTACAGTGACCCAGGCCTGGCAGGCGTGTCCCTGACGGGG
GGCCTGAGCTACAAAGAGGACACGAAGGAGCTGGTGGTGGCCAAGGCTGGAGT
CTACTATGTCTTCTTTCAACTAGAGCTGCGGCGCGTGGTGGCCGGCGAGGGCTC
AGGCTCCGTTTCACTTGCGCTGCACCTGCAGCCACTGCGCTCTGCTGCTGGGGC
CGCCGCCCTGGCTTTGACCGTGGACCTGCCACCCGCCTCCTCCGAGGCTCGGAA
CTCGGCCTTCGGTTTCCAGGGCCGCTTGCTGCACCTGAGTGCCGGCCAGCGCCT
GGGCGTCCATCTTCACACTGAGGCCAGGGCACGCCATGCCTGGCAGCTTACCCA
GGGCGCCACAGTCTTGGGACTCTTCCGGGTGACCCCCGAAATCCCAGCCGGACT
CCCTTCACCGAGGTCGGAAACGCGTACGCGGCCGCTCGAGCAGAAACTCATCTC
AGAAGAGGATCTGGCAGCAAATGATATCCTGGATTACAAGGATGACGACGATA
AGGTTTAAACGGCCGGCCGCGGTCATAGCTGTTTCCTGAACAGATCCCGGGTGG
CATCCCTGTGACCCCTCCCCAGTGCCTCTCCTGGCCCTGGAAGTTGCCACTCCA

FIG. 23 cont.

GTGCCCACCAGCCTTGTCCTAATAAAATTAAGTTGCATCATTTTGTCTGACTAG
GTGTCCTTCTATAATATTATGGGGTGGAGGGGGGTGGTATGGAGCAAGGGGCA
AGTTGGGAAGACAACCTGTAGGGCCTGCGGGGTCTATTGGGAACCAAGCTGGA
GTGCAGTGGCACAATCTTGGCTCACTGCAATCTCCGCCTCCTGGGTTCAAGCGA
TTCTCCTGCCTCAGCCTCCCGAGTTGTTGGGATTCCAGGCATGCATGACCAGGC
TCAGCTAATTTTTGTTTTTTTGGTAGAGACGGGGTTTCACCATATTGGCCAGG
CTGGTCTCCAACTCCTAATCTCAGGTGATCTACCCACCTTGGCCTCCCAAATTG
CTGGGATTACAGGCGTGAACCACTGCTCCCTTCCCTGTCCTTCTGATTTTAAAA
TAACTATACCAGCAGGAGGACGTCCAGACACAGCATAGGCTACCTGGCCATGCC
CAACCGGTGGGACATTTGAGTTGCTTGCTTGGCACTGTCCTCTCATGCGTTGGG
TCCACTCAGTAGATGCCTGTTGAATTGGGTACGCGGCCAGCGGCGAGCGGTATC
AGCTCACTCAAAGGCGGTAATACGGTTATCCACAGAATCAGGGGATAACGCAG
GAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAGCTCA
CGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAAC
AGGATTAGCAGAGCGAGGTATGTAGGCGGTGCTACAGAGTTCTTGAAGTGGTG
GCCTAACTACGGCTACACTAGAAGAACAGTATTTGGTATCTGCGCTCTGCTGA
AGCCAGTTACCTTCGGAAAAAGAGTTGGTAGCTCTTGATCCGGCAAACAAACC
ACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGT
GGAACGAAAACTCACGTTAAGGGATTTTGGTCATGAGATTATCAAAAAGGATC
TTCACCTAGATCCTTTTAAATTAAAAATGAAGTTTTAAATCAATCTAAAGTAT
ATATGAGTAACCTGAGGCTATGGCAGGGCCTGCCGCCCCGACGTTGGCTGCGAG
CCCTGGGCCTTCACCCGAACTTGGGGGGTGGGGTGGGGAAAAGGAAGAAACGC
GGGCGTATTGGCCCCAATGGGGTCTCGGTGGGGTATCGACAGAGTGCCAGCCCT
GGGACCGAACCCCGCGTTTATGAACAAACGACCCAACACCGTGCGTTTTATTCT
GTCTTTTTATTGCCGTCATAGCGCGGGTTCCTTCCGGTATTGTCTCCTTCCGTG
TTTCAGTTAGCCTCCCCCTAGGGTGGGCGAAGAACTCCAGCATGAGATCCCCGC
GCTGGAGGATCATCCAGCCGGCGTCCCGGAAAACGATTCCGAAGCCCAACCTTT
CATAGAAGGCGGCGGTGGAATCGAAATCTCGTGATGGCAGGTTGGGCGTCGCT
TGGTCGGTCATTTCGAACCCCAGAGTCCCGCTCAGAAGAACTCGTCAAGAAGGC
GATAGAAGGCGATGCGCTGCGAATCGGGAGCGGCGATACCGTAAAGCACGAGG
AAGCGGTCAGCCCATTCGCCGCCAAGCTCTTCAGCAATATCACGGGTAGCCAAC

FIG. 23 cont.

GCTATGTCCTGATAGCGATCCGCCACACCCAGCCGGCCACAGTCGATGAATCCA
GAAAAGCGGCCATTTTCCACCATGATATTCGGCAAGCAGGCATCGCCATGGGTC
ACGACGAGATCCTCGCCGTCGGGCATGCTCGCCTTGAGCCTGGCGAACAGTTCG
GCTGGCGCGAGCCCCTGATGCTCTTCGTCCAGATCATCCTGATCGACAAGACCG
GCTTCCATCCGAGTACGTGCTCGCTCGATGCGATGTTTCGCTTGGTGGTCGAAT
GGGCAGGTAGCCGGATCAAGCGTATGCAGCCGCCGCATTGCATCAGCCATGAT
GGATACTTTCTCGGCAGGAGCAAGGTGAGATGACAGGAGATCCTGCCCCGGCA
CTTCGCCCAATAGCAGCCAGTCCCTTCCCGCTTCAGTGACAACGTCGAGCACAG
CTGCGCAAGGAACGCCCGTCGTGGCCAGCCACGATAGCCGCGCTGCCTCGTCTT
GCAGTTCATTCAGGGCACCGGACAGGTCGGTCTTGACAAAAAGAACCGGGCGC
CCCTGCGCTGACAGCCGGAACACGGCGGCATCAGAGCAGCCGATTGTCTGTTGT
GCCCAGTCATAGCCGAATAGCCTCTCCACCCAAGCGGCCGGAGAACCTGCGTGC
AATCCATCTTGTTCAATCATGCGAAACGATCCTCATCCTGTCTCTTGATCGATC
TTTGCAAAAGCCTAGGCCTCCAAAAAAGCCTCCTCACTACTTCTGGAATAGCTC
AGAGGCCGAGGCGGCCTCGGCCTCTGCATAAATAAAAAAAATTAGTCAGCCAT
GGGGCGGAGAATGGGCGGAACTGGGCGGAGTTAGGGGCGGGATGGGCGGAGTT
AGGGGCGGGACTATGGTTGCTGACTAATTGAGATGCATGCTTTGCATACTTCT
GCCTGCTGGGGAGCCTGGGGACTTTCCACACCTGGTTGCTGACTAATTGAGATG
CATGCTTTGCATACTTCTGCCTGCTGGGGAGCCTGGGGACTTTCCACACCCTAA
CTGACACACATTCCACAGCTGGTTCTTTCCGCCTCAGGACTCTTCCTTTTTCAA
TATTATTGAAGCATTTATCAGGGTTATTGTCTCATGAGCGGATACATATTTGA
ATGTATTTAGAAAAATAAACAAATAGGGGTTCCGCGCACATTTCCCCGAAAAG
TGCCACCTGACGCGCCCTGTAGCGGCGCATTAAGCGCGGCGGGTGTGGTGGTTA
CGCGCAGCGTGACCGCTACACTTGCCAGCGCCCTAGCGCCCGCTCCTTTCGCTT
TCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAA
ACTTGATTAGGGTGATGGTTCACGTAGTGGGCCATCGCCCTGATAGACGGTTT
TTCGCCCTTTGACGTTGGAGTCCACGTTCTTTAATAGTGGACTCTTGTTCCAAA
CTGGAACAACACTCAACCCTATCTCGGTCTATTCTTTTGATTTATAAGGATTT
TGCCGATTTCGGCCTATTGGTTAAAAAATGAGCTGATTTAACAAAAATTTAAC
GCGAATTTT

METHOD FOR EXPANSION OF LYMPHOCYTES

CROSS-REFERENCE TO RELATED APPLICATIONS

This application is a U.S. National Phase of International Patent Application No. PCT/EP2018/080343, filed on Nov. 6, 2018, which published as WO 2019/086711 A1 on May 9, 2019, which claims priority from U.S. Provisional Application Ser. No. 62/582,163 filed on Nov. 6, 2017, all of which is incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 27, 2018, is named 252457_000003_SL.txt and is 109,494 bytes in size.

FIELD OF THE INVENTION

The invention relates to a method for expanding antigen-specific lymphocytes by culturing samples from a subject containing lymphocytes or culturing lymphocytes derived from the sample in the presence of one or more peptides comprising antigens and/or in the presence of an antigen presenting cell presenting antigens. Also disclosed is the use of such method for improving personalized immunotherapy.

BACKGROUND

Immunogenic tumors can benefit from different immunotherapeutic interventions. Among them, adoptive cell transfer (ACT) of autologous tumor-infiltrating lymphocytes (TILs) is effective in mediating tumor regression.

Recent technological advances have accelerated the identification of T cell specificities against so-called tumor neo-antigens resulting from non-synonymous somatic tumor mutations. Neo-antigens are ideal potential targets for immunotherapy, not only because they are highly tumor-specific, but also because high-avidity and/or affinity neo-antigen-specific T cells should not be counter selected by the thymus[2-4]. Not only have neo-antigens shown to be key mediators of successful immune checkpoint blockade therapies[5-7], they have also been successfully used in ACT[8,9]. Finally, several groups provide direct evidence of tumor regression mediated by neo-antigen-specific T cells. Indeed, Tran and colleagues first demonstrated the latter by ACT of neo-antigen-reactive $CD4^+$ T cells in epithelial cancer[10]. Most recently, Sahin and Ott demonstrated a complete response by melanoma patients treated with personalized neo-antigen vaccination (mRNA[11]- and peptide[12]-based, respectively) in combination with immune checkpoint blockade[11,12].

Current protocols for expansion of TILs typically involve two main amplification processes. An initial TIL culture involves the incubation of tumor samples in a culture medium enriched with interleukin-2 (IL-2) to obtain an initial bulk amount of TILs. TILs obtained during this initial phase then typically undergo a rapid amplification protocol ("REP"). The REP process increases the final number of TILs to the order of $10^9$-$10^{11}$.

Although the conventional TIL expansion have served patients well with cancer, there is a need in the art to optimize the TIL culture process to maximize the recovery of neo-antigen-specific T cell clones or enrich neo-antigen-specific TILs. The invention disclosed herein addresses this need and is also applicable to other antigens beyond tumor-specific neo-antigens.

SUMMARY OF THE INVENTION

There is a great need in the art for improving personalized immunotherapy. The present invention addresses this and other needs by providing a method for enriching antigen-specific lymphocytes by culturing samples from a subject, wherein the sample contains lymphocytes, or lymphocytes derived therefrom in the presence of one or more peptides comprising antigens.

In one aspect, the invention provides a method for enrichment and expansion of neo-antigen-specific lymphocytes ex vivo comprising culturing a sample obtained from a subject or lymphocytes derived therefrom in the presence of one or more peptides, wherein each of said peptides comprises a different antigen.

Any number of peptides can be used in the method of the invention. Preferably, the number of different peptides should be such that a competition for MHC molecules should be minimized to avoid suboptimal stimulation of some T cell clonotypes. In some embodiments, the method involves culturing in the presence of two or more peptides, wherein each of said peptides comprises a different tumor-specific neo-antigen. In some embodiments, the method involves culturing in the presence of 1-300 peptides, wherein each of said peptides comprises a different tumor-specific neo-antigen. In some embodiments, the method involves culturing in the presence of 1-100 peptides, wherein each of said peptides comprises a different tumor-specific neo-antigen. In some embodiments, the method involves culturing in the presence of 20-50 peptides, wherein each of said peptides comprises a different tumor-specific neo-antigen.

In one aspect, described herein are methods for expanding antigen-specific lymphocytes ex vivo comprising expanding lymphocytes in a sample obtained from a subject or lymphocytes isolated from such sample, wherein expanding comprises adding one or more peptides during expansion, wherein each of said peptide(s) comprises a different antigen and wherein antigen-specific lymphocytes are expanded. In certain embodiments, the methods comprise adding two or more peptide(s) (i.e., a pool of different peptides). In certain embodiments, one phase of expansion is conducted, and that phase of expansion is a pre-rapid expansion protocol (pre-REP). In certain embodiments, the first expansion comprises expanding the lymphocytes under conditions that favor growth of lymphocytes over other cells that may be present in the sample. In certain embodiments, the antigen-specific lymphocytes are preferentially expanded over non-antigen-specific lymphocytes.

In another aspect, described herein are methods for expansion of antigen-specific lymphocytes ex vivo comprising a) expanding lymphocytes in a sample obtained from a subject or lymphocytes isolated from such sample, wherein expanding comprises at least two phases of expansion, and b) adding one or more peptides during at least one of the at least two phases of expansion, wherein each of said peptide(s) comprises a different antigen and wherein antigen-specific lymphocytes are expanded. In certain embodiments, the first expansion comprises expanding the lymphocytes under conditions that favor growth of lymphocytes over other cells that may be present in the sample. In certain embodiments, the antigen-specific lymphocytes are preferentially expanded over non-antigen-specific lymphocytes.

In certain embodiments, the at least two phases of expansion comprise a first expansion and a second expansion. In certain embodiments, the first expansion occurs just prior to the second expansion. In certain embodiments, the peptide(s) are not present during the second expansion.

In certain embodiments, one or more additional expansions occur between the first expansion and second expansion. In certain embodiments, the second expansion is conducted in the presence of at least one of CD3 complex agonist, mitogens, or feeder cells. In certain embodiments, the CD3 complex agonist is an anti-CD3 complex agonist antibody (e.g., OKT-3). In certain embodiments, the mitogen is at least one of phytohemagglutinin (PHA), concanavalin A (Con A), pokeweed mitogen (PWM), mezerein (Mzn), or tetradecanoyl phorbol acetate (TPA). In certain embodiments, the feed cells are autologous, allogenic, and/or irradiated. In certain embodiments, the feeder cells are peripheral blood mononuclear cells (PBMCs). In certain embodiments, the feeder cells and lymphocytes are present at a ratio of about 1000:1 to about 1:1. In other embodiments, the feeder cells and lymphocytes are present at a ratio of about 100:1.

In certain embodiments, step b) comprises adding two or more peptides during at least one of the at least two phases of expansion, wherein each of said peptide(s) comprises a different antigen. In other embodiments, step b) comprises adding the peptide(s) at the initiation of at least one of the at least two phases of expansion. In additional embodiments, step b) further comprises re-adding the peptide(s) at least once. In yet an additional embodiment, step b) further comprises re-adding the peptide(s) every day after the first addition. In yet another embodiment, step b) further comprises re-adding the peptide(s) every other day after the first addition.

In certain embodiments of the methods disclosed herein, the peptide(s) are re-added at least two days after the first day.

In certain embodiments of the methods disclosed herein, the peptide(s) are in a soluble form. In certain embodiments, the peptide(s) are at a concentration of about 0.1 nM to about 100 μM. In certain embodiments, the peptide(s) are from about 9 amino acids long to about 31 amino acids long. In some embodiments, the peptide(s) are 9 or 10 amino acids long. In some embodiments, the peptide(s) are 12 to 15 amino acids long. In some embodiments, the peptide(s) are about 25 to about 31 amino acids long. In some embodiments, the peptides are present in a pool of about 2 to about 300 different peptides. In some embodiments, the peptides are present in a pool of about 2 to about 300 different peptides. In some embodiments, the peptides are present in a pool of about 2 to about 100 different peptides, about 10 to about 100, about 20 to about 100, about 30 to about 100, about 40 to about 100, about 50 to about 100, about 60 to about 100, about 70 to about 100, about 80 to about 100 or about 90 to about 100. In certain embodiments, the peptides are present in a pool of about 20 to about 50 different peptides. In certain embodiments, the peptide(s) are present in a pool of about 2 to about 10 different peptides. In other embodiments, the peptide(s) are present in a pool of about 2 to about 5 different peptides. In certain embodiments, the peptide(s) are present at a concentration of about 1 μM.

In certain embodiments of the methods disclosed herein, the peptide(s) are added at the initiation of the first expansion. In some embodiments, the peptide(s) are added at the initiation of the first extension and every other day for two days.

In certain embodiments of the methods disclosed herein, the peptide(s) are presented on the surface of an antigen presenting cell (APC). In certain embodiments, the ratio of cells present in the sample (e.g., tissue or bodily fluid) to APCs is from about 1:1 to about 1:100. In certain embodiments, the ratio of cells present in the sample to APCs is about 1:1. In other embodiments, ratio of lymphocytes to APCs is from about 0.01:1 to about 100:1, wherein the lymphocytes are isolated from the sample. In certain embodiments, ratio of lymphocytes to APCs is about 1:1. In certain embodiments, the APC presenting the peptide is added at the initiation of the first expansion.

In certain embodiments of the methods disclosed herein, the APC has been preincubated with the peptide(s) in a soluble form. In certain embodiments, the peptide(s) are from about 9 amino acids long to about 31 amino acids long. In some embodiments, the peptide(s) are 9 or 10 amino acids long. In some embodiments, the peptide(s) are 12 to 15 amino acids long. In some embodiments, the peptide(s) are about 25 to about 31 amino acids long. In some embodiments, the peptides are present in a pool of about 2 to about 300 different peptides. In some embodiments, the peptides are present in a pool of about 2 to about 100 different peptides, about 10 to about 100, about 20 to about 100, about 30 to about 100, about 40 to about 100, about 50 to about 100, about 60 to about 100, about 70 to about 100, about 80 to about 100 or about 90 to about 100. In certain embodiments, the peptides are present in a pool of about 20 to about 50 different peptides. In certain embodiments, the peptide(s) are present in a pool of about 2 to about 10 different peptides. In other embodiments, the peptide(s) are present in a pool of about 2 to about 5 different peptides. In certain embodiments, the peptide(s) are present at a concentration of about 1 μM or 2 μM.

In certain embodiments of the methods disclosed herein, the APC has been engineered to express said peptide(s) on its surface. In certain embodiments, the APC is engineered by at least one of transfection, transduction, or temporary cell membrane disruption to introduce at least one polynucleotide encoding said peptide(s) into the APC. In certain embodiments, the at least one polynucleotide is a DNA plasmid and/or an mRNA encoding said peptide(s). In certain embodiments, the mRNA comprises about 50 to about 5000 nucleotides. In another embodiment, the mRNA comprises about 75 to about 4000, about 75 to about 3000, about 75 to about 2000, about 75 to about 1000, about 75 to about 500 nucleotides. In certain embodiments, the polynucleotide comprises 1 to about 15 genes encoding the peptide(s). In other embodiments, the polynucleotide consists essentially of one gene encoding a single peptide. In some embodiments, the mRNA is at least one polynucleotide comprising at least two genes encoding said peptide(s) in tandem. In other embodiments, the mRNA is a single polynucleotide comprising at least two genes encoding said peptide(s) in tandem. In certain embodiments, there is a total of about 2 to about 40, about 2 to about 15, or about 2 to about 5 gene encoding peptides. In certain embodiments, each polynucleotide comprises 5 genes encoding peptides. In certain embodiments, each gene encodes a polypeptide that is about 9 to about 31 amino acids long and centered on an individual mutated amino acid found within the antigen, wherein the genes are optionally separated by a linker.

In certain embodiments of the methods disclosed herein, the APC is engineered to express at least one immunomodulator, wherein the immunomodulator is at least one of OX40L, 4-1BBL, CD80, CD86, CD83, CD70, CD40L, GITR-L, CD127L, CD30L (CD153), LIGHT, BTLA, ICOS-L (CD275), SLAM (CD150), CD662L, interleukin-12 (IL-12), interleukin-7 (IL-7), interleukin-15 (IL-15), interleukin-17 (IL-17), interleukin-21 (IL-21), interleukin-4 (IL-4), Bcl-6, Bcl-XL, BCL-2, MCL1, or STAT-5, or activators of at least one of the JAK/STAT pathway, PI3K-AKT signaling pathway, BCR signaling pathway, or BAFF-BAFFR signaling pathway. In certain embodiments, the immunomodulator is at least one of OX40L, 4-1BBL, or IL-12. In certain embodiments, the APCs are engineered to transiently or stably express the immunomodulator. In certain embodiments, the engineered APC is added at the initiation of the first expansion and added at least one additional day. In certain embodiments, the engineered APC is added at the initiation of the first expansion and again 10 days after the first addition.

In certain embodiments of the methods disclosed herein, the APC is engineered by at least one of transfection, transduction, or temporary cell membrane disruption thereof to introduce the at least one immunomodulator. In certain embodiments, transfection occurs by electroporation.

In certain embodiments, the peptide(s) have been identified by predictive modeling, whole-exome sequencing, whole genome sequencing, RNA sequencing, or mass spectrometry. In certain embodiments, the antigens have been preselected based on identifying antigen-specific mutations. In other embodiments, the antigens have been preselected based on identifying antigen-specific mutations.

In certain embodiments of the methods disclosed herein, the lymphocytes are expanded in the presence of at least one expansion-promoting agent. In certain embodiments, the expansion-promoting agents is an immunomodulatory agent. In certain embodiments, the immunomodulatory agent is a cytokine such as, but not limited to, interleukin-2 (IL-2), interleukin-4 (IL-4), interleukin-7 (IL-7), interleukin-15 (IL-15), interleukin-17 (IL-17), or interleukin-21 (IL-21). In certain embodiments, the expansion-promoting agent is a soluble molecule (e.g., an antagonist of at least one of PD-1, CTLA-4, 4-1BB, LAG-3, TIM-3, 2B4/CD244/SLAMF4, CD160, TIGIT, TCF1, CD39, or BATF). In other embodiments, the expansion-promoting agents is an antibody favoring the expansion of lymphocytes (e.g., antibody against at least one of PD-1, CTLA-4, 4-1BB, LAG-3, TIM-3, 2B4/CD244/SLAMF4, CD160, TIGIT, TCF1, CD39, or BATF). In certain embodiments, the expansion-promoting agents is IL-2. In certain embodiments, IL-2 is present during the first expansion within a range of about 100 IU/ml to about 10,000 IU/ml. In certain embodiments, IL-2 is present during the first expansion at a concentration of about 6,000 IU/ml. In certain embodiments, IL-2 is present during the second expansion within a range of about 50 IU/ml to about 10,000 IU/ml. In certain embodiments, IL-2 is present during the second expansion at a concentration of about 3,000 IU/ml.

In certain embodiments of the methods disclosed herein, the lymphocytes are tumor-infiltrating lymphocytes (TILs) and/or peripheral blood lymphocytes (PBLs). In certain embodiments, the lymphocytes are T cells (e.g., CD8+ or CD4+ T cells).

In certain embodiments, the wherein the sample is obtained from draining lymph nodes. In other embodiments, the sample is an untreated tumor fragment, enzymatically treated tumor fragment, dissociated/suspended tumor cells, a lymph node sample, or a bodily fluid (e.g., blood, ascites, or lymph) sample. In certain embodiments, the enzymatically treated tumor fragment has been treated with at least one of collagenase, dispase, hyaluronidase, liberase, or deoxyribonuclease (DNase).

In certain embodiments of the methods disclosed herein, the APC is activated. In certain embodiments, the APC is autologous, allogenic, or artificial. In certain embodiments, the APC is a B cell, dendritic cell, macrophage, or Langerhans cell. In certain embodiments, the APC is a B cell (e.g., CD19+). In certain embodiments, the B cell is activated by incubation with at least one of CD40L, IL-21, or IL-4. In certain embodiments, the B cells are further cultured with at least one of Bcl-6, Bcl-XL, BCL-2, MCL1, STAT-5, or an activator of at least one of the JAK/STAT pathway, PI3K-AKT signaling pathway, BCR signaling pathway, or BAFF-BAFFR signaling pathway.

In certain embodiments of the methods disclosed herein, the antigen is a tumor antigen, post-translational modification, long-noncoding antigen, or viral antigen. In certain embodiments, tumor antigen is a shared tumor antigen, overexpressed tumor antigen, aberrantly expressed tumor antigen, or tumor-specific neo-antigen. In certain embodiments, the tumor-specific neo-antigen is a canonical neoantigen or a non-canonical neoantigen. In certain embodiments, the tumor antigen is from a solid tumor (e.g., ovarian tumor, a melanoma, a lung tumor, a breast tumor, or a gastrointestinal antigen), or a liquid tumor (e.g. a leukemia, or a lymphoma)

In certain embodiments of the methods disclosed herein, the methods further comprise isolating the antigen-specific lymphocytes after the culturing. In certain embodiments, the methods further comprise obtaining the sample from the subject prior to the culturing. In certain embodiments, the methods further comprise isolating lymphocytes from the sample before the culturing. In certain embodiments, the methods further comprise isolating antigen-specific lymphocytes from the sample before the culturing.

In certain embodiments of the methods disclosed herein, exposure to the peptide(s) during the first expansion results in an improvement in the frequency of the lymphocytes. In certain embodiments, exposure to the peptide(s) during the first expansion results in an improvement in the frequency of antigen-specific lymphocytes. In certain embodiments, the improvement in frequency of lymphocytes and/or antigen-specific lymphocytes is over methods in which lymphocytes are not exposed to peptide(s) during the first expansion.

In certain embodiments of the methods disclosed herein, exposure to the peptide(s) during the first expansion results in antigen-specific lymphocytes with less exhaustion as compared to antigen-specific lymphocytes exposed to the peptide(s) in only the second expansion. In other embodiments, exposure to the peptide(s) during the first expansion but not the second expansion results in antigen-specific lymphocytes with less exhaustion as compared antigen-specific lymphocytes exposed to the peptide(s) in the first and second expansion. In yet other embodiments, exposure to the peptide(s) during the first expansion but not the second expansion results in antigen-specific lymphocytes with less exhaustion as compared antigen-specific lymphocytes exposed to the peptide(s) only in the second expansion.

In certain embodiments of the methods disclosed herein, the methods further comprising reintroducing the antigen-specific lymphocytes into the subject.

In certain embodiments of the methods disclosed herein, the subject is human.

In another aspect, the invention relates to a population of antigen-specific lymphocytes produced by the methods disclosed herein.

In another aspect, described herein are methods of treating a tumor in a subject in need thereof comprising administering to the subject the effective amount of the lymphocytes made by the methods as disclosed herein. In certain embodiments, the tumor is a solid tumor (e.g., ovarian tumor, a melanoma, a lung tumor, a gastrointestinal tumor, a breast tumor). In certain embodiments, the tumor is a liquid tumor (e.g., a leukemia, or a lymphoma). In certain embodiments, the tumor expresses a mutation consistent with at least one peptide comprising a tumor antigen. In certain embodiments, the subject is human.

These and other aspects of the present invention will be apparent to those of ordinary skill in the art in the following description, claims, and drawings.

BRIEF DESCRIPTION OF THE DRAWINGS

FIG. 1B). A pool of 50-100 private peptides (i.e., specifically predicted for this patient) was used. The peptides were from 9 to 10 amino acids long.

FIG. 6A shows the principle of tandem minigenes (TMG), each minigene encodes a 31-mer centered on an individual point mutation. FIG. 6A discloses SEQ ID NO: 261. FIG. 6B illustrates the details of the generation of transfected CD40-activated B cells. The left-hand side of the figure depicts the design of the vector based on an identified mutation followed by the transformation into the bacteria and subsequent amplification within the bacteria. Next, the DNA is linearized and polyadenylated in vitro transcribed (IVT) mRNA is produced, which is then transfected (e.g., via electroporation) into CD40-activated B cells. The right-hand side of the figure depicts the generation of CD40-activated B cells enriched via CD19 isolation, wherein stimulation with multimeric CD40 ligand occurs in the presence of IL-4. These processes generate CD40-activated B cells presenting neo-antigens. These activated B cells can be used for i) screening for neo-antigen-specific TILs (i.e., neo-antigen TIL reactives), or ii) to enrich neo-antigen-specific TILs via stimulation with transfected CD40-activated B cell stimulation.

FIG. 7 shows a non-limiting embodiment for developing the vector template for IVT mRNA used for transfection into CD40-activated B cells. The T7 promoter is used for the initiation of the IVT reaction; a signaling peptide (SP), MHCI trafficking signal (MITD), and linker sequences are used for the correct processing and presentation of class I and class II 25-31mers. The right-hand side of the figure depicts a non-limiting embodiment of an amino acid sequence composing each of the represented elements. The UTR used in the embodiment is a tandem beta-globin 3' nucleotide UTR sequence. FIG. 7 discloses SEQ ID NOS 262-266, respectively, in order of appearance.

FIG. 8A shows antigen stimulation levels generated by peptide preloaded B cells (Peptide) or TMG-B cells with MelanA CD8+ antigens (MelanA: TMG 103 from Table 2). In FIG. 8B, TILs from ovarian cancer patient CTE-009 were cultured with preloaded B cells (Peptide) or TMG-B cells (TMG) and assayed by ELISpot and CD137 positivity; peptides and TMG coding for CTE-009 specific neo-antigens were used (Peptide: IPINPRRCL (SEQ ID NO: 1); COPG2: TMG 105 from Table 2). FIG. 8C shows an ELISpot graph showing the half-life of antigen stimulation post-electroporation of TMG-B cells: several batches of HLA-A2+CD40-activated B cells rested for the indicated times and co-cultured with MelanA CD8+ clones (MelanA: TMG 103 from Table 2). This demonstrates how long the expression of TMG lasts in APCs. Peptide: B cells were pre-loaded with peptides coding for neo-antigens. TMG: B cells were electroporated with mRNA coding for neo-antigens. PMA (50 ng/ml) was used as a positive control. Mock is empty or non-coding mRNA.

FIG. 9A shows representative examples of PBMC enriched in Flu MP117-31 (MHC-I antigen) and Flu MP131mer (MHC-II antigen) co-cultured with peptide pulsed APC or TMG-APC (TMG 103 from Table 2). PBMC were interrogated for the expression of intracellular cytokines TNFα and IFNγ. FIG. 9B shows ELISpot assay of $MageA3_{111-126}$ specific $CD4^+$ clones co-culture with $MageA3_{111-126}$ peptide (Peptide; RKVAELVHFLLLKYRA (SEQ ID NO: 2)) pulsed B cells or with B cells transfected with TMG expressing $MageA3_{111-126}$ (TMG 103 from Table 2). ON: overnight. Mock is empty or non-coding mRNA.

In FIG. 10A, tumor enzymatic digestions from ovarian cancer patient CTE-006 were incubated with the conventional conditions (Conventional; 6000 IU/ml IL-2) or were primed (Primed) by addition of a pool of three peptides (9-10-mers). The responsiveness of the TILs was tested by detecting IFNγ secretion after stimulation with neo-antigens (Pool Mut, gray bar). In FIG. 10B, the effect of different ratios and with TMG-B cells was tested. CD40-activated B cells were electroporated (where indicated, TMG (TMG 106-$CDC120_{31mer}$ cognate neo-antigen)), with different ratio of B cells to digested tumor cells (1:1 or 1:2 as indicated). In all the tested conditions, CD40-activated B cells were used; antibodies anti-PD1 and anti-CTLA4 were used at the time of generation and medium was renewed with inhibitors. TILs were screened for IFNγ production by incubation with a peptide coding for $CDC120_{S231C}$ (Pool Mut, gray bar). For FIG. 10A-10B, the culture media was supplemented with 10 μg/mL anti-PD1 mAb (eBiosciences) and 10 μg/mL anti-CTLA-4 mAb (Ipilimumab, Bristol-Myers) during the whole period of TIL culture.

FIG. 12 shows TILs enrichment using engineered B cells after one (day 0) or two (day 0 and day 10) rounds of stimulation in tissues and cells from ovarian cancer patient CTE-007. The percentage of CD137+CD4+ neo-antigen reactive TILs was determined by FACS analysis. The TILs were either not co-incubated with B cells (Conventional) or co-incubated with B cells that were either pulsed (i.e., pre-loaded) with peptides (APC, peptides; peptides were specific for the patient, 9-25mers), transfected with tandem minigenes (TMG-APC; TMG 105 (SGOL1 cognate neo-antigen)), or engineered to express both tandem minigenes and immunostimulatory molecules OX40-L, IL12, and 4-1BBL (Engineered TMG-APC). Where indicated (day 10), re-stimulation was performed. Incubation with neo-antigens (Pool Mut) was performed for the screening of the TILs activity. Culture media was supplemented with 10 μg/mL anti-PD1 mAb (eBiosciences) and 10 μg/mL anti-CTLA-4 mAb (Ipilimumab, Bristol-Myers) during the whole period of TIL culture.

FIG. 13 shows the fold expansion of TILs in the presence of B cells. Data show the fold expansion of total number of bulk TILs with conventional methods and in presence of B cells during the pre-REP phase. Tumor samples were dissociated from ovarian cancer patients CTE-005 (square), CTE-006 (circle), and CTE-010 (diamond). Data represent cumulative expansion of different conditions of pre-REP.

FIG. 14 ($1^{st}$ row): TIL enrichment was observed in cells from melanoma patient Mel0011 (tumor fragments) by comparing the conventional versus the primed TIL (pool of 50 peptides, 9- and 10-mers). FIG. 14 ($2^{nd}$ row): Enrichment of TILs was observed also in colorectal cancer CrCp5 (tumor fragments) when conventional method is compared with B cells expressing tandem minigene and immunostimulatory molecules added once on day 0 (Engineered TMG-APC) or twice (i.e., day 0 and 10) (Engineered TMG-APC, re-stimulation) (TMG 108). FIG. 14 (3rd and 4th rows): Similarly, dissociated ovarian tumors from patients show dramatic enrichment of TILs when the methods of the invention are used (Conventional, Primed, APC, peptides (B cells pulsed with peptide), TMG transfected B cells (TMG-APC), and B cells transfected with TMGs and immunomodulators (Engineered TMG-APC), and re-stimulated where indicated). For TILs from patient CTE-006 (third row), a pool of three peptides and TMG 106 was used; for TILs from patient CTE-007 (fourth row), one 31-mer cognate peptide and TMG 105 were used. Conventional: TILs produced with IL-2 alone; primed: IL-2 with neo-antigen peptides; APC, peptide: co-culture of tumor fragments or digestions with peptide pulsed B cells; TMG-APC: co-culture of tumor fragments or digestion with tandem minigene B cells; Engineered TMG-APC: B cells engineered for immunostimulatory expression and for expression of tandem mini-gene; re-stimulation: APC (engineered TMG-APC and/or TMG-APC) were incubated again at day 10. For rows 3 and 4, culture media was supplemented with 10 μg/mL anti-PD1 mAb (eBiosciences) and 10 μg/mL anti-CTLA-4 mAb (Ipilimumab, Bristol-Myers) during the whole period of TIL culture.

FIG. 15 shows the cumulative analysis of the frequencies of neo-antigen specific CD8+ T cells detected in conventional (x-axis) and enriched (y-axis) TILs (PHLPP2, CDCl20, SGOL1 (i.e., different embodiments using B cells)). NBEA (square) shows data comparing conventional and primed TILs. For CDCl20 and SGOL1, culture media was supplemented with 10 μg/mL anti-PD1 mAb (eBiosciences) and 10 μg/mL anti-CTLA-4 mAb (Ipilimumab, Bristol-Myers) during the whole period of TIL culture.

FIG. 16A (neo-antigens): Peptides comprising neo-antigens (e.g., identified by comparing tumor and control samples) are incubated with tumor fragments, digestions, or with a plurality of cells from a tumor sample obtained from a subject together in the presence of IL-2 to obtain a first antigen-specific TILs population. This first TILs population (pre-REP) next undergoes rapid expansion. FIG. 16B (APCs transfected with tandem minigenes (TMGs)): TMGs encoding neo-antigens (identified by comparing exome and RNA from tumor and control tissue) are synthesized and transfected into APCs for the presentation by MHC class I and/or II. These APCs are then co-cultured with tumor fragments, digestions, or a plurality of cells from a tumor from a subject in the presence of IL-2 to obtain a first TILs population that will be further expanded during a rapid expansion protocol. FIG. 16C (APCs pre-loaded with neo-antigens): APCs are pulsed with neo-antigen containing peptides (identified by comparing tumor and control samples). These APCs are then co-cultured with tumor fragments, digestions, or a plurality of cells from tumor from the subject in presence of IL2. The resulting TIL population (pre-REP) next undergoes rapid expansion. FIG. 16D (Engineered APCs also transfected with TMGs): APCs are engineered to induce the expression of immunostimulatory protein and are induced to present neo-antigens in the context with MHC class I and/or II via transfection with mRNA encoding for neo-antigens. The engineered APCs, now presenting neo-antigens, are then incubated with tumor fragments, digestions, or a plurality of cells from a tumor sample in the presence of IL2 to produce a pre-REP TIL population. These pre-REP TIL are further amplified by rapid expansion. FIG. 16E (Engineered APCs pre-loaded with neo-antigens): APCs are engineered to induce the expression of immunostimulatory protein and are induced to present neo-antigen in the context with MHC class I and/or II via prior exposure to neo-antigens. The engineered APCs, now presenting neo-antigens, are then incubated with tumor fragments, digestions, or a plurality of cells from a tumor sample in the presence of IL2 to produce a pre-REP TIL population. These pre-REP TIL are further amplified by rapid expansion. FIG. 16F (APCs together with neo-antigens): Neo-antigen containing peptides (e.g., identified by exome and RNA comparison of tumor and control tissue and/or cells) are incubated with APCs and tumor fragments, digestions, or a plurality of cells from a tumor sample obtained from a subject in the presence of IL-2 to induce the expansion of pre-REP TILs. These pre-REP TILs are then subjected to rapid expansion. FIG. 16G (Engineered APCs together with neo-antigens): APCs are engineered for the expression of immunomodulators and co-cultured with tumor fragments, digestions, or a plurality of cells from a tumor from a subject in the presence of IL-2 and peptides composing neo-antigens to induce the expansion of pre-REP TILs. These pre-REP TILs are then subjected to rapid expansion.

FIG. 17 provides a non-limiting example of a Tandem Minigene for use in the methods described herein. In particular, this example is TMG 103. FIG. 17 discloses SEQ ID NOS 267-268, respectively, in order of appearance.

FIG. 18 provides a non-limiting example of a Tandem Minigene for use in the methods described herein. In particular, this example is TMG 106. FIG. 18 discloses SEQ ID NOS 269-270, respectively, in order of appearance.

FIG. 19 provides a non-limiting example of a Tandem Minigene for use in the methods described herein. In particular, this example is TMG 105. FIG. 19 discloses SEQ ID NOS 271-272, respectively, in order of appearance.

FIG. 20 provides a non-limiting example of a Tandem Minigene for use in the methods described herein. In particular, this example is TMG 108. FIG. 20 discloses SEQ ID NOS 271-272, respectively, in order of appearance.

FIG. 21 provides a non-limiting example of a vector encoding hIL-12 for use in the methods disclosed herein. FIG. 21 discloses SEQ ID NO: 273.

FIG. 22 provides a non-limiting example of a vector encoding hOX40L for use in the methods disclosed herein. FIG. 22 discloses SEQ ID NO: 274.

FIG. 23 provides a non-limiting example of a vector encoding h4-1BBL for use in the methods disclosed herein. FIG. 23 discloses SEQ ID NO: 275.

DETAILED DESCRIPTION

Figure 1A:
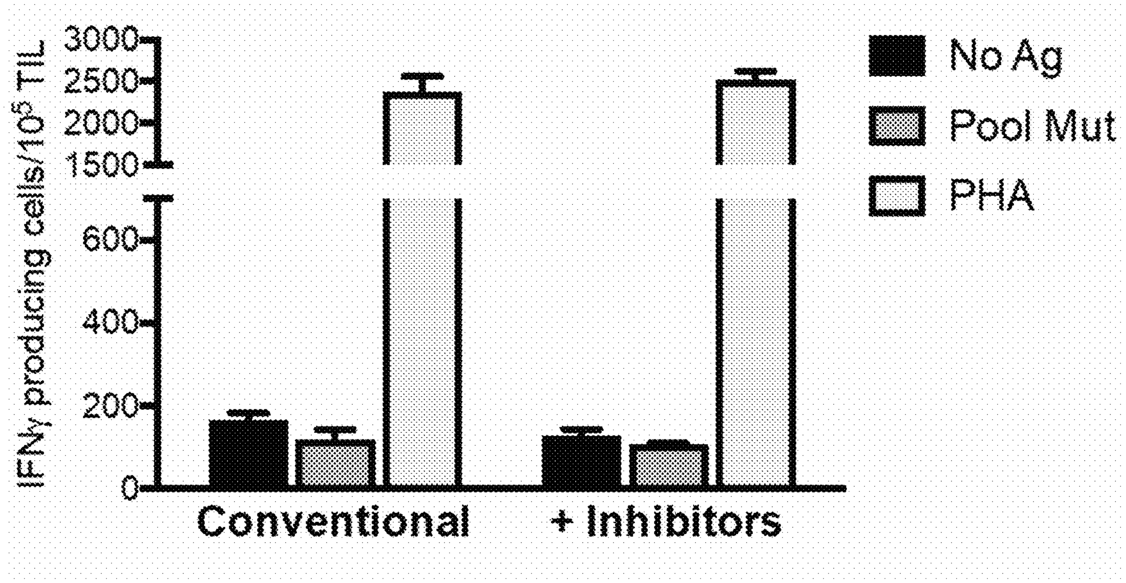
FIGS. 1A-1B show a representative example of T cell reactivity of TILs generated from ovarian tumor single cell suspension, as assessed by IFN-γ ELISpot. The following conditions were used for TIL generation: IL-2 alone (conventional) or in combination either with anti-CTLA4 (4 mAB) and anti-PD1 (10 μg/ml) inhibitors (FIG. 1A) or mutated peptides (pools of private predicted neo-antigens.

The present invention provides methods for expanding antigen-specific lymphocytes, particularly by culturing samples from subjects that contain lymphocytes or culturing lymphocytes derived therefrom in the presence of one or more peptides comprising antigen(s) and/or in the presence of an antigen presenting cell presenting the antigen(s). The methods disclosed herein produce lymphocytes capable of selectively targeting and attacking cells with said antigens on their surface.

In one aspect, the invention provides methods for expanding tumor antigen-specific lymphocytes, particularly by culturing tumor samples or lymphocytes derived therefrom in the presence of one or more peptides comprising tumor antigens and/or in the presence of an antigen presenting cell presenting tumor antigens. The methods disclosed herein produce lymphocytes capable of selectively targeting and treating tumor cells.

These methods provide many advantages. For example, the invention provides lymphocytes having antigenic specificity for an antigen (e.g., tumor antigen), including those that are unique to a patient (e.g., neo-antigen). The lymphocytes can be expanded based on their antigen specificity to provide a population of lymphocytes for the use in adoptive cell therapies such as, but not limited to, treating and/or preventing a patient's cancer. For example, these methods are advantageous when employing neo-antigens because said methods may act to expand lymphocytes that target the destruction of tumor cells while reducing or eliminating the destruction of normal, non-tumor cells. By improving personalized medicine in this way, therapeutic treatment may be more effective and less toxic to the patient.

These methods also provide the surprising advantage of improving the frequency of antigen-specific lymphocytes. This advantage stems from the addition of the peptide antigens (via soluble peptides and/or APC presentation) during the initial phase of expansion (e.g., pre-REP phase). The improved frequency of antigen-specific lymphocytes is a critical feature resulting from these methods. These methods also provide antigen-specific lymphocytes with less exhaustion as compared to methods in which the peptide antigens (via soluble peptides and/or APC presentation) are presented only during a rapid expansion phase.

Definitions

Unless defined otherwise, all technical and scientific terms used herein have the same meaning as commonly understood by one of ordinary skill in the art to which this invention belongs.

As used herein, the term "antigen" is a molecule and/or substance that can bind specifically to an antibody or generate peptide fragments that are recognized by a T cell receptor, and/or induces an immune response. An antigen may contain one or more "epitopes". In certain embodiments, the antigen has several epitopes. An epitope is recognized by an antibody or a lymphocyte in the context of an MHC molecule.

As used herein the term "tumor antigen" is broadly defined as an antigen or neo-antigen specifically expressed by a tumor or cancer cell, or associated to tumors, such as overexpressed or aberrantly expressed antigens, antigens produced by oncogenic viruses, oncofetal antigens, altered cell surface glycolipids and glycoproteins antigens, cell type-specific differentiation antigens. A tumor antigen which is present on the surface of cancer cells is an antigen which is not present on the surface of normal somatic cells of the individual i.e. the antigen is exposed to the immune system in cancer cells but not in normal somatic cells. The antigen may be expressed at the cell surface of the tumor cell where it is recognized by components of the humoral immune system such as B lymphocytes (B cells). Intracellular tumor antigens are processed into shorter peptide fragments which form complexes with major histocompatibility complex (MHC) molecules and are presented on the cell surface of cancer cells, where they are recognized by the T cell receptors (TCR's) of T lymphocytes (T cells) or natural killer cells. Preferably, the tumor antigen is one, which is not expressed by normal cells, or at least not expressed to the same level as in tumor cells.

As used herein, the term "neo-antigen" refers to a newly formed antigenic determinant that arises from a somatic mutation(s) and is recognized as "non-self". A neo-antigen can include a polypeptide sequence or a nucleotide sequence. A mutation can include a frameshift or non-frameshift indel, missense or nonsense substitution, splice site alteration (e.g., alternatively spliced transcripts), genomic rearrangement or gene fusion, or any genomic or expression alteration giving rise to a neoORF. A mutation can also include a splice variant. Post-translational modifications specific to a tumor cell can include aberrant phosphorylation. Post-translational modifications specific to a tumor cell can also include a proteasome-generated spliced antigen (see e.g., Liepe et al., A large fraction of HLA class I ligands are proteasome-generated spliced peptides; Science. 2016 Oct. 21; 354(6310):354-358, incorporated herein by reference in its entirety). A neo-antigen can include a canonical antigen. A neo-antigen can also include non-canonical antigen. Neo-antigen can be tumor-specific.

As used herein the term "coding region" is the portion(s) of a gene that encode protein.

As used herein the term "coding mutation" is a mutation occurring in a coding region.

As used herein the term "ORF" means open reading frame.

As used herein the term "NEO-ORF" is a tumor-specific ORF arising from a mutation or other aberration such as splicing.

As used herein the term "missense mutation" is a mutation causing a substitution from one amino acid to another.

As used herein the term "nonsense mutation" is a mutation causing a substitution from an amino acid to a stop codon.

As used herein the term "frameshift mutation" is a mutation causing a change in the frame of the protein.

As used herein the term "indel" is an insertion or deletion of one or more nucleic acids.

As used herein the "non-canonical antigen" is a neo-antigen that lacks canonical features. Non-limiting examples of non-canonical antigen are peptides lacking canonical anchor motifs, short peptides, 3-5-mers, long peptides (up to 18-mers), peptides using new MHC pockets, alternative anchoring amino acids, GalNAc residues acting as anchors. Non-canonical antigen can include non-synonymous somatic mutations, alternatively spliced transcripts, transcribed 5'URTs, exon-intron junctions, intronic regions, non-canonical reading frames, antisense transcripts, indels, translocations, short and novel open reading frames (ORFs), retroviral transposable elements and lncRNAs. Additional disclosure on non-canonical antigens can be found at Ronsin, C. et al. A non-AUG-defined alternative open reading frame of the intestinal carboxyl esterase mRNA generates an epitope recognized by renal cell carcinoma-reactive tumor-infiltrating lymphocytes in situ. Journal of immunology 163, 483-490 (1999); Mayrand, S. M., Schwarz, D. A. & Green, W. R. An alternative translational reading frame encodes an immunodominant retroviral CTL determinant expressed by an immunodeficiency-causing retrovirus. Journal of immunology 160, 39-50 (1998); Van Den Eynde, B. J. et al. A new antigen recognized by cytolytic T lymphocytes on a human kidney tumor results from reverse strand transcription. The Journal of experimental medicine 190, 1793-1800 (1999); Coulie, P. G. et al. A mutated intron sequence codes for an antigenic peptide recognized by cytolytic T lymphocytes on a human melanoma. Proceedings of the National Academy of Sciences of the United States of America 92, 7976-7980 (1995); Laumont, C. M. et al. Global proteogenomic analysis of human MHC class I-associated peptides derived from non-canonical reading frames. Nature communications 7, 10238, doi:10.1038/ncomms10238 (2016); Robbins, P. F. et al. The intronic region of an incompletely spliced gp100 gene transcript encodes an epitope recognized by melanoma-reactive tumor-infiltrating lymphocytes. Journal of immunology 159, 303-308 (1997); Lupetti, R. et al. Translation of a retained intron in tyrosinase-related protein (TRP) 2 mRNA generates a new cytotoxic T lymphocyte (CTL)-defined and shared human melanoma antigen not expressed in normal cells of the melanocytic lineage. The Journal of experimental medicine 188, 1005-1016 (1998); Wang, R. F., Parkhurst, M. R., Kawakami, Y., Robbins, P. F. & Rosenberg, S. A. Utilization of an alternative open reading frame of a normal gene in generating a novel human cancer antigen. The Journal of experimental medicine 183, 1131-1140 (1996); Wang, R. F. et al. A breast and melanoma-shared tumor antigen: T cell responses to antigenic peptides translated from different open reading frames. Journal of immunology 161, 3598-3606 (1998); Nakayama, M. Antigen presentation by MHC-dressed cells. Frontiers in Immunology 5, 672 (2015); and Apostolopoulos, V. Lazoura, E. Noncanonical peptides in complex with MHC class I. Expert Review Vaccines 3(2), 151-162 (2004), each of which is incorporated herein in their entirety for all intended purposes.

The terms "first expansion", "pre-rapid expansion protocol", or "pre-REP" are used herein interchangeably and refer to a procedure wherein lymphocytes (e.g., derived from a sample for a subject, such as but not limited to, a blood sample, tissue, tumor fragments, or enzymatically digested tissue, dissociated/suspended tumor cells, a lymph node sample, or a bodily fluid sample) are initially expanded over a period of time in culture media supplemented with a compound that ensures continued lymphocyte division and survival during the initial expansion phase. In certain embodiments, the compound used during the pre-REP phase can be, but is not limited to, interleukin-2 (IL-2), interleukin-4 (IL-4), interleukin-7 (IL-7), interleukin-15 (IL-15), interleukin-17 (IL-17), interleukin-21 (IL-21), or any combination thereof. In certain embodiments, the compound used during the pre-REP phase can be IL-2. In certain embodiments, the pre-REP procedure takes place in conditions that favor the growth and/or expansion of lymphocytes over tumor and other non-lymphocyte cells. In certain embodiments, the pre-REP procedure occurs in a period of time that lasts between about 3 to about 45 days, about 5 to about 40 days, or about 11 to about 35 days.

The terms "second expansion", "rapid expansion protocol", or "REP" are used herein interchangeably and refer to a procedure that occurs after the pre-REP procedure wherein the lymphocytes (e.g., derived from a sample for a subject, such as but not limited to, a blood sample, tissue, tumor fragments, or enzymatically digested tissue or tumor cell suspension) are expanded in number by at least about 3-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold. "REP" can involve activating pre-REP lymphocytes through the CD3 complex (e.g., use of an anti-CD3 mAb) and/or activation by feeder cells (e.g., peripheral blood mononuclear cells ("PBMC") feeder cells), obtained from the subject or a normal healthy donor. In certain embodiments, the feeder cells are irradiated (e.g., 5,000 cGy). In certain embodiments, the pre-REP lymphocytes are present at a ratio of 200:1 to that of the irradiated feeder cells (e.g., PMBCs). In certain embodiments, IL-2, IL-4, IL-7, IL-15, IL-17, IL-21, or a combination thereof, is added to drive rapid cell division in the activated lymphocytes. In certain embodiments, IL-2 is added to drive rapid cell division in the activated lymphocytes. In certain embodiments, the lymphocytes are then expanded for another 12 days and diluted as needed with 1:1 culture medium with IL-2. For examples of rapid expansion and other methods, see U.S. Pat. No. 8,287,857, which is incorporated herein in its entirety for all purposes.

As used herein, the terms "antibody" and "antibodies" refer to polyclonal antibodies, monoclonal antibodies, multispecific antibodies, human antibodies, humanized antibodies, chimeric antibodies, and antibody fragments (e.g., single chain antibodies, Fab fragments, Fv fragments, single-chain Fv fragments (scFv), a divalent antibody fragment such as an (Fab)2'-fragment, F(ab') fragments, disulfide-linked Fvs (sdFv), intrabodies, minibodies, diabodies, triabodies, decabodies, and other domain antibodies (e.g., Holt, L. J., et al., Trends Biotechnol. (2003), 21, 11, 484-490)). The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful in the methods described herein include immunoglobulin molecules of any type (e.g., IgG, IgE, IgM, IgD, IgA and IgY), class (e.g., IgG1, IgG2, IgG3, IgG4, IgA1, and IgA2) or subclass.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The technology illustratively described herein suitably may be practiced in the absence of any element(s) not specifically disclosed herein. Thus, for example, in each instance herein any of the terms "comprising," "consisting essentially of" and "consisting of" may be replaced with either of the other two terms. By "consists essentially of" in the context of gene encoding a peptide is meant that the gene may further include additional nucleotides or regions such as, for example, those that do not modify the encoded peptide but allow for the peptide to be expressed (e.g., promoters, enhances, linkers).

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

Methods of Expanding Antigen-Specific Lymphocytes

In one aspect, described herein are methods for expanding antigen-specific lymphocytes ex vivo comprising expanding lymphocytes in a sample obtained from a subject or lymphocytes isolated from such sample, wherein expanding comprises adding one or more peptides during expansion, wherein each of said peptide(s) comprises a different antigen and wherein antigen-specific lymphocytes are expanded. In certain embodiments, the methods comprise adding two or more peptide(s) (i.e., a pool of different peptides). In certain embodiments, if only one phase of expansion is conducted, the phase of expansion is a pre-rapid expansion protocol (pre-REP). In certain embodiments, the antigen-specific lymphocytes are preferentially expanded over other lymphocytes present during the expansion. In certain embodiments, this preferential expansion results in an enrichment of antigen-specific lymphocytes.

In one aspect, described herein are methods for expansion of antigen-specific lymphocytes ex vivo comprising a) expanding lymphocytes in a sample obtained from a subject or lymphocytes isolated from such sample, wherein expanding comprises at least two phases of expansion, and b) adding one or more peptides during at least one of the at least two phases of expansion, wherein each of said peptide(s) comprises a different antigen and wherein antigen-specific lymphocytes are expanded. In certain embodiments, the methods comprise adding two or more peptide(s) (i.e., a pool of peptides). In certain embodiments, the antigen-specific lymphocytes are preferentially expanded over other lymphocytes present during the expansion. In certain embodiments, this preferential expansion results in an enrichment of antigen-specific lymphocytes.

Lymphocyte production is commonly conducted using a 2-step process: 1) the pre-REP stage where you the grow the cells in standard lab media such as RPMI and treat the lymphocytes with reagents to grow and maintain viability of the lymphocytes; and 2) the REP stage is where lymphocytes are expanded in a large enough culture amount for treating the subject. In certain embodiments, the compounds disclosed herein for the different phases of production can be included in the culture medium during the respective phase.

In certain embodiments, the at least two phases of expansion of the methods disclosed herein comprises a first expansion (i.e., pre-REP) and a second expansion (i.e., REP). In certain embodiments, the first and/or second expansion phases are repeated more than once. In certain embodiments, additional expansion phases are added to allow for more effective therapeutic antigen-specific lymphocyte (e.g., less exhaustion).

In certain embodiments, the first expansion refers to a procedure wherein lymphocytes (e.g., derived from a sample for a subject containing lymphocytes, such as but not limited to, a tissue, bone marrow, thymus, tumor fragments, or enzymatically digested tissue, dissociated/suspended cells, a lymph node sample, or a bodily fluid sample (e.g., blood, ascites, lymph) are initially expanded over a period of time in culture media supplemented with a compound that ensures continued lymphocyte division and survival during the expansion phase. When conducted in this manner, the first expansion is a pre-rapid expansion protocol (pre-REP). The conditions by which the pre-REP phase for the methods as disclosed herein can be conducted are well known to those of skill in the art.

In certain embodiments, the first expansion (e.g., pre-REP) phase comprises expanding the lymphocytes in the presence of at least one expansion-promoting agent. In certain embodiments, a cytokine used during the first expansion (e.g., pre-REP) to promote lymphocyte growth can be, but is not limited to, interleukin-2 (IL-2), interleukin-4 (IL-4), interleukin-6 (IL-6), interleukin-7 (IL-7), interleukin-9 (IL-9), interleukin-11 (IL-11), interleukin-12 (IL-12), interleukin-15 (IL-15), interleukin-17 (IL-17), interleukin-21 (IL-21), or any combination thereof. In certain embodiments, the compound used during first expansion (e.g., pre-REP) is the cytokine IL-2.

In certain embodiments, the compound used during the first expansion (e.g., pre-REP) phase can be a cytokine present at a concentration from about 100 IU/ml to about 10,000 IU/ml. In certain embodiments, the cytokine can be present in the cell culture medium from about 200 IU/ml to about 9,500 IU/ml, about 400 IU/ml to about 9,000 IU/ml, about 600 IU/ml to about 8,500 IU/ml, about 800 IU/ml to about 8,000 IU/ml, about 1,000 IU/ml to about 7,500 IU/ml, about 2,000 IU/ml to about 7,000 IU/ml, about 3,000 IU/ml to about 6,750 IU/ml, about 4,000 IU/ml to about 6,500 IU/ml, about 5,000 IU/ml to about 6,250 IU/ml, or about 5,500 IU/ml to about 6,000 IU/ml. In certain embodiments, the cytokine can be present in the cell culture medium from about 1,000 IU/ml to about 10,000 IU/ml, about 2,000 IU/ml to about 9,000 IU/ml, about 3,000 IU/ml to about 8,000 IU/ml, about 4,000 IU/ml to about 7,000 IU/ml, or about 5,000 IU/ml to about 6,000 IU/ml. In certain embodiments, the cytokine used during the first expansion (e.g., pre-REP) phase is present in the cell culture medium at about 6,000 IU/ml. In certain embodiments, the cytokine can be, but is not limited to, IL-2, IL-4, IL-6, IL-7, IL-9, IL-11, IL-12, IL-15, IL-17, IL-21, or any combination thereof. In certain embodiments, the cytokine is IL-2. In certain embodiments, the cytokine present during the first expansion (e.g., pre-REP) phase is IL-2 at a concentration of about 6,000 IU/ml.

Additional compounds that can be present during the first expansion (e.g., pre-REP) phase include, but are not limited to, small molecule (e.g., small organic molecule), nucleic acid, polypeptide, or a fragment, isoform, variant, analog, or derivative thereof antagonists against PD-1, CTLA-4, 4-1BB, LAG-3, TIM-3, 2B4/CD244/SLAMF4, CD160, TIGIT, TCF1, CD39, or BATF. In certain embodiments, the antagonist can be a polypeptide. In certain embodiments, the antagonist can be an antibody or fragment thereof. In certain embodiments, the antibody is a monoclonal antibody. In certain embodiments, the additional compound can be a checkpoint blockade modulator.

In certain embodiments, the first expansion (e.g., pre-REP) procedure takes place in conditions that favor the growth and/or expansion of lymphocytes over sample and other non-lymphocyte cells.

In certain embodiments, the first expansion (e.g., pre-REP) procedure occurs in a period of time that lasts between about 3 to about 45 days, about 5 to about 40 days, or about 11 to about 35 days.

In certain embodiments, the first expansion (e.g., pre-REP) comprises expanding the lymphocytes under conditions that results about a 1.5-fold to about a 1000-fold increase in the number of antigen-specific lymphocytes (e.g., over a period of one to two weeks) as compared to expanding the lymphocytes without adding the peptide(s). In certain embodiments, the first expansion (e.g., pre-REP) comprises expanding the lymphocytes under conditions that results in no less than about a 1.5-fold increase in the number of lymphocytes over a period of a week as compared to expanding the lymphocytes without adding the peptide(s). In certain embodiments, the first expansion (e.g., pre-REP)

comprises expanding the lymphocytes under conditions that results in no less than about a 2-fold increase in the number of lymphocytes over a period of a week as compared to expanding the lymphocytes without adding the peptide(s). In certain embodiments, the first expansion (e.g., pre-REP) comprises expanding the lymphocytes under conditions that results in about a 1.5- to about a 2-fold increase in the number of lymphocytes over a period of a week as compared to expanding the lymphocytes without adding the peptide(s). In certain embodiments, the first expansion (e.g., pre-REP) comprises expanding the lymphocytes under conditions that results in a greater than 1.5-fold increase in the number of lymphocytes over a period of a week as compared to expanding the lymphocytes without adding the peptide(s). In certain embodiments, the first expansion (e.g., pre-REP) comprises an up to 1,000-fold enrichment in the frequency of antigen-specific T cells (see, e.g., FIG. 15). In certain embodiments, the up to 1,000-fold enrichment in the frequency is achieved in two-weeks. The fold enrichment is determined by comparing the frequencies of antigen-specific lymphocytes obtained with conventional versus exposure to the peptide antigens during the first phase of expansion. In certain embodiments, the first expansion results in a about 1.5, about 2, about 3, about 4, about 5, about 6, about 7, about 8, about 9, about 10, about 15, about 20, about 30, about 40, about 50, about 60, about 70, about 80, about 90, about 100, about 200, about 300, about 400, about 500, about 600, about 700, about 800, about 900, or about 1000-enrichment in antigen-specific lymphocytes as compared to a method in which the peptide(s) are not present during the pre-REP phase.

The conditions by which the second expansion (e.g., REP) phase for the methods as disclosed herein can be conducted are well known to those of skill in the art.

In certain embodiments, the second expansion refers to a procedure wherein lymphocytes (e.g., derived from a sample taken from a population of lymphocytes following a pre-REP phase) are initially expanded over a period of time in culture media supplemented with a compound(s) that ensures rapid lymphocyte division during the expansion phase. When conducted in this manner, the second expansion is a rapid expansion protocol (REP). In certain embodiments, the REP stage requires cGMP grade reagents and 30-40L of culture medium. The conditions by which the REP phase for the methods as disclosed herein can be conducted are well known to those of skill in the art.

In certain embodiments, the second expansion (e.g., REP) is conducted in the presence of CD3 complex agonist, mitogens, and/or feeder cells.

In certain embodiments, the CD3 complex agonists can be, but is not limited to, a compound, small molecule (e.g., small organic molecule), nucleic acid, polypeptide, or a fragment, isoform, variant, analog, or derivative thereof. In certain embodiments, the CD3 complex agonist is a polypeptide. In certain embodiments, the CD3 complex agonist is an antibody or fragment thereof. In certain embodiments, the CD3 complex agonist is a monoclonal antibody. In certain embodiments, the CD3 complex agonist OKT-3 (e.g., at 30 ng/ml). In certain embodiments, the CD3 complex agonist is added in combination with an anti-CD28 antibody.

In certain embodiments, mitogens include, but are not limited to, phytohemagglutinin (PHA), concanavalin A (Con A), pokeweed mitogen (PWM), mezerein (Mzn), and tetradecanoyl phorbol acetate (TPA).

Feeder cells encompass cells that are capable of supporting the expansion of lymphocytes cells or descendants thereof. The support which the feeder cells provide may be characterized as both contact-dependent and non-contact-dependent. The feeder cells may secrete or express on the cell surface factors which support the expansion of the progenitor cells. One example of feeder cells is peripheral blood mononuclear cells (PBMC). Other non-limiting examples include splenocytes, lymph node cells and dendritic cells. Feeder cells also may be cells that would not ordinarily function as feeder cells, such as fibroblasts, which have been engineered to secrete or express on their cell surface the factors necessary for support of T cell progenitor cell expansion. Feeder cells may be autologous, allogeneic, syngeneic, artificial, or xenogeneic with respect to the lymphocytes and/or subject.

Feeder cells are made non-mitotic by procedures standard in the tissue culture art. Examples of such methods are irradiation of feeder cells with a gamma-ray source or incubation of feeder cells with mitomycin C for a sufficient amount of time to render the cells mitotically inactive.

In certain embodiments, a cytokine used during the second expansion (e.g., REP) to promote lymphocyte growth can be, but is not limited to, IL-2, IL-4, IL-6, IL-7, IL-9, IL-11, IL-12, IL-15, IL-17, and IL-21, or a combination thereof. In certain embodiments, a compound used during REP is IL-2.

A non-limiting example of rapid expansion includes expanding a pool of cells (e.g., $1\times10^6$ pre-REP lymphocytes) in the presence of OKT-3 antibody with IL2 (3,000 IU/ml) and allogenic feeder cells (e.g., from three different donors) at a ratio of 100:1.

In certain embodiments, a cytokine used during the second expansion (e.g., REP) can be present in the cell culture medium (at least at the time the cells are initially added) from about 50 IU/ml to about 10,000 IU/ml. In certain embodiments, the compound can be present in the cell culture medium from about 100 IU/ml to about 9,000 IU/ml, about 200 IU/ml to about 8,000 IU/ml, about 400 IU/ml to about 7,000 IU/ml, about 600 IU/ml to about 6,000 IU/ml, about 800 IU/ml to about 5,000 IU/ml, about 1,000 IU/ml to about 4,000 IU/ml, or about 2,000 IU/ml to about 3,000 IU/ml. In certain embodiments, the compound can be present in the cell culture medium from about 500 IU/ml to about 6,000 IU/ml, about 1,000 IU/ml to about 5,000 IU/ml, or about 2,000 IU/ml to about 4,000 IU/ml. In certain embodiments, the cytokine used during the second expansion (e.g., REP) is present in the cell culture medium at about 3,000 IU/ml. In certain embodiments, the cytokine can be, but is not limited to, IL-2, IL-4, IL-6, IL-7, IL-9, IL-11, IL-12, IL-15, IL-17, IL-21, or any combination thereof. In certain embodiments, the cytokine is IL-2. In certain embodiments, the cytokine present during the second expansion (e.g., REP) is IL-2 at a concentration of about 3,000 IU/ml.

Additional compounds that can be present during the second expansion (e.g., REP) phase include, but are not limited to, small molecule (e.g., small organic molecule), nucleic acid, polypeptide, or a fragment, isoform, variant, analog, or derivative thereof antagonists against PD-1, CTLA-4, 4-1BB, LAG-3, TIM-3, 2B4/CD244/SLAMF4, CD160, TIGIT, TCF1, CD39, or BATF. In certain embodiments, the antagonist can be a polypeptide. In certain embodiments, the antagonist can be an antibody or fragment thereof. In certain embodiments, the antibody is a monoclonal antibody. In certain embodiments, the additional compound can be a checkpoint inhibitor.

In certain embodiments, the second expansion (e.g., REP) procedure takes place in conditions that favor the growth and/or expansion of lymphocytes over sample and other non-lymphocyte cells.

In certain embodiments, the second expansion (e.g., REP) procedure occurs in a period of time that lasts between about 5 to about 42 days. In certain embodiments, the second expansion occurs between about 7 to about 35 days, about 10 to about 28 days, or about 14 to about 21 days. In certain embodiments, the second expansion is about 10 days long. In certain embodiments, the second expansion is about 11 days long. In certain embodiments, the second expansion is about 14 days long.

Agents that can be used for the expansion of T cells can include interleukins, such as IL-2, IL-7, IL-15, or IL-21 (see for example Cornish et al. 2006, Blood. 108(2):600-8, Bazdar and Sieg, 2007, Journal of Virology, 2007, 81(22): 12670-12674, Battalia et al, 2013, Immunology, 139(1):109-120). Other illustrative examples for agents that may be used for the expansion of T cells are agents that bind to CD8, CD45 or CD90, such as αCD8, αCD45 or αCD90 antibodies. Illustrative examples of T cell population including antigen-specific T cells, T helper cells, cytotoxic T cells, memory T cell (an illustrative example of memory T cells are CD62L|CD8| specific central memory T cells) or regulatory T cells (an illustrative example of Treg are CD4+ CD25+CD45RA+ Treg cells). Additional agents that can be used to expand T lymphocytes includes methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

Agents that can be used for the expansion of natural killer cells can include agents that bind to CD16 or CD56, such as for example aCD16 or aCD56 antibodies. In certain embodiments, the binding agent includes antibodies (see for example Hoshino et al, Blood. 1991 Dec. 15; 78(12):3232-40). Other agents that may be used for expansion of NK cells may be IL-15 (see for example Vitale et al. 2002. The Anatomical Record. 266:87-92).

In certain embodiments, the second expansion comprises expanding the lymphocytes under conditions that results in about a 1.5-fold to at least about a 100-fold increase in the number of antigen-specific lymphocytes over a period of a week as compared to expanding the lymphocytes without adding the peptide(s). In certain embodiments, the second expansion comprises expanding the lymphocytes under conditions that results in about a 3-fold to at least about a 100-fold increase in the number of antigen-specific lymphocytes over a period of a week as compared to expanding the lymphocytes without adding the peptide(s).

The methods disclosed herein may comprise adding one or more peptide(s). In certain embodiments, the methods comprise adding a pool of peptides (i.e., two or more different peptides). In certain embodiments, the methods only add a single peptide comprising the antigen. In certain embodiments, the methods comprise adding about 2 to about 300 different peptides. In certain embodiments, the methods comprising adding about 2 to about 100, about 20 to about 100, about 50 to about 100, about 2 to about 10 or 2 to about 5 different peptides. In certain embodiments, the methods comprising adding about 5 different peptides.

In certain embodiments, the methods comprise adding at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 different peptides. In certain embodiments, the methods add at least about 2 to about 100, about 2 to about 50, about 2 to about 40, about 2 to about 30, about 2 to about, 20, about 2 to about 15, about 2 to about 10, about 2 to about 9, about 2 to about 8, about 2 to about 7, about 2 to about 6, about 2 to about 5, about 2 to about 4, or about 2 to about 3 different peptides. In certain embodiments, the methods add about 20 to about 300, about 20 to about 200, about 20 to about 100, about 20 to about 90, about 20 to about 80, about 20 to about 70, about 20 to about 60, about 20 to about 50, about 20 to about 40, or about 20 to about 30 different peptides. In certain embodiments, the methods add about 10 to about 100, about 20 to about 100, about 30 to about 100, about 40 to about 100, about 50 to about 100, about 60 to about 100, about 70 to about 100, about 80 to about 100 or about 90 to about 100 different peptides In certain embodiments, the methods comprise adding during at least one of the at least two phases of expansion, wherein each of said peptide(s) comprises a different antigen if there is more than one type of peptide. In certain embodiments, the peptide(s) are only added during the first expansion (e.g., pre-REP). In certain embodiments, the peptide(s) are only added during the second expansion (e.g., REP). In certain embodiments, the peptide(s) are added during both the first expansion (e.g., pre-REP) and second expansion (e.g., REP).

In certain embodiments, the methods comprise adding the peptide(s) at the initiation of at least one of the at least two phases of expansion. In certain embodiments, the peptide(s) are added at the initiation of the first expansion (e.g., pre-REP). In certain embodiments, the peptide(s) are added at the initiation of the second expansion (e.g., REP). In certain embodiments, the peptide(s) are added at the initiation of only the first expansion (e.g., pre-REP). In certain embodiments, the peptide(s) are added at the initiation of both the first expansion (e.g., pre-REP) and second expansion (e.g., REP).

In certain embodiments, the methods comprise re-adding the peptide(s) at least once. In certain embodiments, the peptide(s) are only re-added during the first expansion (e.g., pre-REP). In certain embodiments, the peptide(s) are only re-added during the second expansion (e.g., REP). In certain embodiments, the peptide(s) are only re-added during both the first expansion (e.g., pre-REP) and second expansion (e.g., REP).

In certain embodiments, the methods comprise re-adding the peptide(s) within the respective expansion phase every day after the first addition. In certain embodiments, the peptide(s) may be re-added in the respective expansion phase every day after the first addition for at least 1, at least 2, at least 3, at least 4, at least, 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, or at least 50 days. In certain embodiments, the peptide(s) may be re-added in the respective expansion phase every day after the first addition for about 1, about 2, about 3, about 4, about, 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, or about 50 days. In certain embodiments, the peptide(s) are re-added at least once after the first addition within the respective expansion phase. In certain embodiments, the peptide(s) are re-added once after the first addition within the respective expansion phase. In certain embodiments, the peptide(s) are re-added for at least two days after the first addition within the respective expansion phase. In certain embodiments, the peptide(s) are re-added for two days after the first addition within the respective expansion phase.

In certain embodiments, the methods comprise re-adding the peptide(s) within the respective expansion phase every other day after the first addition. In certain embodiments, the peptide(s) may be re-added in the respective expansion phase every other day after the first addition for at least 1, at least 2, at least 3, at least 4, at least, 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, or at least 50 times. In certain embodiments, the peptide(s) may be re-added in the respective expansion phase every other day after the first addition for about 1, about 2, about 3, about 4, about, 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, or about 50 times. In certain embodiments, the peptide(s) are re-added at least once after the first addition within the respective expansion phase. In certain embodiments, the peptide(s) are re-added one time after the first addition within the respective expansion phase. In certain embodiments, the peptide(s) are re-added for at least two times after the first addition within the respective expansion phase. In certain embodiments, the peptide(s) are re-added for two times after the first addition within the respective expansion phase.

In certain embodiments, the methods comprise re-adding the peptide(s) within the respective expansion phase every third, fourth, fifth, sixth, seventh, eighth, ninth, or tenth day after the first addition. In certain embodiments, the peptide(s) within the respective expansion phase may be added every third, fourth, fifth, sixth, or seventh day after the first addition for at least 1, at least 2, at least 3, at least 4, at least, 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, or at least 50 times. In certain embodiments, the peptides are added every third, fourth, fifth, sixth, or seventh day after the first addition for about 1, about 2, about 3, about 4, about, 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, or about 50 times. In certain embodiments, the peptide(s) are re-added at least once after the first addition within the respective expansion phase. In certain embodiments, the peptide(s) are re-added one time after the first addition within the respective expansion phase. In certain embodiments, the peptide(s) are re-added for at least two times after the first addition within the respective expansion phase. In certain embodiments, the peptide(s) are re-added for two times after the first addition within the respective expansion phase.

In certain embodiments, the peptide(s) can be added only on the first day of the expansion phase. In certain embodiments, the peptide(s) are added on the first and third day of the expansion phase. In certain embodiments, the peptide(s) are added on the first, third and fifth day of expansion. In certain embodiments, the peptide(s) are added on the first and tenth day of expansion.

The peptide(s) can be added in soluble form or presented on the surface of an antigen presenting cell (APC) engineered to present the peptide(s) on its surface. In certain embodiments, the peptides can be added in both the soluble form and presented on the surface of an APC. In certain embodiments, the APCs are treated such that they present the peptide(s) on their surface prior to being added/co-cultured with the lymphocytes. In certain embodiments, the peptide(s) are added in soluble form together with APCs that have not been pre-treated to present the peptide(s) on their surface prior to being added/co-cultured with the lymphocytes. In certain embodiments, the peptide(s) are added in soluble form together with APCs that have and APCs that have not been pre-treated to present the peptide(s) on their surface prior to being added/co-cultured with the lymphocytes.

If added in a soluble form, the peptide(s) may be added at a concentration from about 0.1 nM to about 100 μM for each peptide. In certain embodiments, the soluble peptide(s) may be added at a concentration of about 1 nM to about 90 μM, about 10 nM to about 80 μM, about 50 nM to about 70 μM, about 100 nM to about 60 μM, about 150 nM to about 50 μM, about 200 nM to about 40 μM, about 250 nM to about 30 μM, about 300 nM to about 20 μM, about 350 nM to about 10 μM, about 400 nM to about 9 μM, about 450 nM to about 8 μM, about 500 nM to about 7 μM, about 550 nM to about 6 μM, about 600 nM to about 5 μM, about 650 nM to about 4 μM, about 700 nM to about 3 μM, about 750 nM to about 2.5 μM, about 800 nM to about 2 μM, about 900 nM to about 1.5 μM, or about 950 nM to about 1.25 μM for each peptide. In certain embodiments, the soluble peptide(s) may be added at a concentration of about 100 nM to about 100 μM, about 250 nM to about 75 μM, about 500 nM to about 50 μM, about 750 nM to about 25 μM, about 900 nM to about 10 μM or about 990 nM to about 5 μM for each peptide.

In certain embodiments, the soluble peptide(s) may be added at a concentration of at least about 0.1 nM, about 1 nM, about 5 nM, about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 260 nM, about 270 nM, about 280 nM, about 290 nM, about 300 nM, about 310 nM, about 320 nM, about 330 nM, about 340 nM, about 350 nM, about 360 nM, about 370 nM, about 380 nM, about 390 nM, about 400 nM, about 410 nM, about 420 nM, about 430 nM, about 440 nM, about 450 nM, about 460 nM, about 470 nM, about 480 nM, about 490 nM, about 500 nM, about 510 nM, about 520 nM, about 530 nM, about 540 nM, about 550 nM, about 560 nM, about 570 nM, about 580 nM, about 590 nM, about 600 nM, about 610 nM, about 620 nM, about 630 nM, about 640 nM, about 650 nM, about 660 nM, about 670 nM, about 680 nM, about 690 nM, about 700 nM, about 710 nM, about 720 nM, about 730 nM, about 740 nM, about 750 nM, about 760 nM, about 770 nM, about 780 nM, about 790 nM, about 800 nM, about 810 nM, about 820 nM, about 830 nM, about 840 nM, about 850 nM, about 860 nM, about 870 nM, about 880 nM, about 890 nM, about 900 nM, about 910 nM, about 920 nM, about 930 nM, about 940 nM, about 950 nM, about 960 nM, about 970 nM, about 980 nM, about 990 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, or about 100 µM for each peptide.

In certain embodiments, the soluble peptide(s) may be added at a concentration of about 0.1 nM, about 1 nM, about 5 nM, about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 260 nM, about 270 nM, about 280 nM, about 290 nM, about 300 nM, about 310 nM, about 320 nM, about 330 nM, about 340 nM, about 350 nM, about 360 nM, about 370 nM, about 380 nM, about 390 nM, about 400 nM, about 410 nM, about 420 nM, about 430 nM, about 440 nM, about 450 nM, about 460 nM, about 470 nM, about 480 nM, about 490 nM, about 500 nM, about 510 nM, about 520 nM, about 530 nM, about 540 nM, about 550 nM, about 560 nM, about 570 nM, about 580 nM, about 590 nM, about 600 nM, about 610 nM, about 620 nM, about 630 nM, about 640 nM, about 650 nM, about 660 nM, about 670 nM, about 680 nM, about 690 nM, about 700 nM, about 710 nM, about 720 nM, about 730 nM, about 740 nM, about 750 nM, about 760 nM, about 770 nM, about 780 nM, about 790 nM, about 800 nM, about 810 nM, about 820 nM, about 830 nM, about 840 nM, about 850 nM, about 860 nM, about 870 nM, about 880 nM, about 890 nM, about 900 nM, about 910 nM, about 920 nM, about 930 nM, about 940 nM, about 950 nM, about 960 nM, about 970 nM, about 980 nM, about 990 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, or about 100 µM for each peptide. In certain embodiments, the soluble peptide(s) may be added at a concentration of about 1 µM for each peptide.

If the lymphocytes are exposed to the peptide(s) via being presented by an APC, the ratio of cells in the sample (e.g., tumor sample) to APC presenting the peptide(s) is about 1:1 to about 1:100. In certain embodiments, the ratio of cells in the sample to APC presenting peptide(s) is about 1:1 to about 1:90; about 1:1 to about 1:80, about 1:1 to about 1:70, about 1:1 to about 1:60, about 1:1 to about 1:50, about 1:1 to about 1:40, about 1:1 to about 1:30, about 1:1 to about 1:20, about 1:1 to about 1:10, about 1:1 to about 1:9, about 1:1 to about 1:8, about 1:1 to about 1:7, about 1:1 to about 1:6, about 1:1 to about 1:5, about 1:1 to about 1:4, about 1:1 to about 1:3, or about 1:1 to about 1:2. In certain embodiments, the ratio of cells in the sample to APC presenting peptide(s) is about 1:2 to about 1:90; about 1:3 to about 1:80, about 1:4 to about 1:70, about 1:5 to about 1:60, about 1:6 to about 1:50, about 1:7 to about 1:40, about 1:8 to about 1:30, or about 1:9 to about 1:20.

In certain embodiments, the ratio of cells in the sample to APC presenting peptide(s) is at least about 1:2, about 1:3, about 1:4, about 1:5, about 1:6, about 1:7, about 1:8, or about 1:9, or about 1:10, or about 1:12, or about 1:14, or about 1:16, or about 1:18, or about 1:20, or about 1:25, or about 1:30, or about 1:35, or about 1:40, or about 1:45, or about 1:50, or about 1:55, or about 1:60, or about 1:65, or about 1:70, or about 1:75, or about 1:80, or about 1:85, or about 1:90, or about 1:100.

In certain embodiments, the ratio of cells in the sample to APC presenting peptide(s) is about 1:2, about 1:3, about 1:4, about 1:5, about 1:6, about 1:7, about 1:8, or about 1:9, or about 1:10, or about 1:12, or about 1:14, or about 1:16, or about 1:18, or about 1:20, or about 1:25, or about 1:30, or about 1:35, or about 1:40, or about 1:45, or about 1:50, or about 1:55, or about 1:60, or about 1:65, or about 1:70, or about 1:75, or about 1:80, or about 1:85, or about 1:90, or about 1:100.

If the lymphocytes are exposed to the peptide(s) via being presented by an APC, the ratio of lymphocytes in the sample to APC presenting the peptide(s) is about 0.01:1 to about 100:1. In certain embodiments, the ratio of lymphocytes in the sample to APC presenting the peptide(s) is about 0.025:1 to about 90:1, about 0.05:1 to about 80:1, about 0.075:1 to about 70:1, about 0.1:1 to about 60:1, about 0.125:1 to about 50:1, about 0.15:1 to about 40:1, about 0.175:1 to about 30:1, about 0.2:1 to about 20:1, about 0.3:1 to about 10:1, about 0.4:1 to about 9:1, about 0.5:1 to about 8:1, about 0.6:1, about 7:1, about 0.7:1, about 6:1, about 0.7:1 to about 5:1, about 0.8:1 to about 4:1, about 0.9:1 to about 3:1. In certain embodiments, the lymphocytes are isolated from the sample.

In certain embodiments, the ratio of lymphocytes in the sample to APC presenting the peptide(s) is at least about 0.01:1, about 0.02:1, about 0.04:1, about 0.06:1, about 0.08:1, about 0.09:1, about 0.1:1, about 0.2:1, about 0.3:1, about 0.4:1, about 0.5:1, about 0.6:1, about 0.7:1, about 0.8:1, about 0.9:1, about 1:1, about 2:1, about 3:1, about 4:1, about 5:1, about 6:1, about 7:1, about 8:1, about 9:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 90:1, about 100:1. In certain embodiments, the lymphocytes are isolated from the sample.

In certain embodiments, the ratio of lymphocytes in the sample to APC presenting the peptide(s) is at about 0.01:1, about 0.02:1, about 0.04:1, about 0.06:1, about 0.08:1, about 0.09:1, about 0.1:1, about 0.2:1, about 0.3:1, about 0.4:1, about 0.5:1, about 0.6:1, about 0.7:1, about 0.8:1, about 0.9:1, about 1:1, about 2:1, about 3:1, about 4:1, about 5:1, about 6:1, about 7:1, about 8:1, about 9:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 90:1, about 100:1. In certain embodiments, the lymphocytes are isolated from the sample.

In certain embodiments, exposure to the peptide(s) during the first expansion (e.g., pre-REP) results in antigen-specific lymphocytes with less exhaustion as compared to antigen-specific lymphocytes exposed to the peptide(s) in only the second expansion (e.g., REP).

In certain embodiments, exposure to the peptide(s) during the first expansion (e.g., pre-REP) but not the second expansion results in antigen-specific lymphocytes with less exhaustion as compared antigen-specific lymphocytes exposed to the peptide(s) in the first (e.g., pre-REP) and second expansion (e.g., REP).

In certain embodiments, exposure to the peptide(s) during the first expansion (e.g., pre-REP) but not the second expansion (e.g., REP) results in antigen-specific lymphocytes with less exhaustion as compared antigen-specific lymphocytes exposed to the peptide(s) only in the second expansion.

In certain embodiments of the methods disclosed herein, exposure to the peptide(s) during the first expansion results in an improvement in the frequency of the lymphocytes. In certain embodiments, exposure to the peptide(s) during the first expansion results in an improvement in the frequency of antigen-specific lymphocytes. In certain embodiments, the improvement in frequency of lymphocytes and/or antigen-specific lymphocytes is over methods in which lymphocytes are not exposed to peptide(s) during the first expansion.

In certain embodiments, the antigen-specific lymphocytes are not selected and/or isolated before co-culturing with the peptide(s) and/or APC's presenting peptides. In certain embodiments, the antigen-specific lymphocytes are not selected and/or isolated after co-culturing with the peptide(s) and/or APC's presenting peptides. In certain embodiments, the methods disclosed herein are not used to identify antigen-specific lymphocytes either in culture or within a tissue sample. In certain embodiments, the APC's presenting peptides are not used to identify antigen-specific lymphocytes. In certain embodiments, the methods disclosed herein are not used to determine whether a lymphocyte recognizes a certain antigen or epitope.

Peptide(s)

In one aspect, described herein are methods for expanding antigen-specific lymphocytes ex vivo comprising expanding lymphocytes in a sample obtained from a subject or lymphocytes isolated from such sample, wherein expanding comprises adding one or more peptides during expansion, wherein each of said peptide(s) comprises a different antigen and wherein antigen-specific lymphocytes are expanded. In certain embodiments, the methods comprise adding two or more peptide(s) (i.e., a pool of different peptides). In certain embodiments, the peptide(s) are added in soluble form. In certain embodiments, the peptide(s) are presented on the surface of an antigen presenting cell (APC). In certain embodiments, the APCs are incubated with soluble peptide(s), which leads to the APC presenting peptide(s) on its surface (e.g., either directly binding to an MHC on its surface or by being processed by the APC). In certain embodiments, the APCs are engineered to express the peptide(s) (e.g., via translation or transduction). In certain embodiments, the peptide(s) being added are both soluble peptide(s) together with peptide(s) presented on the surface of an APC (e.g., engineered to express the peptide(s), pre-incubated with the peptide(s), or both). In certain embodiments, soluble peptide(s) are added along with APCs that have not been previously induced to present the peptide(s) on its surface prior to being co-cultured with the lymphocytes.

In one aspect, described herein are methods for expansion of antigen-specific lymphocytes ex vivo comprising a) expanding lymphocytes in a sample obtained from a subject or lymphocytes isolated from such sample, wherein expanding comprises at least two phases of expansion, and b) adding one or more peptides during at least one of the at least two phases of expansion, wherein each of said peptide(s) comprises a different antigen and wherein antigen-specific lymphocytes are expanded. In certain embodiments, the methods comprise adding two or more peptide(s) (i.e., a pool of peptides). In certain embodiments, the peptide(s) are added in soluble form. In certain embodiments, the peptide(s) are presented on the surface of an antigen presenting cell (APC). In certain embodiments, the APCs are incubated with soluble peptide(s), which leads to the APC presenting peptide(s) on its surface (e.g., either directly binding to an MHC on its surface or by being processed by the APC). In certain embodiments, the APCs are engineered to express the peptide(s) (e.g., via translation or transduction). In certain embodiments, the peptide(s) being added are both soluble peptide(s) together with peptide(s) presented on the surface of an APC (e.g., engineered to express the peptide(s), pre-incubated with the peptide(s), or both). In certain embodiments, soluble peptide(s) are added along with APCs that have not been previously induced to present the peptide(s) on its surface prior to being co-cultured with the lymphocytes.

A peptide useful for the methods as described herein can comprise any peptide that is capable of binding to a major histocompatibility complex (MHC) in a manner such that the MHC presenting the peptide can bind to a receptor on a lymphocyte, preferably in a specific manner. In certain embodiments, such binding induces a T cell response. In certain embodiments, such binding induces a natural killer cell response.

Examples include peptides produced by hydrolysis and most typically, synthetically produced peptides, including specifically designed peptides and peptides where at least some of the amino acid positions are conserved among several peptides and the remaining positions are random.

Class I MHC typically present peptides derived from proteins actively synthesized in the cytoplasm of the cell. In contrast, class II MHC typically present peptides derived either from exogenous proteins that enter a cell's endocytic pathway or from proteins synthesized in the ER. Intracellular trafficking permits a peptide to become associated with an MHC protein.

In certain embodiments, the peptide(s) are such that the polypeptide is centered on an individual mutated amino acid within the antigen.

The length of the peptides of the invention may comprise less than 100 amino acids, less than 50 amino acids, less than 40 amino acids, less than 30 amino acids, less than 20 amino acids, or less than 15 amino acids. In certain embodiments, the peptides may consist of at least 5 amino acids, for example, at least 10 amino acids, at least 15 amino acids, at least 20 amino acids, at least 25 amino acids, at least 30 amino acids or at least 35 amino acids. In certain embodiments, the peptide is from about 5 to about 60 amino acid residues, about 6 to about 55 amino acid residues, about 7 to about 50 amino acid residues, about 8 to about 45 amino acid residues, about and about 9 to about 40 amino acid residues, about 10 to about 35, about 12 to about 30 including any size peptide between 5 and 40 amino acids in length, in whole integer increments (i.e., 5, 6, 7, 8, 9 . . . 100).

In certain embodiments, the peptides of the invention may comprise about 9 to about 31 amino acid residues, about 9 to about 30 amino acid residues, about 9 to about 29 amino acid residues, about 9 to about 28 amino acid residues, about 9 to about 27 amino acid residues, about 9 to about 26 amino acid residues, about 9 to about 25 amino acid residues, about 9 to about 24 amino acid residues, about 9 to about 23 amino acid residues, about 9 to about 22 amino acid residues, about 9 to about 21 amino acid residues, about 9 to about 20 amino acid residues, about 9 to about 19 amino acid residues, about 9 to about 18 amino acid residues, about 9 to about 17 amino acid residues, about 9 to about 16 amino acid residues, about 9 to about 15 amino acid residues, about 9 to about 14 amino acid residues, about 9 to about 13 amino acid residues, about 9 to about 12 amino acid residues, about 9 to about 11 amino acid residues, or about 9 to about 10 amino acid residues.

In certain embodiments, the peptides of the invention may comprise about 9 to about 31 amino acid residues, about 10 to about 30 amino acid residues, about 10 to about 29 amino acid residues, about 10 to about 28 amino acid residues, about 10 to about 27 amino acid residues, about 10 to about 26 amino acid residues, about 10 to about 25 amino acid residues, about 10 to about 24 amino acid residues, about 10 to about 23 amino acid residues, about 10 to about 22 amino acid residues, about 10 to about 21 amino acid residues, about 10 to about 20 amino acid residues, about 10 to about 19 amino acid residues, about 10 to about 18 amino acid residues, about 10 to about 17 amino acid residues, about 10 to about 16 amino acid residues, about 10 to about 15 amino acid residues, about 10 to about 14 amino acid residues, about 10 to about 13 amino acid residues, about 10 to about 12 amino acid residues, or about 10 to about 11 amino acid residues.

In certain embodiments, the peptides of the invention may comprise about 9 to about 31 amino acid residues, about 12 to about 30 amino acid residues, about 12 to about 29 amino acid residues, about 12 to about 28 amino acid residues, about 12 to about 27 amino acid residues, about 12 to about 26 amino acid residues, about 12 to about 25 amino acid residues, about 12 to about 24 amino acid residues, about 12 to about 23 amino acid residues, about 12 to about 22 amino acid residues, about 12 to about 21 amino acid residues, about 12 to about 20 amino acid residues, about 12 to about 19 amino acid residues, about 12 to about 18 amino acid residues, about 12 to about 17 amino acid residues, about 12 to about 16 amino acid residues, about 12 to about 15 amino acid residues, about 12 to about 14 amino acid residues, or about 12 to about 13 amino acid residues.

In certain embodiments, the peptides of the invention may comprise about 9 to about 31 amino acid residues, about 15 to about 30 amino acid residues, about 15 to about 29 amino acid residues, about 15 to about 28 amino acid residues, about 15 to about 27 amino acid residues, about 15 to about 26 amino acid residues, about 15 to about 25 amino acid residues, about 15 to about 24 amino acid residues, about 15 to about 23 amino acid residues, about 15 to about 22 amino acid residues, about 15 to about 21 amino acid residues, about 15 to about 20 amino acid residues, about 15 to about 19 amino acid residues, about 15 to about 18 amino acid residues, about 15 to about 17 amino acid residues, or about 15 to about 16 amino acid residues.

In certain embodiments, the peptides of the invention may comprise about 9 to about 31 amino acid residues, about 25 to about 30 amino acid residues, about 25 to about 29 amino acid residues, about 25 to about 28 amino acid residues, about 25 to about 27 amino acid residues, or about 25 to about 26 amino acid residues.

While naturally MHC Class II-bound peptides vary from about 9-40 amino acids, generally the peptide can be truncated to an about 9-11 amino acid core without loss of MHC binding activity or lymphocyte recognition. In certain embodiments, the peptides are from about 9 to about 10 amino acids long, about 12 to about 15 amino acids long, or about 25 to about 31 amino acids long.

In certain embodiments, the APCs are engineered to express the peptide(s). In certain embodiments, the APC is engineered by at least one of transfection, transduction, or temporary cell membrane disruption (i.e., cell squeeze) to introduce at least one polynucleotide encoding the peptide(s) into the APC. Thus, polynucleotide(s) expressing the peptide(s) are introduced into the APC. In certain embodiments, the polynucleotide is a DNA plasmid. In certain embodiments, the polynucleotide is an mRNA molecule. Methods of introducing genes encoding peptide(s) are discussed below in greater detail. In certain embodiments, the peptide(s) are introduced via viral methods of transfection/transduction. In certain embodiments, each gene encodes a polypeptide that is about 9 to about 31 amino acids long and centered on an individual mutated amino acid found within the antigen.

In certain embodiments, the polynucleotide comprises about 1 to about 100 genes that encode separate peptides. In certain embodiments, the polynucleotide comprises about 2 to about 90, about 3 to about 80, about 4 to about 70, about 5 to about 60, about 6 to about 50, about 7 to about 40, about 8 to about 30, about 9 to about 20, or about 10 to about 15 genes that encode separate peptides. In certain embodiments, the polynucleotide comprises about 1 to about 50, about 1 to about 40, about 1 to about 30, about 1 to about 20, about 1 to about 15, about 1 to about 10, about 1 to about 5, about 2 to about 50, about 2 to about 40, about 2 to about 30, about 2 to about 20, about 2 to about 15, about 2 to about 10, about 2 to about 5, 5 to about 50, about 5 to about 40, about 5 to about 30, about 5 to about 20, about 5 to about 15, about 5 to about 10, about 5 to about 5, about 10 to about 50, about 10 to about 40, about 10 to about 30, about 10 to about 20, or about 10 to about 15 genes that encode separate peptides. In certain embodiments, the polynucleotide comprises about 1 to about 15, about 1 to about 5, about 2 to about 40, about 2 to about 15, or about 2 to about 5 genes that encode separate peptides.

In certain embodiments, the polynucleotide comprises at least about 1, about 2, about 3, about 4, about 5, about 6, about 7, about 8, about 9, about 10, about 11, about 12, about 13, about 14, about 15, about 16, about 17, about 18, about 19, about 20, about 22, about 24, about 26, about 28, about 30, about 32, about 34, about 36, about 38, about 40, about 42, about 44, about 46, about 48, or about 50 genes encoding separate peptides.

In certain embodiments, the polynucleotide comprises about 1, about 2, about 3, about 4, about 5, about 6, about 7, about 8, about 9, about 10, about 11, about 12, about 13, about 14, about 15, about 16, about 17, about 18, about 19, about 20, about 22, about 24, about 26, about 28, about 30, about 32, about 34, about 36, about 38, about 40, about 42, about 44, about 46, about 48, or about 50 genes encoding separate peptides. In certain embodiments, the polynucleotide comprises 1, 2, 3, 4, 5, 10, or 15 genes that encode separate peptides. In certain embodiments, the polynucleotide comprises 5 genes that encode separate peptides. In certain embodiments, the polynucleotide consists essentially of 1, 2, 3, 4, 5, 10, or 15 genes that encode separate peptides. In certain embodiments, the polynucleotide consists essentially of 5 genes that encode separate peptides. In certain embodiments, the polynucleotide consists essentially of one gene encoding a peptide of the invention.

Figure 6A:
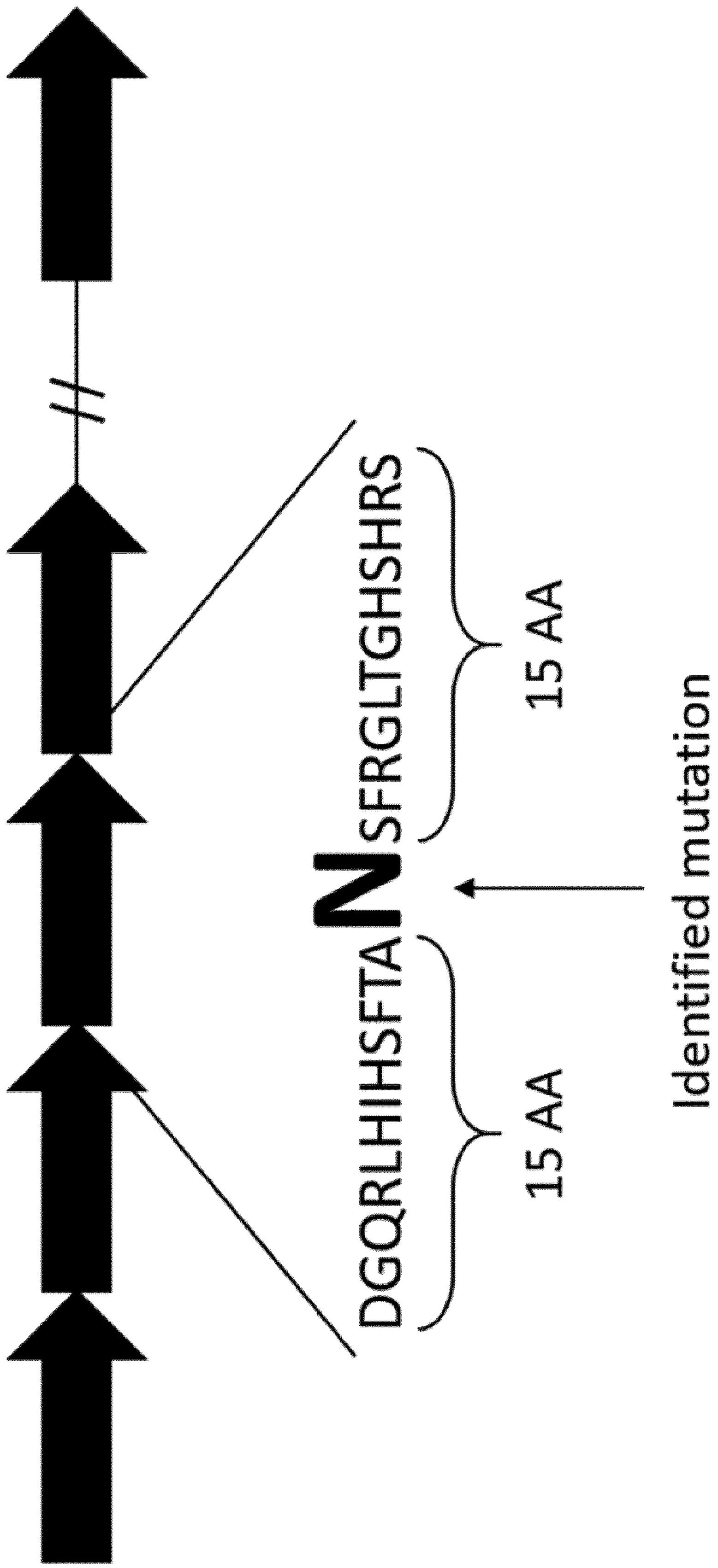
FIG. 6A-6B shows the schema of a non-limiting embodiments as disclosed herein.

In certain embodiments, the method may comprise introducing a polynucleotide into the APC as a tandem minigene (TMG) construct, wherein each minigene comprises a different gene, each gene including an antigen (e.g., tumor-specific mutation that encodes a mutated amino acid sequence). A TMG is a DNA sequence composed of a variable number of minigenes, each encoding a 25-31-mer centered on an individual mutated amino acid (FIG. 6A). The TMG can be cloned into an appropriate expression vector, which can be used as a template to produce in vitro transcribed (IVT) mRNA. This mRNA can then be introduced into the APC (e.g., by known means of mRNA transfection, including electroporation). In certain embodiments, the minigenes are separated by linkers. TMGs can be made by any method well known to those of skill in the art.

Table 2 and FIGS. 7 and 17-20 provides a non-limiting example of a TMG useful for the methods of the invention.

Each minigene may encode one mutation identified by the inventive methods flanked on each side of the mutation by any suitable number of contiguous amino acids from the endogenous protein encoded by the identified gene. The number of minigenes in the construct is not limited and may include for example, about 2 about 3, about 4, about 5, about 10, about 11, about 12, about 13, about 14, about 15, about 20, about 25, or more, or a range as defined above for the number of genes in a polynucleotide. In certain embodiments, the TMC comprises about 5 minigenes. In certain embodiments, the minigenes are separated by linkers (FIG. 7 provides non-limiting examples of linkers useful for minigenes). The APCs express the mutated amino acid sequences encoded by the TMG construct and display the antigens' amino acid sequences, bound to an MHC molecule, on the cell membrane. In an embodiment, the method may comprise preparing more than one TMG construct, each construct encoding a different set of antigen amino acid sequences encoded by different genes and introducing each TMG construct into the same or different population of APC. In this regard, multiple populations of APCs, each population expressing and displaying mutated amino acid sequences encoded by different TMG constructs, may be obtained.

Peptides include peptides comprising at least a portion, e.g., an antigenic determinant, of a protein selected from a group consisting of a protein associated with a tumor, an autoimmune disorder, proteins of infectious agents, and toxic proteins (e.g., β-amyloid).

Cancer is notorious for its ability to hide from the immune system as if it were normal tissue, while still being able to wreak havoc on the body. Recently, however, scientist have established that somatic or passenger mutations within the tumor give rise to new antigens or neo-antigens. These neo-antigens can be recognized by the adaptive immune system as "non-self" and serve as how immune systems can differentiate cancer from normal cells. A single base-pair change to a DNA sequence, resulting in a single amino-acid difference in the encoded protein, can be enough to alert the immune system that something is awry, and cause it to mount a response to the tumor. As tumor cells are highly prone to developing multiple mutations which may alter the amino acid sequence of the cell's peptides, thus, converting them from a self-protein to one carrying a neo-antigen. These neo-antigens are unique to the cancer cells and by contrast, other antigens that have been explored for cancer immunotherapy may also be expressed in normal cells, thereby making the patient's healthy tissues vulnerable to an immune response. Thus, neo-antigens may make strong candidates for personalized immunotherapy.

In certain instances, the method may comprise identifying one or more genes in the tumor cell of a patient, each gene containing a tumor-specific mutation that encodes a mutated amino acid sequence (i.e., containing a neo-antigen). The tumor cell may be obtained from any sample derived from a subject which contains, or is expected to contain, tumor cells. The sample may be any sample taken from the body of the subject, such as tissue (e.g., primary tumor or tumor metastases) or bodily fluid (e.g., blood, ascites, or lymph). The nucleic acid of the cancer cell may be DNA or RNA.

A tumor-specific neo-antigen derives from a mutation in any gene which encodes a non-silent mutation, and which is present in a tumor cell of the subject, but which is not present in a normal somatic cell of the subject. The neo-antigen may be expressed at the cell surface of the tumor cell where it is recognized by components of the humoral immune system such as B lymphocytes (B cells). Intracellular tumor antigens are processed into shorter peptide fragments which form complexes with major histocompatibility complex (MHC) molecules and are presented on the cell surface of cancer cells, where they are recognized by the T cell receptors (TCR's) of T lymphocytes (T cells).

In certain embodiments, the peptides used are private peptides. Private peptides are neo-antigens uniquely expressed in a patient for a particular tumor. Thus, a private peptide is one in which cannot be used for another patient. When a neo-antigen is common to two or more individuals, it is a shared peptide.

Non-limiting examples of tumor-associated proteins from which tumor antigens (including neo-antigens) can be identified include, e.g., 13HCG, 43-9F, 5T4, 791Tgp72, adipophilin, AIM-2, ALDH1A1, alpha-actinin-4, alpha-fetoprotein ("AFP"), ARTC1, B-RAF, BAGE-1, BCA225, BCLX (L), BCR-ABL fusion protein b3a2, beta-catenin, BING-4, brain glycogen phosphorylase, BTAA, c-met, CA-125, CA-15-3 (CA 27.29\BCAA), CA-19-9, CA-242, CA-50, CA-72-4, CALCA, CAM 17.1, CAM43, carcinoembryonic antigen ("CEA"), CASP-5, CASP-8, CD274, CD45, CD68\KP1, Cdc27, CDK12, CDK4, CDKN2A, CEA, CLPP, CO-029, COA-1, CPSF, CSNK1A1, CT-7, CT9/BRDT, CTAG1, CTAG2, CTp11, cyclin D1, Cyclin-AL dek-can fusion protein, DKK1, E2A-PRL, EBNA, EF2, EFTUD2, Elongation factor 2, ENAH (hMena), Ep-CAM, EpCAM, EphA3, epithelial tumor antigen ("ETA"), Epstein Barr virus antigens, ETV6-AML1 fusion protein, EZH2, FGF5, FLT3-ITD, FN1, G250, G250/MN/CAIX, Ga733 (EpCAM), GAGE-1,2,8, GAGE-3,4,5,6,7, GAS7, glypican-3, GnTV, gp100, gp100/Pme117, GPNMB, H-ras, H4-RET, HAUS3, Hepsin, HER-2/neu, HERV-K-MEL, HLA-A11, HLA-A2, HLA-DOB, HOM-MD-21, HOM-MD-397, Hom/Me1-40, Hom/Me1-55, HPV E2, HPV E6, HPV E7, hsp70-2, HTgp-175, IDO1, IGF2B3, IGH-IGK, IL13Ralpha2, Intestinal carboxyl esterase, K-ras, Kallikrein 4, KIAAO205, KIF20A, KK-LC-1, KKLC1, KM-HN-1, KMHN1 also known as CCDCl10, LAGE-1, LAGE-2, LB33/MUM-1, LDLR-fucosyltransferaseAS fusion protein, Lengsin, M-CSF, M344, MA-50, MAGE-1, MAGE-2, MAGE-3, MAGE-4, MAGE-5, MAGE-6, MAGE-AL MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, MAGE-B (MAGE-B1-MAGE-B24), MAGE-C(MAGE-C1/CT7, CT10), MAGE-C1, MAGE-C2, MAGE-Xp2 (MAGE-B2), MAGE-Xp3 (MAGE-B3), MAGE-Xp4 (MAGE-B4), malic enzyme, mammaglobin-A, MAPE, MART-I, MART-2, MATN, MC1R, MCSP, mdm-2, ME1, Melan-A/MART-1, Meloe, MG7-Ag, Midkine, MMP-2, MMP-7, MOV18, MUC1, MUCSAC, mucin, MUM-1, MUM-2, MUM-3, MYL-RAR, Myosin, Myosin class I, N-ras, N-raw, NA88-A, NAG, NB\170K, neo-PAP, NFYC, nm-23H1, NuMa, NY-BR-1, NY-CO-1, NY-CO-2, NY-ESO1, NY-ESO-1/LAGE-2, OAL OGT, OS-9, P polypeptide, p15 (58), p16, p185erbB2, p180erbB-3, p53, PAP, PAX5, PBF, pml-RARalpha fusion protein, polymorphic epithelial mucin ("PEM"), PPP1R3B, PRAME, PRDX5, PSA, PSCA, PSMA, PTPRK, RAB38/NY-MEL-1, RAGE-1, RBAF600, RCAS1, RGSS, RhoC, RNF43, RU2AS, SAGE, SART-1, SART-3, SCP-1, SDCCAG16, secernin 1, SIRT2, SNRPD1, SOX10, Sp17, SPA17, SSX-1, SSX-2, SSX-4, SSX-5, STEAP1, survivin, SYT-SSX1 or -SSX2 fusion protein, TA-90 (Mac-2 binding protein\cyclophilin C-associated protein), TAAL6, TAG-1, TAG-2, TAG-72-4, TAGE, Telomerase, TERT, TGF-betaRll, TLP, TPBG, TPS TRAG-3, Triosephosphate isomerase, TRP-1, TRP-2, TRP-1/gp75, TRP-2, TRP2-INT2, TSP-180, TSP50, tyrosinase, tyrosinase ("TYR"), VEGF, WT1, XAGE-1b/GAGED2a, Kras, WT-1 antigen (in lymphoma and other solid tumors), ErbB receptors, Melan A [MART1], gp 100, tyrosinase, TRP-1/gp 75, and TRP-2 (in melanoma); MAGE-1 and MAGE-3 (in bladder, head and neck, and non-small cell carcinoma); HPV EG and E7 proteins (in cervical cancer); Mucin [MUC-1] (in breast, pancreas, colon, and prostate cancers); prostate-specific antigen [PSA] (in prostate cancer); carcinoembryonic antigen [CEA] (in colon, breast, and gastrointestinal cancers), and such shared tumor-specific antigens as MAGE-2, MAGE-4, MAGE-6, MAGE-10, MAGE-12, BAGE-1, CAGE-1,2,8, CAGE-3 TO 7, LAGE-1, NY-ESO-1/LAGE-2, NA-88, GnTV, TRP2-INT2. For example, antigenic peptides characteristic of tumors include those listed in Cancer Vaccines and Immunotherapy (2000) Eds Stern, Beverley and Carroll, Cambridge University Press, Cambridge, Cancer Immunology (2001) Kluwer Academic Publishers, The Netherlands, International Patent Application Publication No. WO 20000/020581 and U.S. Patent Application Publication No. 2010/0284965, and cancerimmunity.org/peptidedatabase/Tcellepitopes which are each incorporated herein by reference in their entirety for all intended purposes.

Identifying one or more genes in the nucleic acid of a tumor cell or cells from some other bodily sample may comprise sequencing the whole exome, the whole genome, or the whole transcriptome of the tumor cell. Transcriptome sequencing is sequencing the messenger RNA or transcripts from a cell. The transcriptome is the small percentage of the genome (less than 5% in humans) that is transcribed into RNA. Genome sequencing is sequencing the complete DNA sequence of an organism's genome. Exome sequencing is sequencing the protein-encoding parts of the genome.

In certain embodiments, the depth of sequencing can be varied. In next-generation sequencing, overlapping fragments of the DNA sample of interest are produced and sequenced. The overlapping sequences are then aligned to produce the full set of aligned sequence reads. Depth of sequencing, also called coverage of sequencing, refers to the number of nucleotides contributing to a portion of an assembly. On a genome basis, sequencing depth refers to the number of times each base has been sequenced. For example, a genome sequenced to 3 OX means that each base in the sequence was covered by 30 sequencing reads. On a nucleotide basis, depth of sequencing refers to the number of sequences that added information about a single nucleotide.

In certain embodiments, particular portions of the subject's genome are sequenced (e.g., tumor), for example. In most cases, sequencing the entire genome/transcriptome is preferred; the genome may be sequenced to a shallow depth or a deep depth, allowing coverage or less or more portions of the genome/transcriptome.

Sequencing may be carried out in any suitable manner known in the art. Examples of sequencing techniques include, but are not limited to, Next Generation Sequencing (NGS) (also referred to as "massively parallel sequencing technology") or Third Generation Sequencing. NGS refers to non-Sanger-based high-throughput DNA sequencing technologies. Non-limiting examples of NGS technologies and platforms include sequencing-by-synthesis (a.k.a. "pyrosequencing") (e.g., using the GS-FLX 454 Genome Sequencer, 454 Life Sciences (Branford, Conn.), ILLUMINA SOLEXA Genome Analyzer (Illumina Inc., San Diego, Calif.), or the ILLUMINA HISEQ 2000 Genome Analyzer (Illumina), or as described in, e.g., Ronaghi et al., Science, 281(5375): 363-365 (1998)), sequencing-by-ligation (as implemented, e.g., using the SOLID platform (Life Technologies Corporation, Carlsbad, Calif.) or the POLONATOR G.007 platform (Dover Systems, Salem, N.H.)), single-molecule sequencing (as implemented, e.g., using the PACBIO RS system (Pacific Biosciences (Menlo Park, Calif.) or the HELISCOPE platform (Helicos Biosciences (Cambridge, Mass.)), nano-technology for single-molecule sequencing (as implemented, e.g., using the GRIDON platform of Oxford Nanopore Technologies (Oxford, UK), the hybridization-assisted nano-pore sequencing (HANS) platforms developed by Nabsys (Providence, R.I.), and the ligase-based DNA sequencing platform with DNA nanoball (DNB) technology referred to as probe-anchor ligation (cPAL)), electron microscopy-based technology for single-molecule sequencing, and ion semiconductor sequencing. e.g., those described in Zhang et al., J. Genet. Genomics, 38(3): 95-109 (2011) and Voelkerding et al., Clinical Chemistry, 55: 641-658 (2009).

In some embodiments, the peptides are generated by predictive modeling. Any suitable method for predicting peptide sequences can be used (e.g., NetMHC algorithm). For example, analyzing the difference DNA or RNA marker set to produce a specific antigen/epitope set (e.g., tumor specific) comprises using a predictive algorithm that determines the binding of epitope peptides to MHC molecules. Optionally, the specific antigen/epitope set is refined to provide an MHC-restricted specific antigen/epitope set. For example, MHC I-restricted epitopes of the K, D or L alleles can be provided. MHC-restricted epitope sets can be produced by determining binding of a peptide containing the epitope to an MHC-allele-specific peptide. One example of such an algorithm is NetMHC-3.2 which predicts the binding of peptides to a number of different HLA alleles using artificial neural networks (ANNs) and weight matrices.

By way of example and not limitation, the DNA (or RNA) sequence differences between the healthy and cancer tissues, in combination with a mammal's MHC composition, can be analyzed by an epitope predictive algorithm such as NetMHC. This algorithm produces a list of potential tumor-specific epitopes for this individual mammal and gives each epitope a numerical score. In the current state of the art, a high score implies a good probability of the epitope being able to immunize, and a low (including a negative) score implies a poor probability of the epitope being able to immunize. The method further comprises providing a numerical score for each epitope in the tumor-specific epitope set or the MHC-restricted tumor-specific epitope set, wherein the numerical score is calculated by subtracting a score for the normal epitope (non-mutated) from a score for the tumor-specific epitope (mutated). The numerical score for the normal epitope is subtracted from the numerical score for the mutant cancer epitope, and a numerical value for the difference is obtained—the Differential Agretopic Index (DAI) for the epitope. The putative epitopes can be ranked on basis of the DAI.

In other embodiments, peptides of the invention can be identified by sequencing of enzymatic digests using multi-dimensional MS techniques (MSn) including tandem mass spectrometry (MS/MS)). Such proteomic approaches permit rapid, highly automated analysis (see, e.g., K. Gevaert and J. Vandekerckhove, Electrophoresis 21:1145-1154 (2000); Bassani-Sternberg M. (2018) Mass Spectrometry Based Immunopeptidomics for the Discovery of Cancer Neoantigens. In: Schrader M., Fricker L. (eds) Peptidomics. Methods in Molecular Biology, vol 1719. Humana Press, New York, N.Y., each incorporated herein by reference in their entirety for all purposes).

Antigen Presenting Cells

In one aspect, described herein are methods for expanding antigen-specific lymphocytes ex vivo comprising expanding lymphocytes in a sample obtained from a subject or lymphocytes isolated from such sample, wherein expanding comprises adding one or more peptides during expansion, wherein each of said peptide(s) comprises a different antigen and wherein antigen-specific lymphocytes are formed. In certain embodiments, the peptide(s) are presented on the surface of an antigen presenting cell (APC). In certain embodiments, the APCs are incubated with soluble peptide(s), which leads to the APC presenting peptide(s) on its surface (e.g., either directly binding to an MHC on its surface or by being processed by the APC). In certain embodiments, the APCs are engineered to express the peptide(s) (e.g., via translation or transduction). In certain embodiments, the peptide(s) being added are both soluble peptide(s) together with peptide(s) presented on the surface of an APC (e.g., engineered to express the peptide(s), pre-incubated with the peptide(s), or both). In certain embodiments, soluble peptide(s) are added along with APCs that have not been previously induced to present the peptide(s) on its surface prior to being co-cultured with the lymphocytes.

In certain embodiments, the methods comprise adding two or more peptide(s) (i.e., a pool of different peptides). In certain embodiments, if only one phase of expansion is conducted, it is using a pre-rapid expansion protocol (pre-REP). In certain embodiments, the antigen-specific lymphocytes are preferentially expanded over other lymphocytes present during the expansion. In certain embodiments, this preferential expansion results in an enrichment of antigen-specific lymphocytes. In certain embodiments, the peptide(s) are presented on the surface of an antigen presenting cell (APC). In certain embodiments, the APCs are incubated with soluble peptide(s), which leads to the APC presenting peptide(s) on its surface (e.g., either directly binding to an MHC on its surface or by being processed by the APC). In certain embodiments, the APCs are engineered to express the peptide(s) (e.g., via translation or transduction). In certain embodiments, the peptide(s) being added are both soluble peptide(s) together with peptide(s) presented on the surface of an APC (e.g., engineered to express the peptide(s), pre-incubated with the peptide(s), or both). In certain embodiments, soluble peptide(s) are added along with APCs that have not been previously induced to present the peptide(s) on its surface prior to being co-cultured with the lymphocytes.

In certain embodiments, the APCs may be autologous, allogeneic, syngeneic, or xenogeneic with respect to the lymphocytes and/or subject. In certain embodiments, APCs autologous to the subject are used in order to allow the presentation of peptide(s) in the context of the subject's own MHC.

In certain embodiments, the APCs are artificial APCs. In certain embodiments, the APCs are not artificial.

In certain embodiments, the APCs are incubated with peptide(s) in order for the peptide(s) to be presented on the surface of the APC.

In certain embodiments, the APCs are incubated with the peptide(s) at the same time that they are introduced to the co-culture with the lymphocytes.

In certain embodiments, the APCs are incubated with the peptide(s) prior to being co-cultured with the lymphocytes. In such an instance, the APCs can be said to be pulsed or pre-loaded with the peptide. In certain embodiments, the peptide(s) may be incubated with the APC at a concentration from about 0.1 nM to about 100 μM for each peptide. In certain embodiments, the peptide(s) may be incubated with the APC at a concentration of about 1 nM to about 90 μM, about 10 nM to about 80 μM, about 50 nM to about 70 μM, about 100 nM to about 60 μM, about 150 nM to about 50 μM, about 200 nM to about 40 μM, about 250 nM to about 30 μM, about 300 nM to about 20 μM, about 350 nM to about 10 μM, about 400 nM to about 9 μM, about 450 nM to about 8 μM, about 500 nM to about 7 μM, about 550 nM to about 6 μM, about 600 nM to about 5 μM, about 650 nM to about 4 μM, about 700 nM to about 3 μM, about 750 nM to about 2.5 μM, about 800 nM to about 2 μM, about 900 nM to about 1.5 μM, or about 950 nM to about 1.25 μM for each peptide. In certain embodiments, the peptide(s) may be incubated with the APC at a concentration of about 100 nM to about 100 μM, about 250 nM to about 75 μM, about 500 nM to about 50 μM, about 750 nM to about 25 μM, about 900 nM to about 10 μM or about 990 nM to about 5 μM for each peptide.

In certain embodiments, the peptide(s) may be incubated with the APC at a concentration of at least about 0.1 nM, about 1 nM, about 5 nM, about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 260 nM, about 270 nM, about 280 nM, about 290 nM, about 300 nM, about 310 nM, about 320 nM, about 330 nM, about 340 nM, about 350 nM, about 360 nM, about 370 nM, about 380 nM, about 390 nM, about 400 nM, about 410 nM, about 420 nM, about 430 nM, about 440 nM, about 450 nM, about 460 nM, about 470 nM, about 480 nM, about 490 nM, about 500 nM, about 510 nM, about 520 nM, about 530 nM, about 540 nM, about 550 nM, about 560 nM, about 570 nM, about 580 nM, about 590 nM, about 600 nM, about 610 nM, about 620 nM, about 630 nM, about 640 nM, about 650 nM, about 660 nM, about 670 nM, about 680 nM, about 690 nM, about 700 nM, about 710 nM, about 720 nM, about 730 nM, about 740 nM, about 750 nM, about 760 nM, about 770 nM, about 780 nM, about 790 nM, about 800 nM, about 810 nM, about 820 nM, about 830 nM, about 840 nM, about 850 nM, about 860 nM, about 870 nM, about 880 nM, about 890 nM, about 900 nM, about 910 nM, about 920 nM, about 930 nM, about 940 nM, about 950 nM, about 960 nM, about 970 nM, about 980 nM, about 990 nM, about 1 μM, about 2 μM, about 3 μM, about 4 μM, about 5 μM, about 6 μM, about 7 μM, about 8 μM, about 9 μM, about 10 μM, about 20 μM, about 30 μM, about 40 μM, about 50 μM, about 60 μM, about 70 μM, about 80 μM, about 90 μM, or about 100 μM for each peptide.

In certain embodiments, the peptide(s) may be incubated with the APC at a concentration of about 0.1 nM, about 1 nM, about 5 nM, about 10 nM, about 20 nM, about 30 nM, about 40 nM, about 50 nM, about 60 nM, about 70 nM, about 80 nM, about 90 nM, about 100 nM, about 110 nM, about 120 nM, about 130 nM, about 140 nM, about 150 nM, about 160 nM, about 170 nM, about 180 nM, about 190 nM, about 200 nM, about 210 nM, about 220 nM, about 230 nM, about 240 nM, about 250 nM, about 260 nM, about 270 nM, about 280 nM, about 290 nM, about 300 nM, about 310 nM, about 320 nM, about 330 nM, about 340 nM, about 350 nM, about 360 nM, about 370 nM, about 380 nM, about 390 nM, about 400 nM, about 410 nM, about 420 nM, about 430 nM, about 440 nM, about 450 nM, about 460 nM, about 470 nM, about 480 nM, about 490 nM, about 500 nM, about 510 nM, about 520 nM, about 530 nM, about 540 nM, about 550 nM, about 560 nM, about 570 nM, about 580 nM, about 590 nM, about 600 nM, about 610 nM, about 620 nM, about 630 nM, about 640 nM, about 650 nM, about 660 nM, about 670 nM, about 680 nM, about 690 nM, about 700 nM, about 710 nM, about 720 nM, about 730 nM, about 740 nM, about 750 nM, about 760 nM, about 770 nM, about 780 nM, about 790 nM, about 800 nM, about 810 nM, about 820 nM, about 830 nM, about 840 nM, about 850 nM, about 860 nM, about 870 nM, about 880 nM, about 890 nM, about 900 nM, about 910 nM, about 920 nM, about 930 nM, about 940 nM, about 950 nM, about 960 nM, about 970 nM, about 980 nM, about 990 nM, about 1 μM, about 2 μM, about 3 μM, about 4 μM, about 5 μM, about 6 μM, about 7 μM, about 8 μM, about 9 μM, about 10 μM, about 20 μM, about 30 μM, about 40 μM, about 50 μM, about 60 μM, about 70 μM, about 80 μM, about 90 μM, or about 100 μM for each peptide. In certain embodiments, the peptide(s) may be incubated with the APC at a concentration of about 1 μM for each peptide. In certain embodiments, the peptide(s) may be incubated with the APC at a concentration of about 2 μM for each peptide.

In some instances, incubation with the peptide(s) can lead to the peptide(s) being directly bound to the surface of the APCs (e.g., via MHC), which in that case internal processing of the peptide(s) is not required by the APC. Direct binding allows for faster epitope presentation and, thus, shorter assay times. While APCs may already display peptide(s) on their surface in complex with MHCs, many of these MHC-bound peptides are replaced by the incubation with peptide(s) of the invention, resulting in MHC-peptide complexes, that can be used to expand antigen-specific lymphocytes.

In certain embodiments, the APC is engineered to express at least one immunomodulator. The immunomodulator can act to further enhance the expansion of the lymphocytes. In certain embodiments, the immunomodulatory can act to further enhance the expansion of an antigen-specific lymphocytes. In certain embodiments, the immunomodulatory acts synergistically with the APC presenting peptide(s) to enhance the expansion of the lymphocytes and/or antigen-specific lymphocytes.

In certain embodiments, the APC is engineered to express the immunomodulator by at least one of transfection, transduction, or temporary cell membrane disruption thereof to introduce the at least one immunomodulator. In certain embodiments, the APC is engineered to express the immunomodulator by use of a gene-editing molecule. Examples of gene-editing molecules include, but are not limited to, endonucleases. Endonucleases are enzymes that cleave the phosphodiester bond within a polynucleotide chain, but they only break internal phosphodiester bonds. Examples of gene-editing endonucleases useful in the compositions and methods of the present invention include, but are not limited to, zinc finger nucleases (ZFns), transcription activator-like effector nucleases (TALENs), meganucleases, restriction endonucleases, recombinases, and Clustered Regularly Interspersed Short Palindromic Repeats, (CRISPR)/CRISPR-associated (Cas) proteins. Examples of Cas proteins useful in the methods of the invention include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, $Cas_{10}d$, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

In certain embodiments, the APC is engineered to transiently express the immunomodulator. In certain embodiments, the APC is engineered to stably express the immunomodulator.

In certain embodiments, non-limiting examples of immunomodulators for use in engineering the APCs includes OX40L, 4-1BBL, CD80, CD86, CD83, CD70, CD40L, GITR-L, CD127L, CD30L (CD153), LIGHT, BTLA, ICOS-L (CD275), SLAM (CD150), CD662L, interleukin-12 (IL-12), interleukin-7 (IL-7), interleukin-15 (IL-15), interleukin-17 (IL-17), interleukin-21 (IL-21), or interleukin-4 (IL-4).

The APCs can be engineered to express the peptide(s) and/or immunomodulators by any means known in the art, including, but not limited to, transfection, viral delivery (i.e., transduction), liposomal delivery, electroporation, cell squeeze (e.g., cells are first disrupted (e.g., squeezed, deformed, or compressed) followed by exposure to an applied energy field, e.g., an electric, magnetic, or acoustic field), injection, cationic polymer, a cationic lipid, calcium phosphate, and endocytosis.

For instance, electroporation can be used to permeabilize the APCs by the application of an electrostatic potential to the cell of interest. APCs subjected to an external electric field in this manner are subsequently predisposed to the uptake of exogenous nucleic acids. Electroporation of mammalian cells is described in detail, e.g., in Chu et al., Nucleic Acids Research 15:131 1 (1987), the disclosure of which is incorporated herein by reference. A similar technique, Nucleofection™, utilizes an applied electric field in order to stimulate the uptake of exogenous polynucleotides into the nucleus of a eukaryotic cell. Nucleofection™ and protocols useful for performing this technique are described in detail, e.g., in Distler et al., Experimental Dermatology 14:315 (2005), as well as in US 2010/03171 14, the disclosures of each of which are incorporated herein by reference in their entirety for all intended purposes.

Additional techniques useful for the transfection of APCs include the cell squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a human target cell. Cell squeeze-poration is described in detail, e.g., in Sharei et al., Journal of Visualized Experiments 81:e50980 (2013), the disclosure of which is incorporated herein by reference in its entirety for all intended purposes.

Lipofection represents another technique useful for transfection of target cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, for instance, by direct fusion of the liposome with the cell membrane or by endocytosis of the complex. Lipofection is described in detail, for instance, in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane include activated dendrimers (described, e.g., in Dennig, Topics in Current Chemistry 228:227 (2003), the disclosure of which is incorporated herein by reference) and diethylaminoethyl (DEAE)-dextran, the use of which as a transfection agent is described in detail, for instance, in Gulick et al., Current Protocols in Molecular Biology 40:1:9.2:9.2.1 (1997), the disclosure of which is incorporated herein by reference. Magnetic beads are another tool that can be used to transfect target cells in a mild and efficient manner, as this methodology utilizes an applied magnetic field in order to direct the uptake of nucleic acids. This technology is described in detail, for instance, in US 2010/0227406. The disclosure of each reference discussed above is incorporated herein by reference in their entirety for all intended purposes.

Another useful tool for inducing the uptake of exogenous nucleic acids by the APC is laserfection, a technique that involves exposing a cell to electromagnetic radiation of a particular wavelength in order to gently permeabilize the cells and allow polynucleotides to penetrate the cell membrane. This technique is described in detail, e.g., in Rhodes et al., Methods in Cell Biology 82:309 (2007), the disclosure of which is incorporated herein by reference in its entirety for all intended purposes.

Microvesicles represent another potential vehicle that can be used to modify the genome of an APC according to the methods described herein. For instance, microvesicles that have been induced by the co-overexpression of the glycoprotein VSV-G with, e.g., a genome-modifying protein, such as a nuclease, can be used to efficiently deliver proteins into a cell that subsequently catalyze the site-specific cleavage of an endogenous polynucleotide sequence so as to prepare the genome of the cell for the covalent incorporation of a polynucleotide of interest, such as a gene or regulatory sequence. The use of such vesicles, also referred to as Gesicles, for the genetic modification of eukaryotic cells is described in detail, e.g., in Quinn et al., Genetic Modification of Target Cells by Direct Delivery of Active Protein [abstract]. In: Methylation changes in early embryonic genes in cancer [abstract], in: Proceedings of the 18th Annual Meeting of the American Society of Gene and Cell Therapy; 2015 May 13, Abstract No. 122. The disclosure of each reference discussed above is incorporated herein by reference in their entirety for all intended purposes.

Various methods may be used to transduce cells. In some embodiments of the invention, a cell is transduced with a vector or plasmid, i.e., a nucleic acid molecule capable of transporting a nucleic acid sequence between different cellular or genetic environments. Different cellular environments include different cell types of the same organism while different genetic environments include cells of different organisms or other situations of cells with different genetic material and/or genomes. Non-limiting vectors of the invention include those capable of autonomous replication and expression of nucleic acid sequences (for delivery into the cell) present therein. Vectors may also be inducible for expression in a way that is responsive to factors specific for a cell type. Non-limiting examples include inducible by addition of an exogenous modulator in vitro or systemic delivery of vector inducing drugs in vivo. Vectors may also optionally comprise selectable markers that are compatible with the cellular system used. One type of vector for use in the practice of the invention is maintained as an episome, which is a nucleic acid capable of extra-chromosomal replication. Another type is a vector which is stably integrated into the genome of the cell in which it is introduced.

The types of vectors used for transduction include those based upon any virus. Vectors derived from retroviruses, including avian reticuloendotheliosis virus (duck infectious anaemia virus, spleen necrosis virus, Twiehaus-strain reticuloendotheliosis virus, C-type retrovirus, reticuloendotheliosis virus Hungary-2 (REV-H-2)), and feline leukemia virus (FeLV)), are particular non-limiting examples. Retroviral genomes have been modified for use as a vector (Cone & Mulligan, Proc. Natl. Acad. Sci., USA, 81:6349-6353, (1984)). Non-limiting examples of retroviruses which may be used as vectors of the invention include lentiviruses, such as human immunodeficiency viruses (HIV-1 and HIV-2), feline immunodeficiency virus (FIV), simian immunodeficiency virus (SIV), Maedi/Visna virus, caprine arthritis/encephalitis virus, equine infectious anaemia virus (EIAV), and bovine immunodeficiency virus (BIV); avian type C retroviruses, such as the avian leukosis virus (ALV); HTLV-BLV retroviruses, such as bovine leukaemia virus (BLV), human T cell lymphotropic virus (HTLV), and simian T cell lymphotropic virus; mammalian type B retroviruses, such as the mouse mammary tumor virus (MMTV); mammalian type C retroviruses, such as the murine leukaemia virus (MLV), feline sarcoma virus (FeSV), murine sarcoma virus, Gibbon ape leukemia virus, guinea pig type C virus, porcine type C virus, wooly monkey sarcoma virus, and viper retrovirus; spumavirus (foamy virus group), such as human spumavirus (HSRV), feline synctium-forming virus (FeSFV), human foamy virus, simian foamy virus, and bovine syncytial virus; and type D retroviruses, such as Mason-Pfizer monkey virus (MPMV), squirrel monkey retrovirus, and langur monkey virus.

Lentiviral and retroviral vectors may be packaged using their native envelope proteins or may be modified to be encapsulated with heterologous envelope proteins. Examples of envelope proteins include, but are not limited to, an amphotropic envelope, an ecotropic envelope, or a xenotropic envelope, or may be an envelope including amphotropic and ecotropic portions. The protein also may be that of any of the above mentioned retroviruses and lentiviruses. Alternatively, the env proteins may be modified, synthetic or chimeric env constructs, or may be obtained from non-retroviruses, such as vesicular stomatitis virus and HVJ virus. Specific non-limiting examples include the envelope of Moloney Murine Leukemia Virus (MMLV), Rous Sarcoma Virus, Baculovirus, Jaagsiekte Sheep Retrovirus (JSRV) envelope protein, and the feline endogenous virus RD114; gibbon ape leukemia virus (GALV) envelope; baboon endogenous virus (BaEV) envelope; simian sarcoma associated virus (SSAV) envelope; amphotropic murine leukemia virus (MLV-A) envelope; human immunodeficiency virus envelope; avian leukosis virus envelope; the endogenous xenotropic NZB viral envelopes; and envelopes of the paramyxoviridiae family such as, but not limited to the HVJ virus envelope.

In certain embodiments, The APCs may include, for example, any one or more of macrophages, dendritic cells, langerhans cells, B lymphocytes (B cells), and T lymphocytes (T cells). In certain embodiments, the APCs are dendritic cells.

In certain embodiments, the APCs are B cells. In certain embodiments, the B cells are isolated by CD19 or CD20 selection.

In certain embodiments, the B cell is activated. In some embodiments, B cells can be activated by incubation with compounds such as, but not limited to, CD40L, IL-21, and/or IL-4. In certain embodiments, the B cells are activated by incubation with CD40L. B cell stimulator cells such as CD40 positive L cells and/or EL4B5 cells can also be used to activate the B cell. Additionally, other kinds of cells, which were also present in a sample from a subject from which the B cells were obtained, could still be present in a B cell culture. When present in B cell culturing conditions, such non-B cells are typically less capable of proliferating as compared to B cells, so that the number of such contaminating cells will typically decline in time. Preferably, at least 70% of the cells of a B cell culture are B cells. More preferably, at least 75%, 80%, 85%, 90% or 95% of the cells of said B cell culture are B cells. In one embodiment, B cells and B cell stimulator cells such as CD40 positive L cells and/or EL4B5 cells are essentially the only kinds of cell present in a B cell culture as used in the invention. In some embodiments, essentially all cells of said B cell culture are B cells.

In certain embodiments, B cells further cultured with Bcl-6, Bcl-XL, BCL-2, MCL1, STAT-5, and/or an activator of at least one of the JAK/STAT pathway, PI3K-AKT signaling pathway, BCR signaling pathway, or BAFF-BAFFR signaling pathway.

In certain embodiments, dendritic cells can be prepared from mononuclear cells by proliferating and/or differentiating mononuclear cells from obtained blood into dendritic cells. Mononuclear cells may be cultured in a medium containing interleukin-4 (IL-4) and may be differentiated into immature dendritic cells. The obtained immature dendritic cells may be cultured in a medium containing tumor necrosis factors-α (TNF-α) and may be differentiated into mature dendritic cells. Dendritic cells can also be generated using the plastic adherence method. For the plastic adherence method, entire mononuclear cells can be seeded and cultured in a cell culture container for 1 to 2 hours, and cells attached to the bottom can be used.

Dendritic cells can be activated by the update of antigen.

The MHC molecule that presents the peptide(s) can be any MHC molecule expressed by the subject. In some embodiments, the class I MHC polypeptide is a human class I MHC polypeptide selected from the group consisting of HLA-A, HLA-B, HLA-C, HLA-E, HLA-F, and HLA-G. In another specific embodiment, the class I MHC polypeptide is a murine class I MHC polypeptide selected from the group consisting of H-2K, H-2D, H-2L, H-2Q, H-2M, and H-2T. In some embodiments, the class II MHC polypeptide selected from the group consisting of HLA-DP, HLA-DR, and HLA-DQ. In some embodiments, the class II MHC polypeptide selected from the group consisting of HLA-DMA, HLA-DOA, HLA-DPA, HLA-DQA and HLA-DRA.

Lymphocytes

In one aspect, described herein are methods for expanding antigen-specific lymphocytes ex vivo comprising expanding lymphocytes in a sample obtained from a subject or lymphocytes isolated from such sample, wherein expanding comprises adding one or more peptides during expansion, wherein each of said peptide(s) comprises a different antigen and wherein antigen-specific lymphocytes are expanded. In one aspect, the invention provides a method to expand antigen-specific lymphocytes, to allow for increased immunogenic activity (e.g., greater and/or longer activity).

In one aspect, described herein are methods for expansion of antigen-specific lymphocytes ex vivo comprising a) expanding lymphocytes in a sample obtained from a subject or lymphocytes isolated from such sample, wherein expanding comprises at least two phases of expansion, and b) adding one or more peptides during at least one of the at least two phases of expansion, wherein each of said peptide(s) comprises a different antigen and wherein antigen-specific lymphocytes are expanded. In one aspect, the invention provides a method to expand antigen-specific lymphocytes, to allow for increased immunogenic activity (e.g., greater and/or longer activity).

The sample containing the lymphocytes can be obtained from numerous sources in the subject, including but not limited to such as but not limited to, a tissue (including tumor tissue. viral infected tissue, tissue at the site of inflammation, site of lymphocyte infiltration, and site of leukocyte infiltration), thymus, tumor tissue (e.g., samples, fragments), or enzymatically digested tissue, dissociated/suspended cells, a lymph node sample, or a bodily fluid sample (e.g., blood, ascites, lymph). Exemplary tissues include skin, adipose tissue, cardiovascular tissue such as veins, arteries, capillaries, valves; neural tissue, bone marrow, breast, gastrointestinal, pulmonary tissue, ocular tissue such as corneas and lens, cartilage, bone, and mucosal tissue.

The sample can be an untreated, enzymatically treated, and/or dissociated/suspended to form a cell suspension. When the sample is enzymatically treated, non-limited examples of enzymes that can be used include collagenase, dispase, hyaluronidase, liberase, and deoxyribonuclease (DNase).

In one aspect, the invention provides a method to expand antigen-specific lymphocytes, to allow for increased immunogenic activity (e.g., greater and/or longer activity). Lymphocytes are one subtype of white blood cells in the immune system.

In certain embodiments, lymphocytes for use in the invention include tumor-infiltrating immune cells. Tumor-infiltrating immune cells consist of both mononuclear and polymorphonuclear immune cells, (i.e., T cells, B cells, natural killer cells, macrophages, neutrophils, dendritic cells, mast cells, eosinophils, basophils, etc.) in variable proportions. In certain embodiments, lymphocytes for use in the invention include tumor-infiltrating lymphocytes (TILs). TILs are white blood cells that have left the bloodstream and migrated towards a tumor. TILs can often be found in the tumor stroma and within the tumor itself. In certain embodiments, TILs are "young" T cells or minimally cultured T cells. In certain embodiments, the young cells have a reduced culturing time (e.g., between about 22 to about 32 days in total). In certain embodiments, the lymphocytes express CD27.

In certain embodiments, lymphocytes for use in the invention include peripheral blood lymphocytes (PBLs). In certain embodiments, lymphocytes for use in the invention include T lymphocytes (a.k.a T cells) and/or natural killer cells (a.k.a NK cells).

In certain embodiments, the lymphocytes may be autologous, allogeneic, syngeneic, or xenogeneic with respect to the subject. In certain embodiments, the lymphocytes are autologous in order to reduce an immunoreactive response against the lymphocyte when reintroduced into the subject for immunotherapy treatment.

In certain embodiments, the T cells are CD8+ T cells. In certain embodiments, the T cells are CD4+ cells. In certain embodiments, the CD8+ T cells are isolated prior to incubation with the peptide(s) and/or APC's presenting peptide(s). In certain embodiments, the CD8+ T cells are not isolated prior to incubation with the peptide(s) and/or APC's presenting peptide(s). In certain embodiments, the CD4+ T cells are isolated prior to incubation with the peptide(s) and/or APC's presenting peptide(s). In certain embodiments, the CD4+ T cells are not isolated prior to incubation with the peptide(s) and/or APC's presenting peptide(s).

In certain embodiments, the NK cells are CD 16+CD56+ and/or CD57+ NK cells. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

Conditions appropriate for lymphocyte culture include an appropriate media (e.g., Minimal Essential Media (MEM), RPMI Media 1640, Lonza RPMI 1640, Advanced RPMI, Clicks, AIM-V, DMEM, a-MEM, F-12, TexMACS, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion).

Examples of other additives for lymphocyte expansion include, but are not limited to, surfactant, piasmanate, pH buffers such as HEPES, and reducing agents such as N-acetyl-cysteine and 2-mercaptoethanol, Antibiotics (e.g., penicillin and streptomycin), are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2).

Specific tumor reactivity of the expanded TILs can be tested by any method known in the art, e.g., by measuring cytokine release (e.g., interferon-γ) following co-culture with tumor cells. In one embodiment, the autologous ACT method comprises enriching cultured TILs for CD8+ T cells prior to rapid expansion of the cells. Following culture of the TILs in IL-2, the T cells are depleted of CD4+ cells and enriched for CD8+ cells using, for example, a CD8 microbead separation (e.g., using a CliniMACS<plus>CD8 microbead system (Miltenyi Biotec)). In another embodiment, the autologous ACT method comprises enriching cultured TILs for CD4+ T cells prior to rapid expansion of the cells. Following culture of the TILs in IL-2, the T cells are depleted of CD8+ cells and enriched for CD4+ cells using, for example, a CD4 microbead separation (e.g., using a CliniMACS<plus>CD4 microbead system (Miltenyi Biotec)). In some embodiments, a T cell growth factor that promotes the growth and activation of the autologous T cells is administered to the mammal either concomitantly with the autologous T cells or subsequently to the autologous T cells. The T cell growth factor can be any suitable growth factor that promotes the growth and activation of the autologous T cells.

Methods of Treatment

In a related aspect, disclosed herein is a method for treating a tumor in a subject in need thereof comprising administering to the subject the effective amount of a population of antigen-specific lymphocytes produced by the methods disclosed herein. In certain embodiments the tumors are solid tumors. In certain embodiments, the tumors are liquid tumors (e.g., blood cancers).

Non-limiting examples of tumors treatable by the methods described herein include, for example, carcinomas, lymphomas, sarcomas, blastomas, and leukemias. Non-limiting specific examples, include, for example, breast cancer, pancreatic cancer, liver cancer, lung cancer, prostate cancer, colon cancer, renal cancer, bladder cancer, head and neck carcinoma, thyroid carcinoma, soft tissue sarcoma, ovarian cancer, primary or metastatic melanoma, squamous cell carcinoma, basal cell carcinoma, brain cancers of all histopathologic types, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, cancers associated with viral infection (such as but not limited to human papilloma virus (HPV) associated tumors (e.g., cancer cervix, vagina, vulva, head and neck, anal, and penile carcinomas)), Ewing's tumor, leiomyosarcoma, Ewing's sarcoma, rhabdomyosarcoma, carcinoma of unknown primary (CUP), squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, glioblastoma, astrocytoma, medulloblastoma, craniopharyngioma, ependymoma, pinealoma, hemangioblastoma, acoustic neuroma, oligodendroglioma, meningioma, retinoblastoma, leukemia, neuroblastoma, small cell lung carcinoma, bladder carcinoma, lymphoma, multiple myeloma, medullary carcinoma, B cell lymphoma, T cell lymphoma, NK cell lymphoma, large granular lymphocytic lymphoma or leukemia, gamma-delta T cell lymphoma or gamma-delta T cell leukemia, mantle cell lymphoma, myeloma, leukemia, chronic myeloid leukemia, acute myeloid leukemia, chronic lymphocytic leukemia, acute lymphocytic leukemia, hairy cell leukemia, hematopoietic neoplasias, thymoma, sarcoma, non-Hodgkin's lymphoma, Hodgkin's lymphoma, Epstein-Barr virus (EBV) induced malignancies of all types including but not limited to EBV-associated Hodgkin's and non-Hodgkin's lymphoma, all forms of post-transplant lymphomas including post-transplant lymphoproliferative disorder (PTLD), uterine cancer, renal cell carcinoma, hepatoma, hepatoblastoma. Cancers that may treated by methods and compositions described herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The anti-tumor responses after treatment with the lymphocytes expanded by the methods disclosed herein may be determined in xenograft tumor models. Tumors may be established using any human cancer cell line expressing the tumor associated antigen presented by the viral particles. In order to establish xenograft tumor models, about $5\times10^6$ viable cells, may be injected, e.g., s.c., into nude athymic mice using for example Matrigel (Becton Dickinson). The endpoint of the xenograft tumor models can be determined based on the size of the tumors, weight of animals, survival time and histochemical and histopathological examination of the cancer, using methods known to one skilled in the art.

In a related aspect, disclosed herein is a method for treating infectious and/or zoonotic diseases in a subject in need thereof comprising administering to the subject the effective amount of a population of antigen-specific lymphocytes produced by the methods disclosed herein. Infectious diseases are caused by pathogenic microorganisms, such as bacteria, viruses, parasites or fungi; the diseases can be spread, directly or indirectly, from one person to another. Zoonotic diseases are infectious diseases of animals that can cause disease when transmitted to humans. Examples of infectious and/or zoonotic diseases include, but are not limited to acute and chronic infectious processes can result in obstruction of body passageways including for example, obstructions of the male reproductive tract (e.g., strictures due to urethritis, epididymitis, prostatitis); obstructions of the female reproductive tract (e.g., vaginitis, cervicitis, pelvic inflammatory disease (e.g., tuberculosis, gonococcus, *chlamydia, enterococcus* and syphilis); urinary tract obstructions (e.g., cystitis, urethritis); respiratory tract obstructions (e.g., chronic bronchitis, tuberculosis, other mycobacterial infections (MAI, etc.), anaerobic infections, fungal infections and parasitic infections) and cardiovascular obstructions (e.g., mycotic aneurysms and infective endocarditis).

In certain embodiments, administration of the lymphocytes generated by the methods as disclosed herein can be used to treat viral infections and/or tumors resulting from viral infection.

Exemplary viruses include, but are not limited herpesviruses such as the simplexviruses (e.g. human herpesvirus-1 (HHV-1), human herpesvirus-2 (HHV-2)), the varicelloviruses (e.g. human herpesvirus-3 (HHV-3, also known as varicella zoster virus)), the lymphocryptoviruses (e.g. human herpesvirus-4 (HHV-4, also known as Epstein Barr virus (EBV))), the cytomegaloviruses (e.g. human herpesvirus-5 (HHV-5), also known as human cytomegalovirus (HCMV)), the roseoloviruses (e.g. human herpesvirus 6 (HHV-6), human herpesvirus 7 (HHV-7)), the rhadinovirues (e.g. human herpesvirus 8 (HHV-8, also known as Kaposi's Sarcoma associated herpesvirus (KSHV)); poxviruses such as orthopoxviruses (e.g. cowpoxvirus, monkeypoxvirus, vaccinia virus, variola virus), parapoxviruses (e.g. bovine popular stomatitis virus, orf virus, pseudocowpox virus), molluscipoxviruses (e.g. molluscum contagiosum virus), yatapoxviruses (e.g., tanapox virus, yaba monkey tumor virus); adenoviruses (e.g. Human adenovirus A (HAdV-A), Human adenovirus B (HAdV-B), Human adenovirus C (HAdV-C), Human adenovirus D (HAdV-D), Human adenovirus E (HAdV-E), Human adenovirus F (HAdV-F)); papillomaviruses (e.g. human papillomavirus (HPV); parvoviruses (e.g. B19 virus); hepadnoviruses (e.g., Hepatitis B virus (HBV)); retroviruses such as deltaretroviruses (e.g. primate T-lymphotrophic virus 1 (HTLV-1) and primate T-lymphotrophic virus 2 (HTLV-2)) and lentiviruses (e.g. Human Immunodeficiency Virus 1 (HIV-1) and Human Immunodeficiency Virus 2 (HIV-2); reoviruses such the orthoreoviruses (e.g. mammalian orthoreovirus (MRV)), the orbviruses (e.g. African horse sickness virus (AHSV), Changuinola virus (CORV), Orungo virus (ORUV), and the rotaviruses (e.g. rotavirus A (RV-A) and rotavirus B (RV-B)); filoviruses such as the "Marburg-like viruses" (e.g. MARV), the "Ebola-like viruses" (e.g. CIEBOV, REBOV, SEBOV, ZEBOV); paramyxoviruses such as respiroviruses (e.g. human parainfluenza virus 1 (HPIV-1), human parainfluenza virus 3 (HPIV-3), rubulaviruses (e.g. human parainfluenza virus 2 (HPIV-2), human parainfluenza virus 4

(HPIV-4)), mumps virus (MuV)), and morbilliviruses (e.g. measles virus); pneumoviruses (e.g. human respiratory syncitial virus (HSCV); rhabdoviruses such as the vesiculoviruses (e.g. vesicular stomatitis virus), the lyssaviruses (e.g., rabies virus); orthomyxoviruses (e.g. Influenza A virus, Influenza B virus, Influenza C virus); bunyaviruses (e.g. California encephalitis virus (CEV)); hantaviruses (e.g. Black Creek Canal virus (BCCV), New York virus (NYV), Sin Nombre virus (SNV)); picornaviruses including the enteroviruses (e.g. human enterovirus A (HEV-A), human enterovirus B (HEV-B), human enterovirus C (HEV-C), human enterovirus D (HEV-D), poliovirus (PV)), the rhinoviruses (e.g. human rhinovirus A (HRV-A), human rhinovirus B (HRV-B)), the hepatoviruses (e.g. Hepatitis A virus (HAV)); caliciviruses including the "Norwalk-like viruses" (e.g. Norwalk Virus (NV), and the "Sapporo-like viruses" (e.g. Sapporo virus (SV)); togaviruses including alphaviruses (e.g. Western equine encephalitis virus (WEEV) and Eastern equine encephalitis virus (EEEV)) and rubiviruses (e.g. Rubella virus); flaviviruses (e.g. Dengue virus (DENV), Japanese encephalitis (JEV), St. Louis encephalitis virus (SLEV), West Nile virus (WNV), Yellow fever virus (YFV); arenaviruses (e.g. lassa virus); coronaviruses (e.g. the severe acute respiratory syndrome (SARS)-associated virus); and hepaciviruses (e.g. Hepatitis C virus (HCV)).

In certain embodiments, a population of antigen-specific lymphocytes produced by the methods disclosed herein are administered with an additional therapeutic agent. The population of antigen-specific lymphocytes described herein can be administered to a subject either simultaneously with or before (e.g., 1-30 days before) the additional therapeutic (including but not limited to small molecules, antibodies, or cellular reagents) that acts to elicit an immune response (e.g., to treat cancer) in the subject. When co-administered the an additional therapeutic, the lymphocytes and the additional therapeutic agent may be simultaneously or sequentially (in any order). Suitable therapeutically effective dosages for each agent may be lowered due to the additive action or synergy.

In certain embodiments, a population of neo-antigen-specific lymphocytes produced by the methods disclosed herein can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The inhibitory treatments described herein can be also combined with other treatments that possess the ability to modulate NKT function or stability, including but not limited to CD1d, CD1d-fusion proteins, CD1d dimers or larger polymers of CD1d either unloaded or loaded with antigens, CD1d-chimeric antigen receptors (CD1d-CAR), or any other of the five known CD1 isomers existing in humans (CD1a, CD1b, CD1c, CD1e), in any of the aforementioned forms or formulations, alone or in combination with each other or other agents.

Lymphodepletion prior to adoptive transfer of antigen-specific lymphocytes can plays a role in enhancing treatment efficacy by eliminating regulatory T cells and competing elements of the immune system. Accordingly, some embodiments of the invention utilize a lymphodepletion step (sometimes also referred to as "immunosuppressive conditioning") on the subject prior to the introduction of the antigen-specific lymphocytes of the invention. Lymphodepletion can achieved by administering compounds such as, but not limited to, fludarabine or cyclophosphamide (the active form being referred to as mafosfamide) and combinations thereof. Such methods are described in Gassner, et al., Cancer Immunol. Immunother. 2011, 60, 75-85, Muranski, et al., Nat. Clin. Pract. Oncol., 2006, 3, 668-681, Dudley, et al., J. Clin. Oncol. 2008, 26, 5233-5239, and Dudley, et al., J. Clin. Oncol. 2005, 23, 2346-2357, all of which are incorporated by reference herein in their entireties for all purposes.

In certain embodiments, the subject is immunodepleted prior to treatment with the antigen-specific lymphocytes. For example, the subject can be pre-treated with non-myeloablative chemotherapy prior to an infusion of lymphocytes generated by the methods described herein. In one embodiment, a population of antigen-specific lymphocytes can be administered by infusion. In one embodiment, the non-myeloablative chemotherapy can be cyclophosphamide 60 mg/kg/d for 2 days (days 27 and 26 prior to antigen-specific lymphocyte infusion) and fludarabine 25 mg/m2/d for 5 days (days 27 to 23 prior to antigen-specific lymphocyte infusion). In one embodiment, after non-myeloablative chemotherapy and antigen-specific lymphocyte infusion (at day 0) according to the present disclosure, the subject can receive an intravenous infusion of IL-2 intravenously at 720,000 IU/kg every 8 hours to physiologic tolerance. In certain embodiments, the population of antigen-specific lymphocyte cab be used for treating cancer in combination with IL-2, wherein the IL-2 is administered after the population of antigen-specific lymphocytes.

Therapeutic methods described herein can be combined with additional immunotherapies and therapies. For example, when used for treating cancer, the lymphocytes described herein can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors described herein include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In some embodiments, the inhibitors described herein can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Compositions as disclosed herein can also include adjuvants such as aluminum salts and other mineral adjuvants, tensoactive agents, bacterial derivatives, vehicles and cytokines. Adjuvants can also have antagonizing immunomodulating properties. For example, adjuvants can stimulate Th1 or Th2 immunity. Compositions and methods as disclosed herein can also include adjuvant therapy.

Pharmaceutical Compositions, Dosage Forms and Administration

Also disclosed herein are pharmaceutical compositions comprising population of neo-antigen-specific lymphocytes produced by the methods described herein and a pharmaceutically acceptable carrier and/or excipient. In addition, disclosed herein are pharmaceutical dosage forms comprising the viral particle described herein. As discussed herein, the pseudotyped viral particles described herein can be used for various therapeutic applications (in vivo and ex vivo) and as research tools.

Pharmaceutical compositions based on the population of neo-antigen-specific lymphocytes produced by the methods disclosed herein can be formulated in any conventional manner using one or more physiologically acceptable carriers and/or excipients. The lymphocytes may be formulated for administration by, for example, injection, parenteral, vaginal, rectal administration, or by administration directly to a tumor.

The pharmaceutical compositions can be formulated for parenteral administration by injection, e.g. by bolus injection or continuous infusion. Formulations for injection can be presented in a unit dosage form, e.g. in ampoules or in multi-dose containers, with an optionally added preservative. The pharmaceutical compositions can further be formulated as suspensions, solutions or emulsions in oily or aqueous vehicles, and may contain other agents including suspending, stabilizing and/or dispersing agents.

Pharmaceutical forms suitable for injectable use can include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid. It must be stable under the conditions of manufacture and certain storage parameters (e.g. refrigeration and freezing) and must be preserved against the contaminating action of microorganisms, such as bacteria and fungi.

If formulations disclosed herein are used as a therapeutic to boost an immune response in a subject, a therapeutic agent can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A carrier can also be a solvent or dispersion medium containing, for example, water, saline, polyol (for example, glycerol, propylene glycol, and liquid polyethylene glycol, and the like), suitable mixtures thereof, and vegetable oils. The prevention of the action of microorganisms can be brought about by various antibacterial and antifungal agents known in the art. In many cases, it will be preferable to include isotonic agents, for example, sugars or sodium chloride.

Upon formulation, solutions can be administered in a manner compatible with the dosage formulation and in such amount as is therapeutically effective. Dose ranges and frequency of administration can vary depending on the nature of the population of the population of neo-antigen-specific lymphocytes produced by the methods described herein and the medical condition as well as parameters of a specific patient and the route of administration used.

In some embodiments, the population of neo-antigen-specific lymphocytes produced by the methods described herein can be administered to a subject at a dose ranging from about $10^7$ to about $10^{12}$. A more accurate dose can also depend on the subject in which it is being administered. For example, a lower dose may be required if the subject is juvenile, and a higher dose may be required if the subject is an adult human subject. In certain embodiments, a more accurate dose can depend on the weight of the subject.

EXAMPLE SECTION

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Materials and Methods

Identification of Non-Synonymous Tumor Mutations

Genomic DNA from cryopreserved tumor tissue and matched peripheral blood mononuclear cells (PBMC) was isolated using DNeasy kit (Qiagen) and subjected to whole exome capture and paired-end sequencing using the HiSeq2500 Illumina platform. Somatic variants were called from the exome reads and the reference human genome hg19 by using a software pipeline composed of a genome mapping tool, fetchGWI27, followed by a detailed sequence alignment tool, align0. Non-deterministic predictors of any kind were avoided and the route of minimizing false negative was prioritized and a cross-comparison with GATK as consensual variant detection/prediction method reached over 96% agreement. Variations present in the tumor samples and absent from the corresponding blood samples were assumed to be somatic.

Isolation of Neo-Antigen Specific T Cells

Circulating and tumor-infiltrating neo-antigen specific CD8+ T cells were FACS sorted using in-house reversible multimers (NTAmers) (see U.S. Pat. No. 10,023,657, incorporated herein in its entirety for all purposes).

Neo-Antigen Prediction

Binding predictions to class-I HLA alleles for all candidate peptides incorporating somatic non-synonymous mutations were performed using the netMHC algorithm v3.4 (Lundegaard et al., Nucleic Acids Research 36, W509-512 (2008)). Candidate neo-antigen peptides (i.e., mutant 9-mer and 10-mer peptide sequences containing the somatically altered residue at each possible position) with a predicted binding affinity of ≤500 nM, and their wild-type native predicted peptides were synthesized (at >90% HPLC purity) at the Protein and Peptide Chemistry Facility (PPCF), University of Lausanne.

TILs Expansion and Interrogation

Conventional tumor-infiltrating lymphocytes (TILs) were generated from tumor enzymatic digestions and tumor fragments as elsewhere described (Dudley et al., J Immunother 2008). Specifically, single-cell tumor suspensions were plated in p24-well plates at a density of $1\times10^6$ cells/well in complete medium (CM), consisting in RMPI 1640 Glutamax (Gibco) supplemented with 8% human serum AB (Biowest), 1% Hepes 1M (Amimed), 1% non-essential amino acids (Invitrogen), 1% Sodium Pyruvate 100 mM (Invitrogen), 2 mM L-Glutamine (BioConcept), 1% 100 U/mL Penicillin-100 μg/mL Streptomycin (BioConcept)+ 1‰ β-mercaptoethanol 50 mM (Invitrogen), 100 μg/mL kanamycin and 6000 IU/mL hrIL-2 (GlaxoSmithKline). Alternatively, single tumor pieces of 1-2 $mm^3$ were placed in each well of a p24-well and cultured in CM. Plates were placed at 37° C. and 5% $CO_2$ and half of the medium changed 3 times per week starting from day 2 after culture initiation, whether or not lymphocytes growth was visible. TILs cultures were maintained at a density of $1\times10^6$ cells/mL during typically 2-3 weeks, after which cells were collected, pooled. This population of cells are pre-REP TILs.

Primed TILs were generated like conventional TILs with the following modification: a pool of predicted peptides at 1 μM each was added to the culture at day 0 for tumor digests and a day 0, 2 and 4 for tumor fragments (up to a maximum of 50 peptides/pool and a final concentration of 0.5% DMSO (Chevalier, Bobisse et al, Oncoimm 2015). The priming takes place at the initiation of the pre-REP phase. Due to tumor material restrictions, few replicates (wells) per pool were plated. When described, CM was supplemented with 10 μg/mL anti-PD1 mAb (eBiosciences) and 10 μg/mL anti-CTLA-4 mAb (Ipilimumab, Bristol-Myers) during the whole period of TIL culture (i.e., FIGS. 1 and 2).

T cell reactivity against predicted neo-antigens was tested by IFNγ ELISpot on pre-REP TILs. Positivity was confirmed in ≥2 independent experiments. ELISpot assays were performed using pre-coated 96-well ELISpot plates (Mabtech) and counted with Bioreader-6000-E (BioSys) (Harari et al., The Journal of Experimental Medicine 205, 63-77 (2008)).

Peptides used in Example 1 and 2 (below) are presented in Table 1.

TABLE 1

Exemplary Peptides(s) used in Examples 1 and 2. Underlined peptides were used in the stimulation assays (i.e., for validation purposes).

Figure 1B:
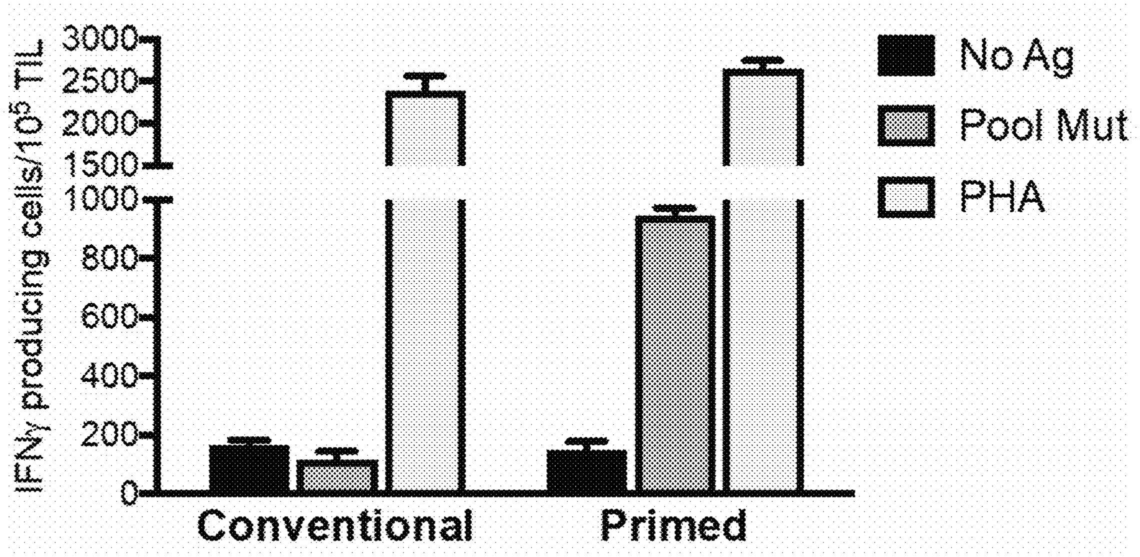
Figure 2A:
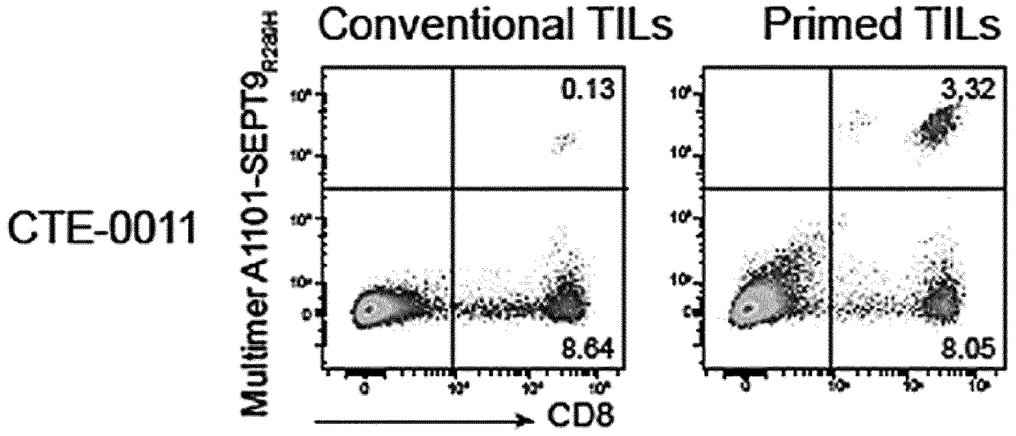
FIGS. 2A-2B show representative examples of conventional (IL-2 alone) and primed (IL-2+pools of private predicted neo-antigens) TILs, interrogated for the presence of neo-antigen-specific TILs by peptide-MHC multimer staining. TIL cultures from ovarian cancer patients CTE-0011 (FIG. 2A) and CTE-0013 (FIG. 2B) were initially interrogated with sets of predicted peptides and T cell responses evaluated by IFNγ ELISpot as shown in FIG. 1. After deconvolution and identification of single immunogenic peptides, validation was performed by multimer staining. For patient CTE-0011, $SEPT9_{R289H}$-specific T cells were detected at different frequencies in conventional and primed TILs; for patient CTE-0013, $HHAT_{L75F}$-specific T cells were revealed exclusively in primed TILs. These assays were performed with tumor fragments, in the presence of anti-PD1 and anti-CTLA4 antibodies. A pool of 50-100 private peptides (i.e., specifically predicted for this patient) was used. The peptides were from 9 to 10 amino acids long.
Figure 2B:
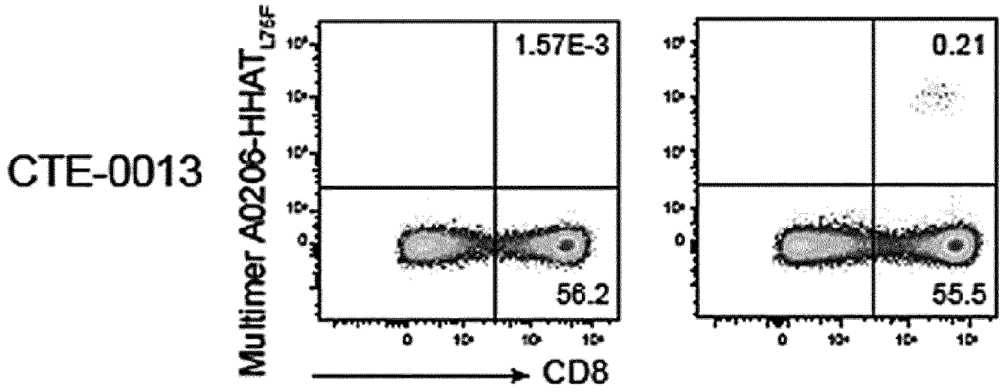

| | Peptides | | | | | | | |
|---|---|---|---|---|---|---|---|---|
| Associated Figures | | SEQ ID NO | | SEQ ID NO | | SEQ ID NO | | SEQ ID NO |
| Fig. 1A, 1B | **KQWLVWLFL** | 9 | FPFIAISCSY | 66 | WLFLGHGMVV | 129 | PPPPATTPF | 186 |
| Fig. 2B | LQLYRVLQCA | 10 | FPFIGISCSC | 67 | WLLLGPMVV | 130 | APTAVGPPL | 187 |
| CTE-0013 | VVLPPETRPI | 11 | LPVTDTSSVS | 68 | WVYEGTYLL | 131 | LVWLLLGPM | 188 |
| Wildtype: | YIMLLTNWRF | 12 | FPYSRRKFPA | 69 | VLLSATIFL | 132 | TYLLSATIF | 189 |
| KQWLVWLLL | LTNWRFTRGV | 13 | LTGLPHAPAL | 70 | LLSATIFLV | 133 | FPFIAISCS | 190 |
| (SEQ ID | WLVWLFLGHM | 14 | THVSDMSVVL | 71 | FLVFPFIAI | 134 | TPEEGGQAL | 191 |
| NO: 3) | LVWLFLGHMV | 15 | YRVLQCANLL | 72 | AISCSYGQV | 135 | LPVTDTSSV | 192 |

TABLE 1-continued

Exemplary Peptides(s) used in Examples 1 and 2. Underlined peptides were used in the stimulation assays (i.e., for validation purposes).

Figure 4:
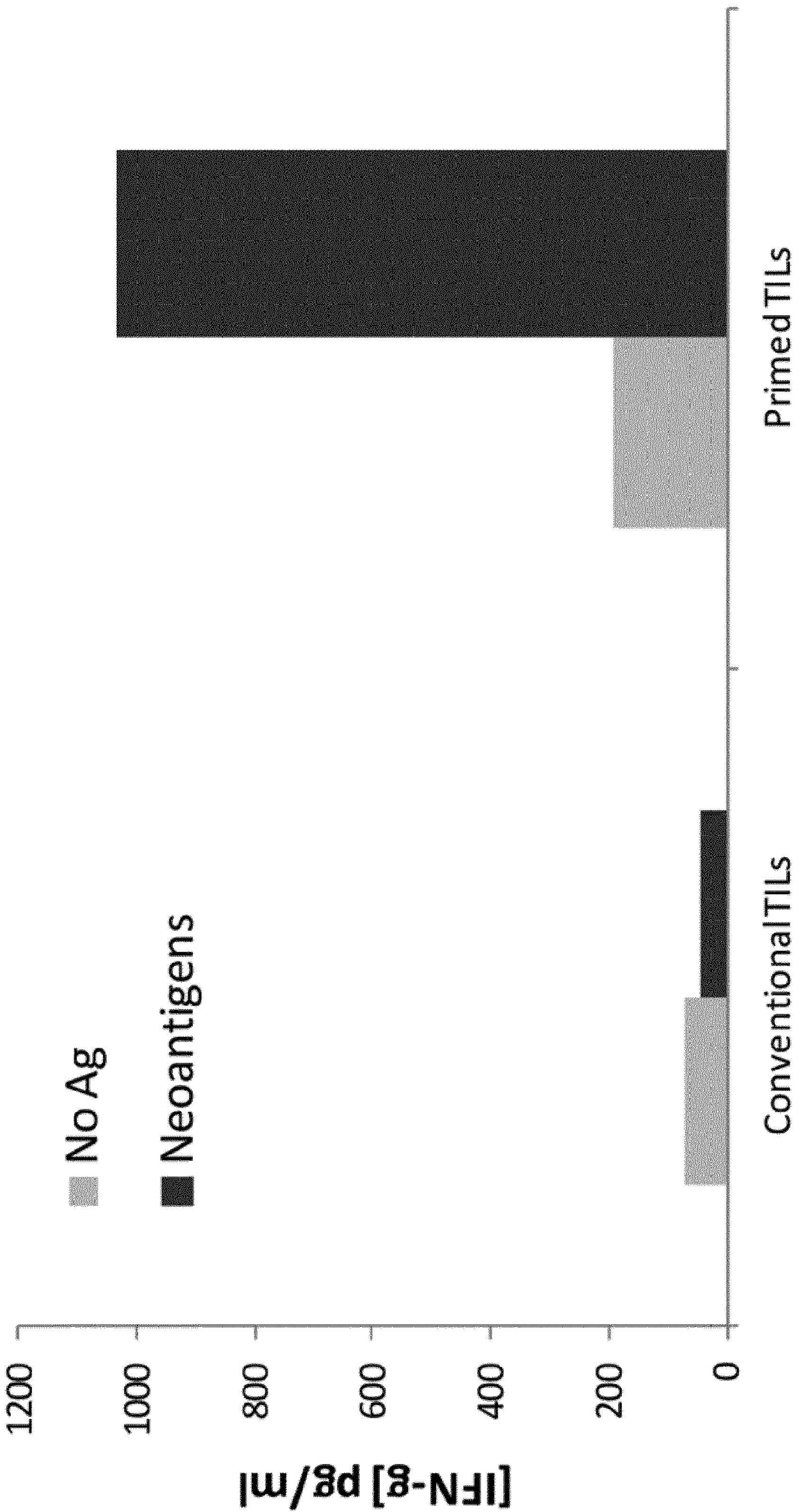
FIG. 4 shows representative examples of conventional (IL-2 alone) and primed (IL-2+pools of predicted neo-antigens) TILs from melanoma patient, interrogated for the presence of neo-antigen-specific TILs. A pool of 50-100 private peptides (i.e., specifically predicted for this patient) was used. The peptides were from 9 to 10 amino acids long.
Figure 5:
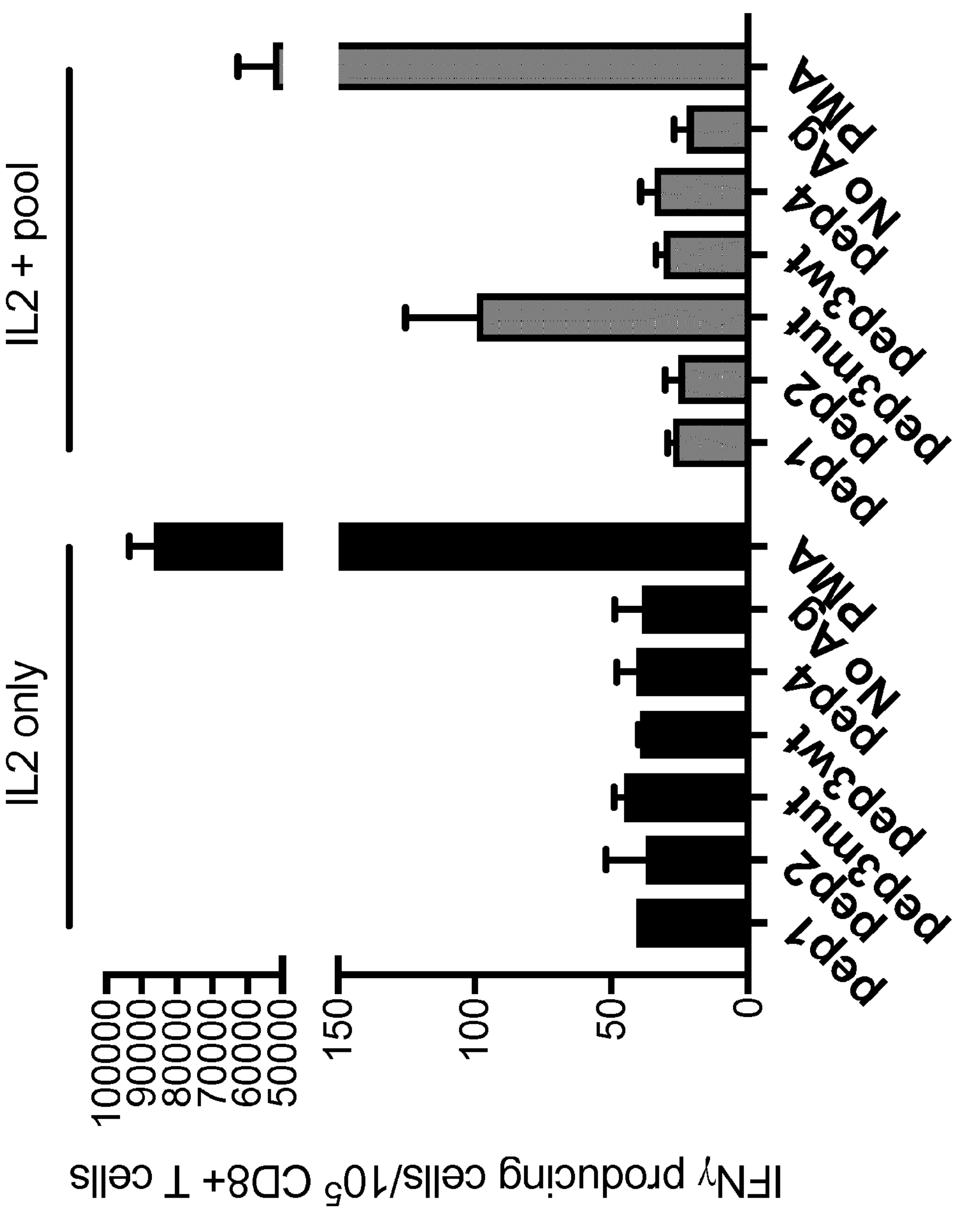
FIG. 5 shows expansion of neo-antigen-specific TILs from draining lymph nodes. Both "conventional" and "primed" TILs of patient CTE-0009 were generated from a single cell suspension of draining lymph nodes, following the methods described herein. Each culture was interrogated at day 14 by IFNγ-ELISPOT for the presence of neo-antigen T cell reactivities directed against one of the 4 predicted peptides and against the corresponding wild-type (wt) peptides. T cells specific for peptide #3 (and not the wt) were revealed only in the primed culture. PMA (50 ng/ml) was used as a positive control. PHA was used at 1 μg/ml.
Figure 8A:
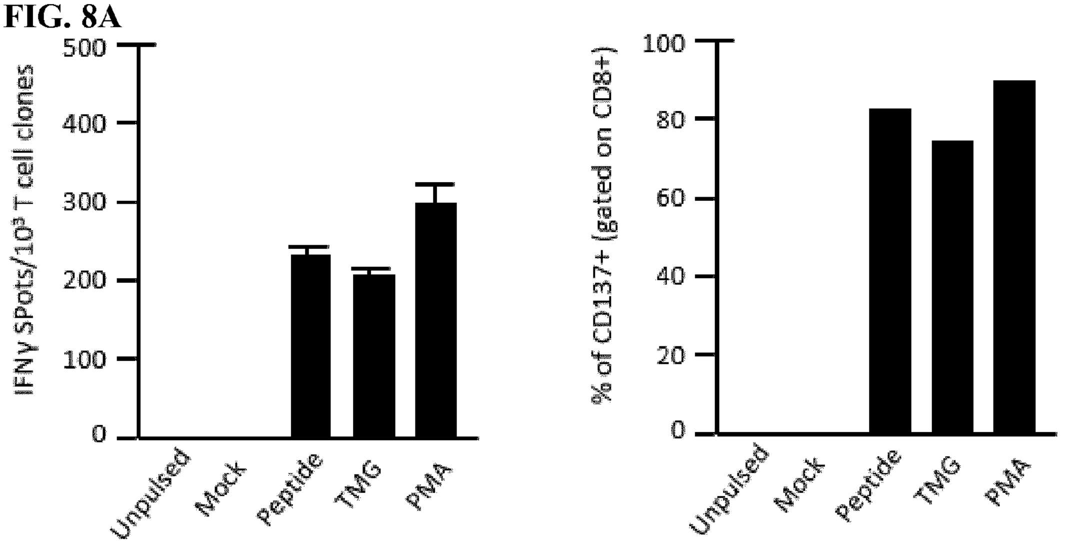
FIG. 8A-8C examines the generation of neo-antigen-specific TILs using isolated APCs to present the neo-antigens. In particular, B cells were either pulsed (i.e., preloaded/incubated as discussed in the methods) with peptide (Peptide) or transfected with tandem minigenes (TMG). All B cells were CD40-activated.
Figure 8B:
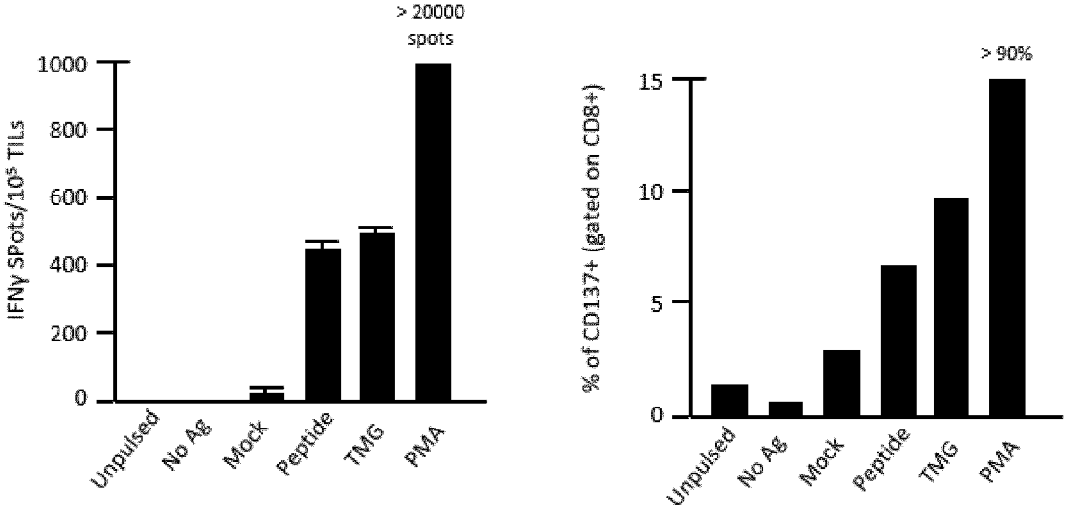
Figure 8C:
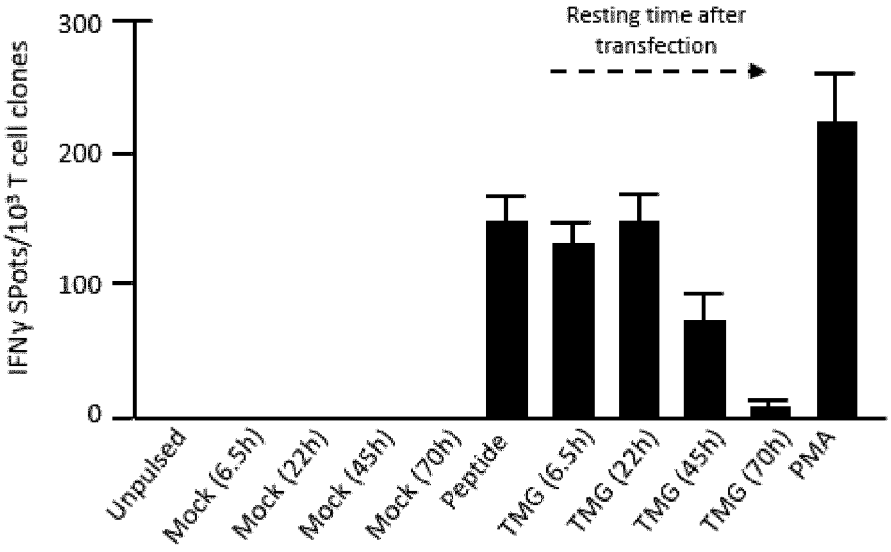
Figure 14:
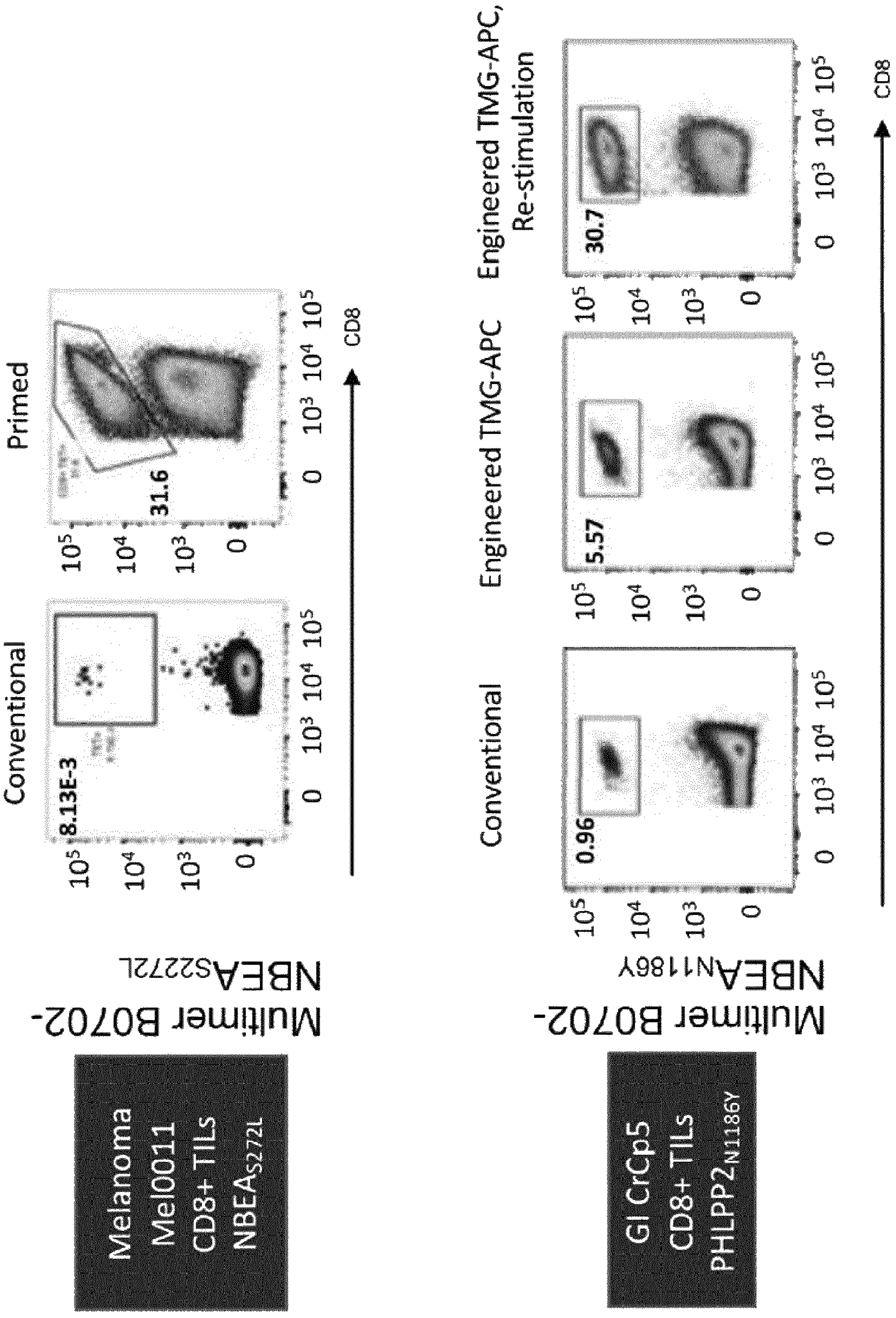
FIG. 14 shows a summary of the results of the invention with representative but non-limiting embodiments.
Figure 16A:
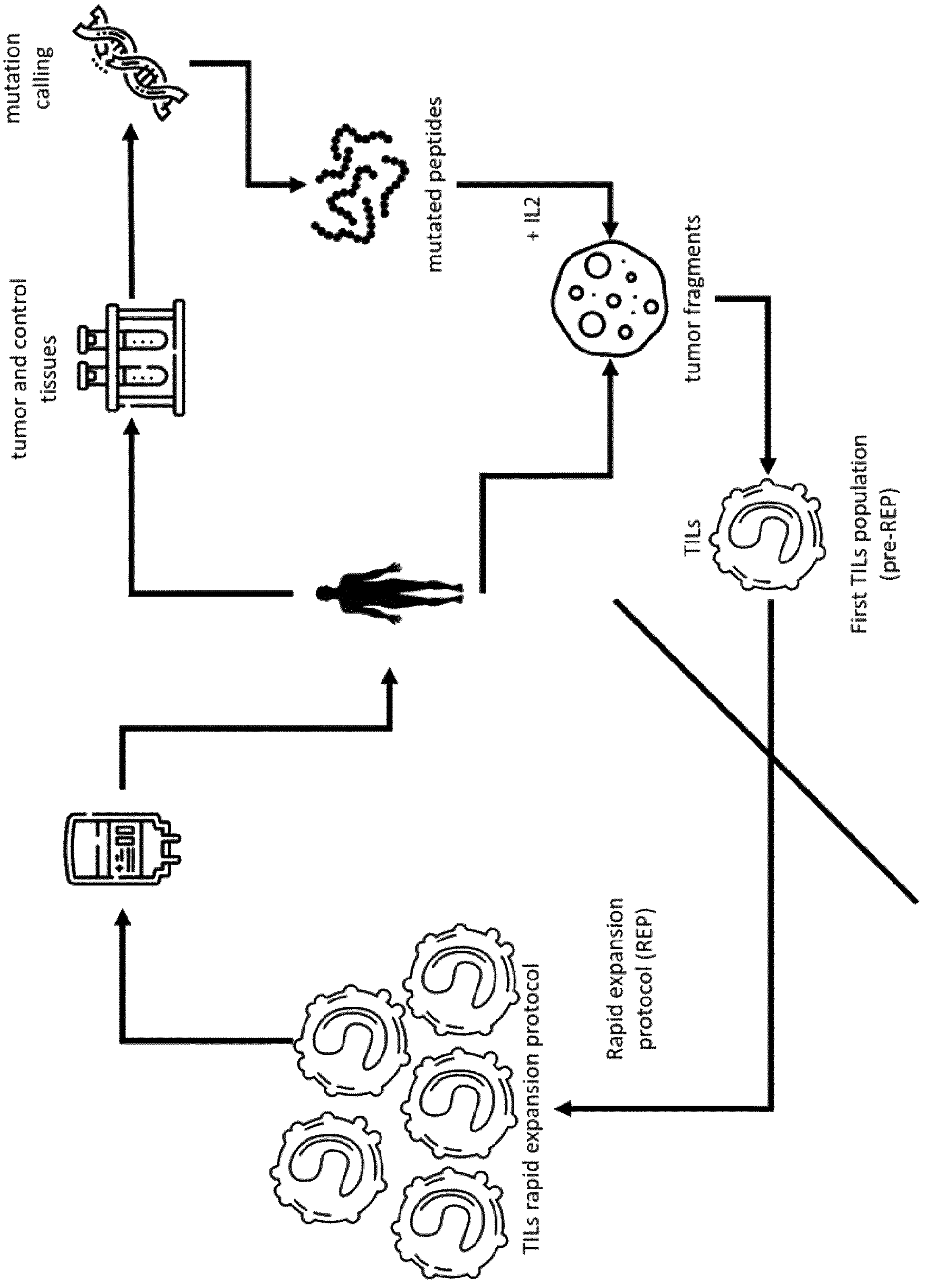
FIG. 16A-16G illustration non-limiting embodiments of the invention.
Figure 16B:
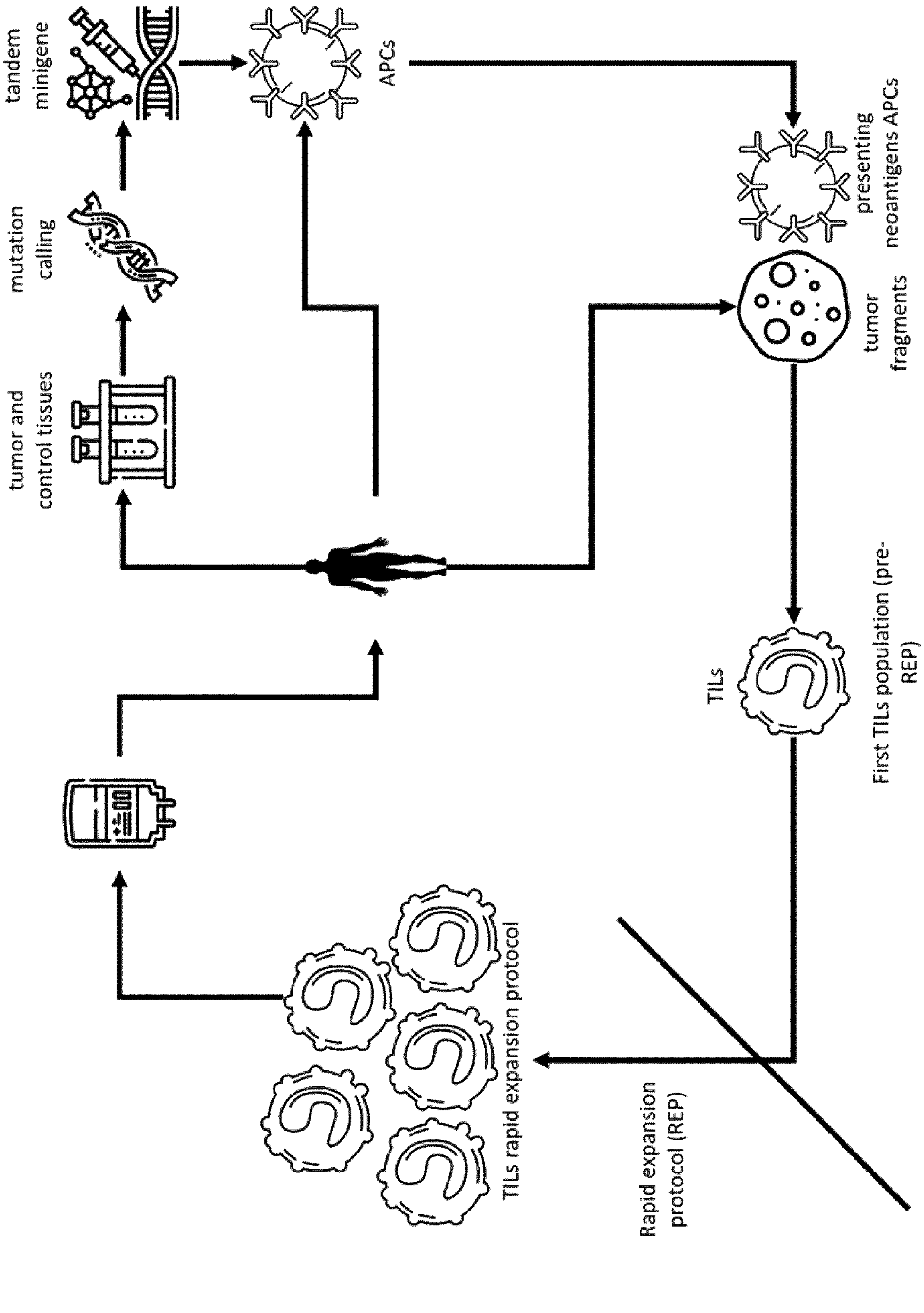
Figure 16C:
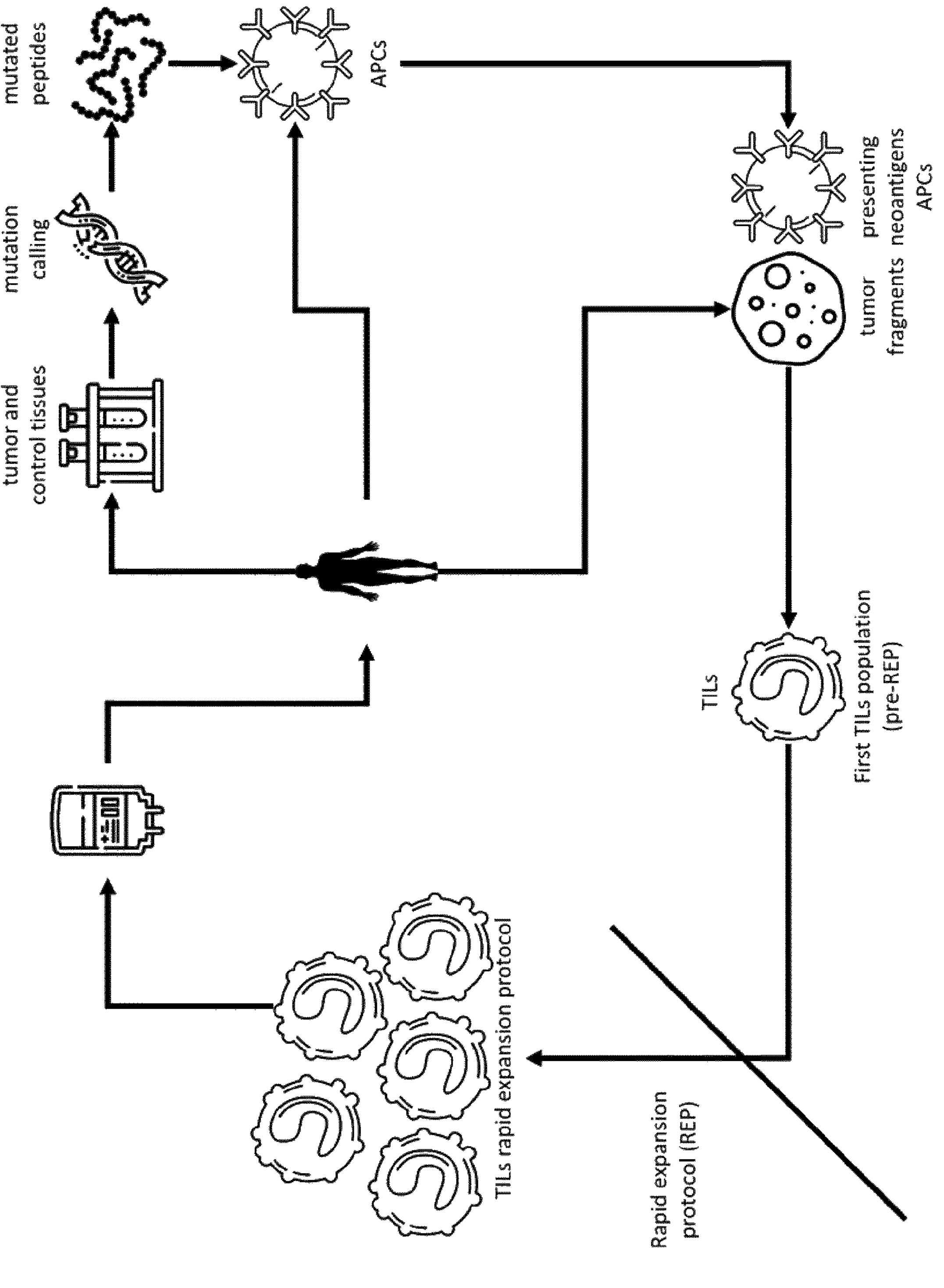
Figure 16D:
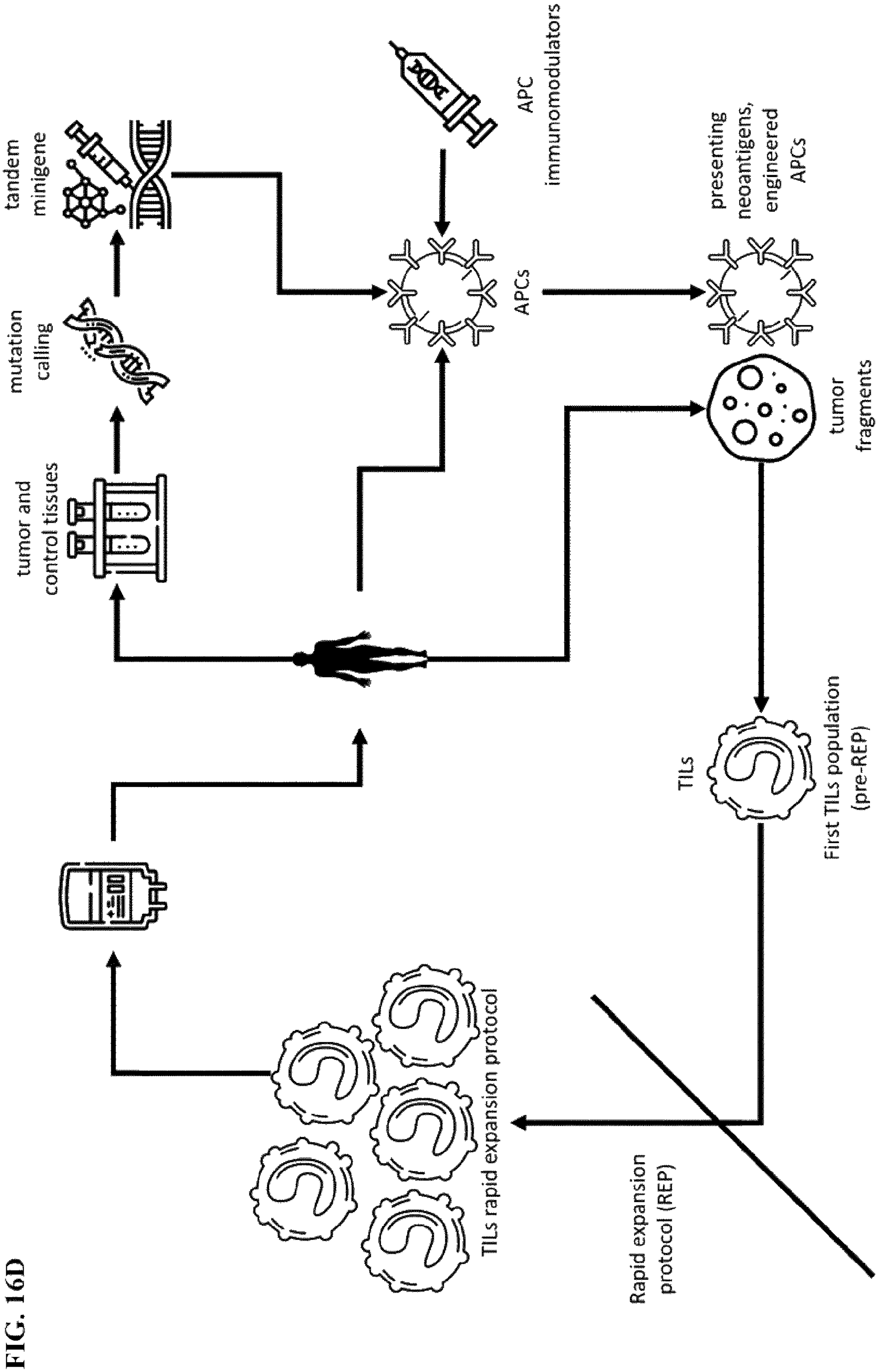
Figure 16E:
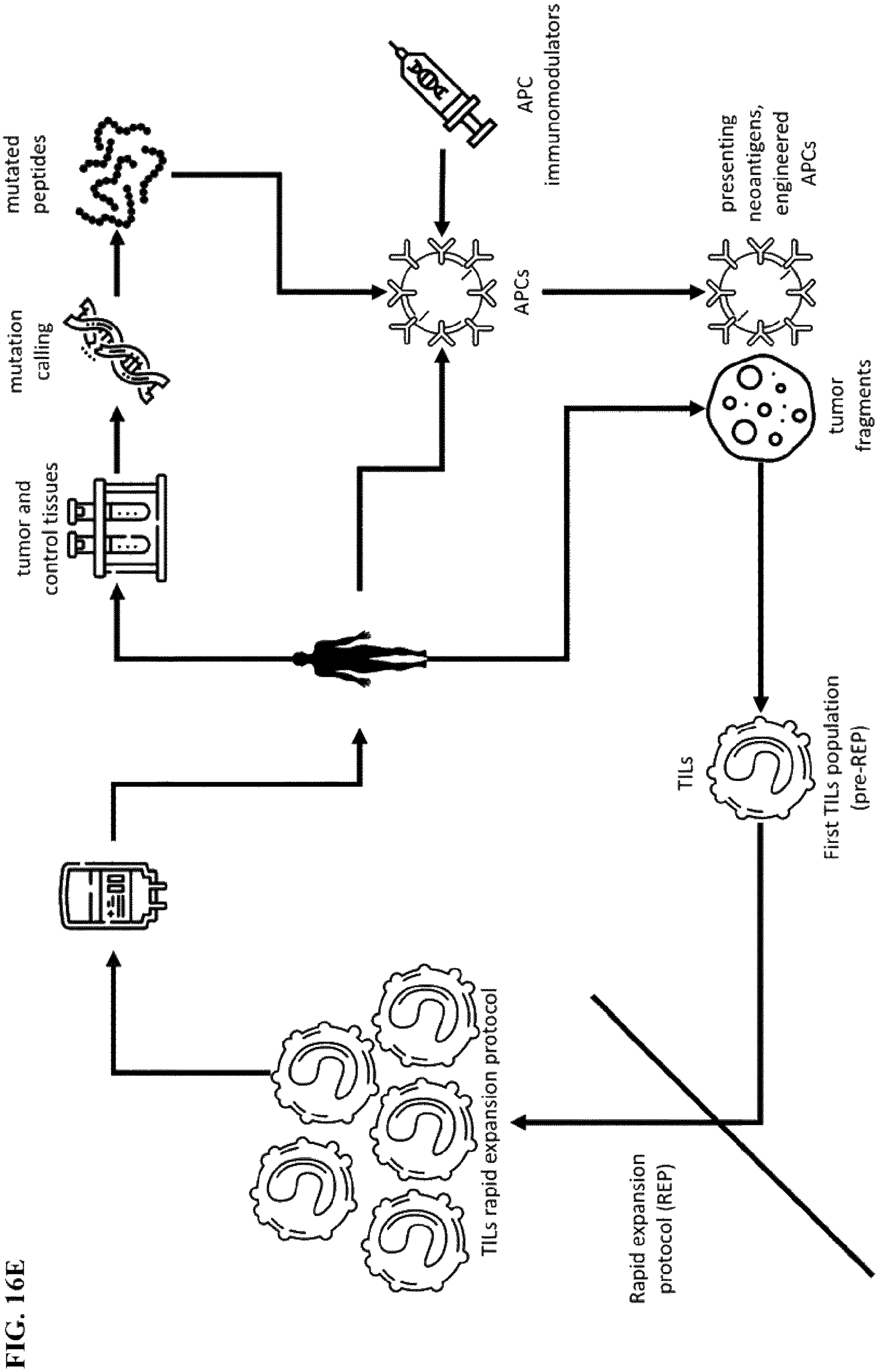
Figure 16F:
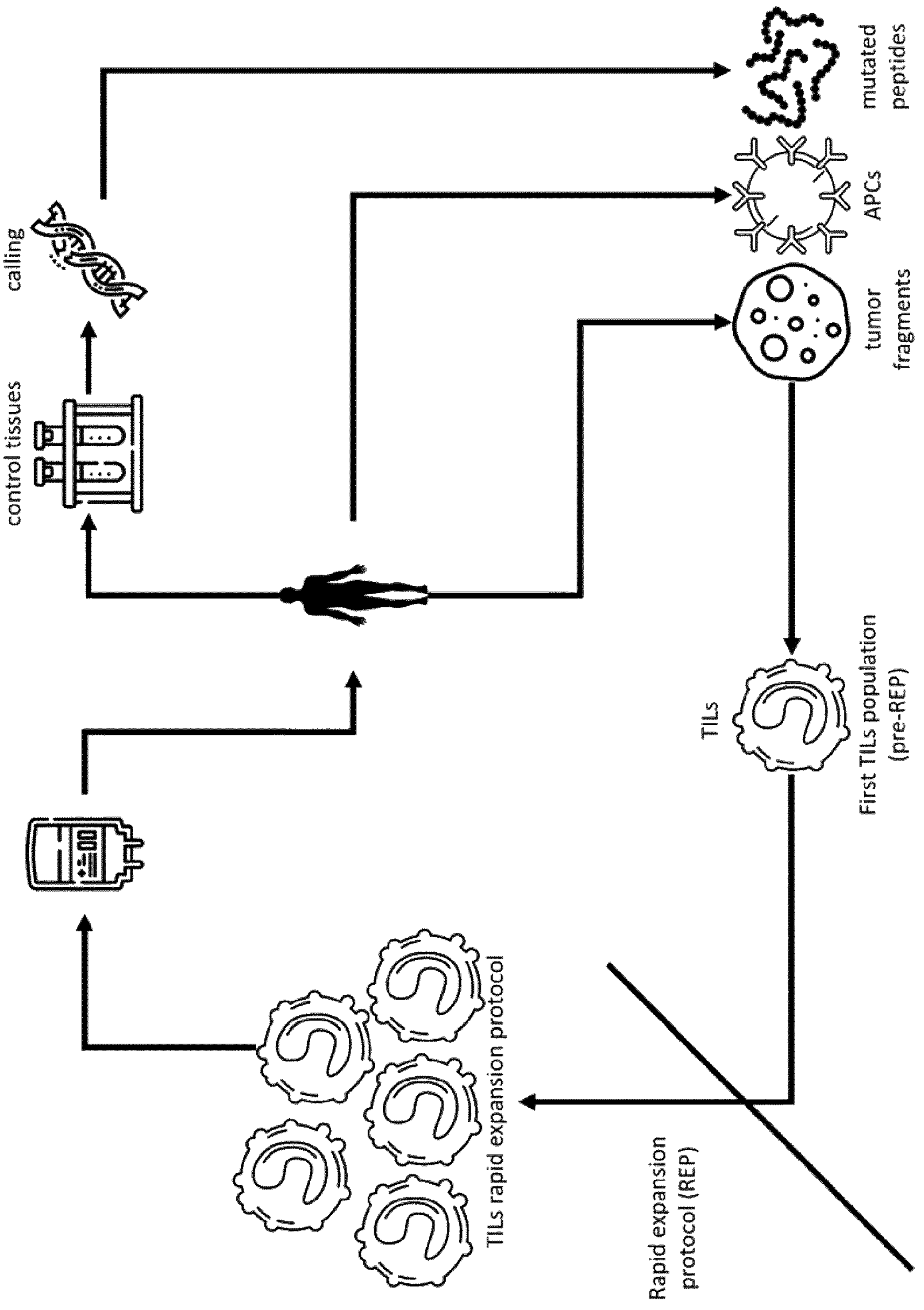
Figure 16G:
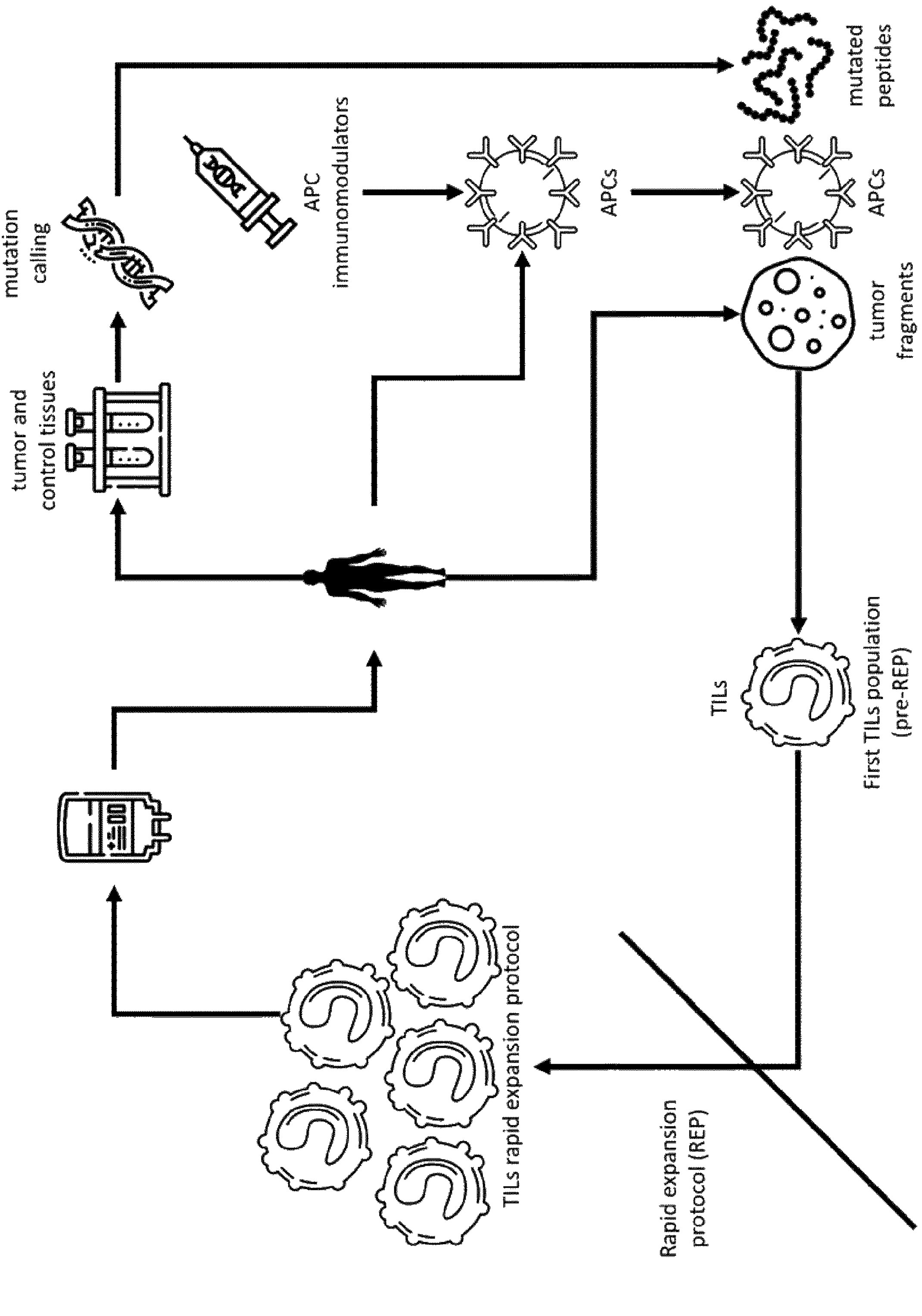

| Associated Figures | Peptides | SEQ ID NO | Peptides | SEQ ID NO | Peptides | SEQ ID NO | Peptides | SEQ ID NO |
|---|---|---|---|---|---|---|---|---|
| | WLVWLLLGPM | 16 | VQSAGPGRPL | 73 | SYGRVLFAV | 136 | IMLLTNWRF | 193 |
| | LVWLLLGPMV | 17 | GAVAGEGRAL | 74 | RVLFAVYHM | 137 | RGARAPAAW | 194 |
| | TVLLSATIFL | 18 | AAPTAVGPPL | 75 | GQALAEFAA | 138 | YSRRKFPAW | 195 |
| | VLLSATIFLV | 19 | TVASGENMTL | 76 | GQARQSRPV | 139 | TGLPHAPAL | 196 |
| | IAISCSYGQV | 20 | VASGENMTLL | 77 | RLLHPHHPL | 140 | YRVLQCANL | 197 |
| | CSCGQVLFAV | 21 | YKYEECKDVI | 78 | ALLDGGLPA | 141 | QSAGPGRPL | 198 |
| | CSYGRVLFAV | 22 | FLGHMVVSQM | 79 | LLDGGLPAG | 142 | AVAGEGRAL | 199 |
| | GQVLFAVYRM | 23 | FAVYRMKSAE | 80 | FISGRFPYS | 143 | VASGENMTL | 200 |
| | GQALAEFAAL | 24 | FRLLHPHHPL | 81 | HAPALDAPL | 144 | TWVYEGTVL | 201 |
| | LLVALLDGGL | 25 | ALDAPLFGI | 82 | APALDAPLF | 145 | ISCSCGQVL | 202 |
| | VALLDGGLPA | 26 | QLYRVLQCA | 83 | HVSDMSVVL | 146 | ISCSYGRVL | 203 |
| | FSLSTIHLRL | 27 | RVLQCANLL | 84 | VPCVCAVRY | 147 | FAVYRMKSA | 204 |
| | WPPPPATTPF | 28 | SEDSGNFSV | 85 | TPWPPPPAT | 148 | | |
| Fig. 2A | **SILEQMHRK** | 29 | GFLCVFSITK | 86 | QRWMKVNFEV | 149 | AEGETEGSV | 205 |
| CTE-0011 | T1AATERRVK | 30 | RWMKVNFEVF | 87 | SRFFSLVKQM | 150 | MEAGAGRDS | 206 |
| Wildtype: | FVAGAVGPHK | 31 | RFFSLVKQMI | 88 | EHEEVVLEEL | 151 | GELMVVTAS | 207 |
| SILEQMRRK | SISSAATPYR | 32 | VFSITKMESF | 89 | NRENREQYQL | 152 | KENPVVDVV | 208 |
| (SEQ ID | SSAATPYRIR | 33 | RYYICTAQNL | 90 | AAAALHMQR | 153 | CEGLNLLTA | 209 |
| NO: 4) | ATPYRIRFPR | 34 | OEYVTEHKGC | 91 | VAGAVGPHK | 154 | REKPYDCMA | 210 |
| | VQFSQLQELK | 35 | KEAVTFKDLA | 92 | SISSAATPY | 155 | LERGASAPA | 211 |
| | SQLQELKNLK | 36 | KEIEVLERGA | 93 | ISSAATPYR | 156 | EELEVHFKI | 212 |
| | GAGGVQSIAK | 37 | EELEYHFKIS | 94 | SIAKKSGQK | 157 | QESVPIGTA | 213 |
| | QSIAKKSGQK | 38 | QESVPIGTAV | 95 | DLQKFKFLK | 158 | AEHEEVVLE | 214 |
| | DSFVGADLQK | 39 | SEYWRGQREA | 96 | KTQLNPSSR | 159 | EQYQLVIQA | 215 |
| | FVGADLQKFK | 40 | AEHEEVVLEE | 97 | QLNPSSRQK | 160 | VQFSQLQEL | 216 |
| | FVGADLKNFK | 41 | REQYQLVIQA | 98 | GASAPATAK | 161 | RRASSSSSL | 217 |
| | MFYKILHSFK | 42 | FRHQAHWDRY | 99 | VLYVVRSLY | 162 | QKSDENQYL | 218 |
| | FLQEYVTLHK | 43 | RHQAHWDRYM | 100 | LSAIRTVAK | 163 | THRATPVFL | 219 |
| | TQLNPSSRQK | 44 | AHWDRYMGTL | 101 | RALFNRAQK | 164 | HRATPVFLV | 220 |
| | GVLYVVRSLY | 45 | QRTEPPGTFL | 102 | AASESPSLK | 165 | LRDGQILEF | 221 |
| | SLSAIRTVAK | 46 | THKENPVVDV | 103 | GNSSGALLK | 166 | SRQKLFREV | 222 |
| | GAASESPSLK | 47 | MRRASSSSSL | 104 | FLCVFSITK | 167 | ALFNRAQKL | 223 |
| | YTPQTSGLAK | 48 | VRLPTGGPLL | 105 | MFYKILHSF | 168 | QREALRQLL | 224 |
| | ITFQSWPNSK | 49 | THRATPVFLV | 106 | RWMKVNFEV | 169 | NREQYQLVI | 225 |
| Fig. 4 | **LPQARRILL** | 50 | KFYSSSSNTL | 107 | SVAGFLSSL | 170 | KQPPSVSHF | 226 |
| Fig. 14 | FSDFYGYIQY | 51 | KPMTNNARQM | 108 | SPTALRPRL | 171 | APSLDLSDL | 227 |
| Mel011 | RYIPTQALNF | 52 | ASRRAHYTSY | 109 | SIFEERTRY | 172 | SPVGPPFGL | 228 |
| Wildtype | SPAEPAPTSL | 53 | LLT1MSYDRY | 110 | ATSSQTSVY | 173 | MSNLFLGSY | 229 |
| LPQARRISL | LYPPPPSSSF | 54 | RIRSKKKKTL | 111 | FYSSSSNTL | 174 | RFLMSMRRL | 230 |
| (SEQ ID | SPSKSIINSM | 55 | RPFIHASSSM | 112 | LYLATHRRI | 175 | GYVQQRREF | 231 |
| NO: 5) | VPDGMGQWRY | 56 | FQHKMSQEGF | 113 | LTIMSYDRY | 176 | NVASAAPSL | 232 |
| | AMNKDKKSKF | 57 | SPSSMPLHPL | 114 | QTDKNVFRK | 177 | AMGGEVERF | 233 |
| | SPAWRIYVTL | 58 | KYVNIFENF | 115 | SPMFKNTSV | 178 | LQREMMSNL | 234 |
| | QQRREFSLKY | 59 | RYLDIKKIL | 116 | RAHFSPASL | 179 | LLATPRQLY | 235 |
| | TSDREDGLLK | 60 | RLSSLSAAY | 117 | RPKGPWSST | 180 | ESFKLSDSY | 236 |
| | SPSTQPGDSF | 61 | DAERFSDFY | 118 | HVKVNGRVY | 181 | YWITYEQTL | 237 |
| Fig. 5 | Pep1 | | NPDSVNASL | 119 | | | | |
| Fig. 8B | Pep2 | | LPYGLPTGL | 120 | | | | |
| CTE-0009 | Pep3 | | **IPINPRRCL** | 1 | | | | |
| Wildtype | Pep4 | | RSQRVRAAM | 121 | | | | |
| of pep3: | | | | | | | | |
| TPINPRRCL | | | | | | | | |
| (SEQ ID | | | | | | | | |
| NO: 6) | | | | | | | | |

TABLE 1-continued

Exemplary Peptides(s) used in Examples 1 and 2. Underlined peptides were used in the stimulation assays (i.e., for validation purposes).

Figure 10A:
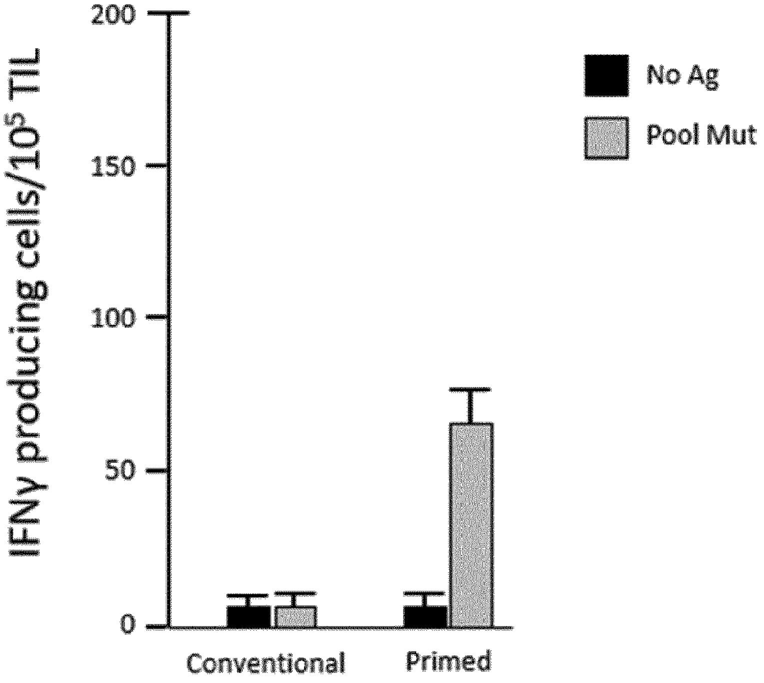
FIG. 10A-10B shows the effects of the invention and its variation on the TILs expansion during the pre-REP phase.

| Associated Figures | Peptides | SEQ ID NO | | SEQ ID NO | | SEQ ID NO | | SEQ ID NO |
|---|---|---|---|---|---|---|---|---|
| Fig. 10A Fig. 14 CTE-0006 Wildtype of pep6: GEYISSVAW (SEQ ID NO: 7) | Pep1<br>Pep2<br>Pep3 | | IVDDIGHGV<br>TIVDDIGHGV<br>**GEYISCVAW** | 122<br>123<br>124 | | | | |
| Fig. 12 Fig. 14 CTE-0007 Wildtype: SPIFKQKKDL (SEQ ID NO: 8) | GYVDVVKEL<br>PPAGGCRSPL<br>SPRRHDHEPA<br>APGITSVEI | 62<br>63<br>64<br>65 | YPPVPGNKL<br>**SPIFKQKKNL**<br>NLRRSKKRAL<br>APAAAATAA | 125<br>126<br>127<br>128 | APAAAATAAT<br>SPGPRNAPA<br>SPGPRNAPAA<br>EVRALLTQY | 182<br>183<br>184<br>185 | | |

Results and Discussion

Although the conventional tumor-infiltrating lymphocyte (TIL) expansion methods have served well patients with melanoma, optimization of TIL cultures may be required to maximize the recovery of neo-antigen specific T cell clones or enrich TIL culture in neo-antigen-specific T cells. To this end, this example sought to optimize the TIL expansion methodology to favor expansion of neo-antigen specific T cells. The above goal was achieved through multiple strategies.

The improvement of anti-tumor responses by immune-checkpoint blockade is a new approach for the treatment of advanced solid malignant tumors. In particular, treatment with anti-PD1 and anti-CTLA4 antibodies led to major clinical benefits. Additional studies have demonstrated that TILs expressing PD1 were enriched in neo-antigen-specific T cells. Based on this evidence, this example tested whether the addition of anti-PD1 and anti-CTLA4 antibodies, in combination, would lead to an enrichment of TIL culture in neo-antigen-specific T cells. Resuspended tumor cells from patients with ovarian cancer were enzymatically dissociated treated and treated with IL-2, anti-PD1 and anti-CTLA4 antibodies and then interrogated for their reactivity against pools of synthetic 9- and 10-mer peptides (50-100 different peptides in the pool) of all predicted class I neo-antigens. Data showed that addition of anti-PD1 and anti-CTLA4 antibodies did not lead to an enrichment of TIL cultures in neo-antigen-specific T cells (FIG. 1A).

Next, the effect of the addition of pools of predicted neo-antigens (pools of synthetic 9- and 10-mer peptides of all predicted class I neo-antigens) at the initiation of pre-REP using resuspended tumor cells from patients with ovarian cancer was tested. Compared to TILs cultured under conventional conditions (i.e., IL-2 alone), TILs cultured with pools of predicted neo-antigens were enriched in neo-antigen-specific T cells (FIG. 1B), including markedly higher frequencies of T cell clones recognizing either the same neo-antigen (FIG. 2A; the number of TILs in the upper right panel show detectable amount of TILs in the conventional (0.13) that increases to 3.32 in the primed TILs) or new neo-antigens that were undetectable under the conventional expansion protocol (FIG. 2B).

Figure 3:
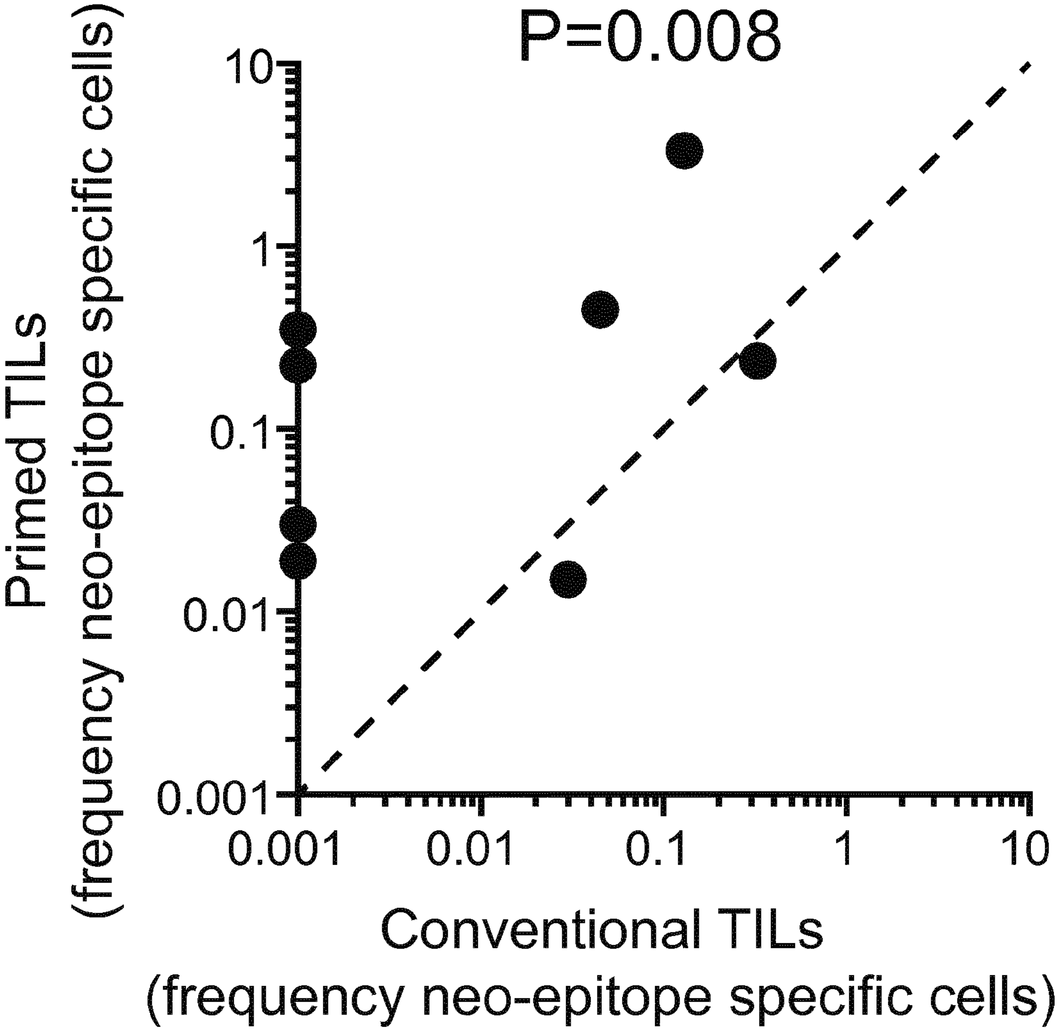
FIG. 3 shows a cumulative analysis of the frequencies of neo-antigen specific CD8+ T lymphocytes detected in conventional (IL-2 alone, x axis) and primed (IL-2+pools of predicted neo-antigens, y axis) TIL cultures from single cell suspension of ovarian tumor samples.

The enrichment in neo-antigen-specific T cells was demonstrated using specific peptide-WIC multimers. Taken together, TILs cultured with pools of predicted neo-antigens were significantly enriched in neo-antigen-specific T cells as compared to conventional TILs generated from the same patients with regards to both, the magnitude and the breadth of neo-antigen-specific T cells (e.g., CD8+ T cells; FIG. 3).

Next it was determined whether neo-antigen specific TILs can be expanded using tumor fragments rather than TILs generated from tumor enzymatic digestions. Tumor fragments from melanoma patients were cultured with IL-2 alone or IL-2 combined to pools of predicted neo-antigens and then interrogated for the reactivity against pools of predicted neo-antigens. Consistently with ovarian cancer samples, the reactivity against pools of predicted neo-antigens was higher in the TILs cultured with predicted neo-antigens (FIG. 4).

Taken together, TILs cultured with pools of predicted neo-antigens were significantly enriched in neo-antigen-specific T cells as compared to conventional TILs generated from the same patients. TILs cultured with pools of predicted neo-antigens were significantly enriched in neo-antigen specific T cells when the starting material was resuspended tumor cells or tumor fragments. TILs cultured with pools of predicted neo-antigens were significantly enriched in neo-antigen specific T cells when the starting material was from melanoma or ovarian cancer.

Both the magnitude and the breadth of neo-antigen-specific T cells increased in TILs cultured with pools of predicted neo-antigens. The enrichment in neo-antigen specific T cells of TILs cultured with pools of predicted neo-antigens was both quantitative and qualitative and was demonstrated using multiple tools including direct enumeration with peptide-MHC multimers, quantification of cytokine-producing cells by IFN-γ ELISpot and determination of multiple cytokines production by multiplexed bio-assay such as MSD.

Example 2

Figure 6B:
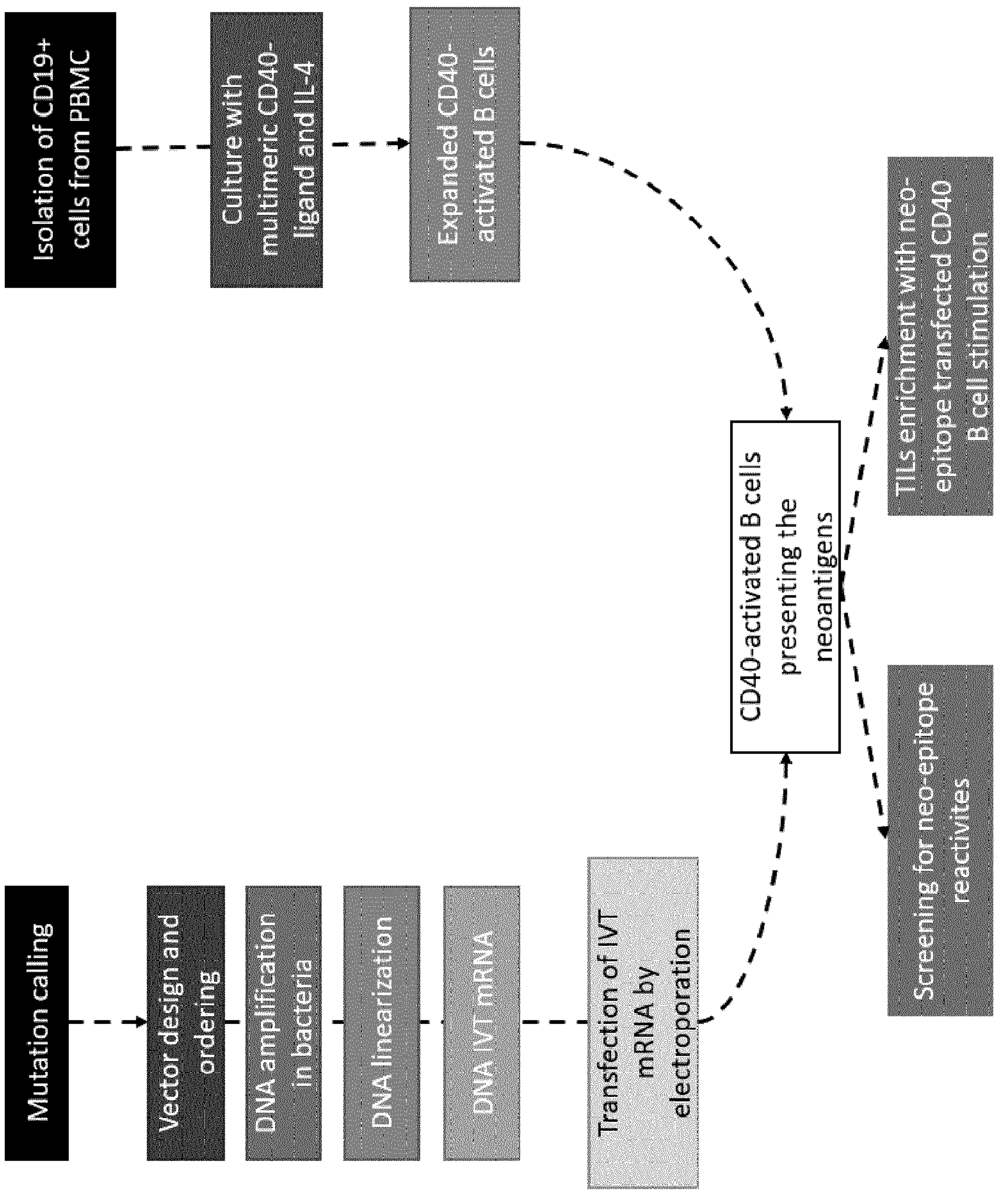

Example 1 relied on the use of 9- and 10-mer synthetic peptides derived from class I predicted neo-antigens, it was limited to the interrogation of CD8⁺ TIL responses. As such, Example 1 did not investigate potential CD4⁺ neo-antigen responses. Given the clinical relevance of class II neo-antigens and their frequency in certain tumors[15,16], this example investigates this avenue of TIL generation. To investigate the potential of CD4⁺ neo-antigen responses, a tandem-minigene (TMG) approach was utilized. A TMG is a DNA sequence composed of a variable number of mini-genes (up to 15), each encoding a 25-31-mer centered on an individual mutated amino acid (FIG. 6A) identified by whole-exome sequencing[8,17,18]. The TMG were cloned into appropriate expression vectors, which were used as a template to produce in vitro transcribed (IVT) mRNA that was then electroporated into antigen presenting cells (APCs) (FIG. 6B). In this example, the APCs were CD40-activated B cells derived from the patient. Importantly, using the patient's autologous professional APCs (e.g., dendritic cells DC or CD40-activated B cells) allows the presentation of neo-antigens in the context of the patient's own class I and II human leucocyte antigen (HLA) alleles and, thus, the direct interrogation of patient's CD4⁺ and CD8⁺ T cells (FIG. 6B). In order to further enrich TIL cultures in neo-antigen-specific T cells, autologous engineered-B cells (transiently transfected with mRNA encoding the different neoantigens) was tested at the stage of pre-REP (FIG. 6B).

Materials and Methods

Generation of IVT mRNA

Plasmid DNA constructions coding for 5 minigenes in tandem (TMG), with a T7 promoter upstream and untranslated regions (UTR) downstream (FIG. 7) (role in increasing mRNA stability) were ordered from Geneart (Thermofisher Scientific). The five minigenes consist in five 31-mers with the mutation at position 16 that were separated by non-immunogenic glycine/serine linkers (sequence detailed in FIG. 7)[11,19]. The resulting TMG was flanked by a signaling peptide (SP) and by MHC-class I trafficking signals (MITD)[20] (FIG. 7) to enable processing and presentation of each 31-mer by both class I & class II pathways. The DNA was linearized with the restriction enzyme Hind III, purified with phenol:chloroform and precipitated with ethanol. Following spectrophotometric quantification, 1 μg of linearized DNA was used as a template for the in vitro transcription and polyadenylation using the mMAchine mMessage T7 Ultra kit (Thermofisher Scientific). Resulting IVT mRNA was precipitated with LiCl according to the manufacturer's instructions. Polyadenylation and integrity was validated by gel electrophoresis in denaturing conditions. mRNA was finally quantified by Qbit fluorometer (Thermofisher Scientific). 4-1BBL and OX-40L had been previously cloned in the multiple cloning site of a pCMV6 vector (Addgene). IL-12alpha/P2A/IL-12beta nucleotide sequence was ordered at GeneArt and synthesized and cloned into the pMA-RQ plasmid downstream of a T7 promoter. See FIGS. 21-23 for sequences of the immunomodulators. After linearization, the entire coding region of each molecule had been retrotranscribed as described for TMG. In certain instances, the TMGs used in the experiment consist of 5 total minigenes, wherein one is coding for the cognate antigen while the other four may not be reactive. This was done to be able to use the same gene construct for different patient samples in the most cost-effective manner.

Generation of Autologous CD40-Activated B Cells

Autologous B cells were generated using recombinant multimeric CD40-ligand (mCD40-L) (Adipogen) and hrIL-4 (Miltenyi) (FIG. 6B). B cells were first isolated by positive selection of CD19⁺ cells with microbeads (Miltenyi) from autologous frozen PBMC or apheresis samples. CD19⁺ cells were then cultured for 10 to 14 days in B cell medium in order to expand activated CD40-B cells. B cell medium was comprised of RPMI complemented with 8% human serum, 1 μg/ml mCD40-L and 200 IU/ml hrIL-4.

Electroporation of IVT mRNA into APC

CD40-activated B cells were rested in RPMI complemented with 8% human serum and 200 IU/ml hrIL-4 overnight before co-culture assay with unsorted PBMCs or before TIL generation assay. CD40-activated B cells were harvested and gently washed twice with PBS before they were resuspended with buffer T from the Neon electroporation kit (Thermofisher Scientific) at 10-15e6 cells/ml in Eppendorf tubes. 1 μg IVT mRNA was added per electroporation of 100,000-150,000 cells. Cells were then collected with the Neon electroporation pipette (Thermofisher Scientific) in 10 μl (0.1-0.15e6 cells) or 100 μl (1-1.5e6 cells) tips and electroporation was performed by the Neon system (Thermofisher Scientific) with the following parameters: 1400V, 20 ms, 2 pulses. Immediately after, cells were added to pre-warmed B cell medium (described above) depleted from mCD40-L. Electroporated cells were incubated 4 to 17 hrs (overnight) at 37° C. and washed twice with RPMI prior to co-culture assays or TIL generation assays.

Peptide Pulsing of APC

For minimal antigen loading (i.e., 9-10-mer for class I antigens and 12-15mer for class II antigens), cells were harvested, washed twice with RPMI and resuspended at 1e6 cells/ml with RPMI 1% human serum complemented with the peptides or peptide pools. 9-10mers and 12-15mers were incubated with B cells at 1 μg/ml and 2 μg/ml, respectively (i.e., pre-loaded). Cells were incubated at 37° C. for 1-2 hrs and washed twice with RPMI before use in co-culture assays. For long peptide pre-loading (i.e., 31-mer), APCs were harvested, washed twice with RPMI and resuspended at 1e6 cells/ml with RPMI 8% human serum complemented with 200 IU/ml hrIL4 (Miltenyi) complemented with 1 to 20 μg/ml long peptides. APCs were then incubated at 37° C. for 16-20 hrs. (e.g., overnight) and washed twice with RPMI before use in co-culture assays.

Co-Culture Assays: IFNγ ELISPOT Assays and Intra-Cellular Cytokine Staining

ELISpot assays were performed using pre-coated 96-well ELISpot plates (Mabtech) and counted with Bioreader-6000-E (BioSys). When APCs were used in ELISpot to stimulate tumor-specific TILs or ELA clones (E cell clones recognizing MelanA peptide), 3e4 APC (autologous B cells or HLA-matched cell line) were co-cultured with 1-2e3 specific T cells. In screening conditions, 0.5-1.5e5 total TILs (enriched or not) were interrogated with 2.5e4 to 1e5 autologous B cells (4:1 to 1:1 ratio, respectively). TILs can also be interrogated by direct addition of the peptide (minimal or long peptides) in the ELISpot well (i.e., peptide spiking). After 16 to 20 hrs ELISpot plates were developed according to the manufacturer's instructions.

For ICS, T cells were plated with B cells at a ratio 1:1 or 2:1 in RPMI 8% human serum with brefeldin A (BD Biosciences). After 16 to 18 hrs, cells were harvested and stained with anti-CD3, anti-CD4, anti-IFNγ, anti-TNFα (BD biosciences), anti-CD137 (Miltenyi) and with a viability dye (Thermofisher Scientific). The stained cells were acquired on a four-laser Fortessa and FACSCanto (BD Biosciences) cell analyzers.

Pre-REP: TIL Generation

TILs were generated from tumor enzymatic digestion by plating total dissociated tumor in p24-well plates at a density of 1e6 cells per well in RMPI supplemented with 8% human serum and hrIL-2 (6000 IU/ml) without (conventional) or with (peptide primed) 1 μg/ml of class I predicted peptides (in pools of ≤50 peptides). When TILs were generated in the presence of transfected B cells at the initiation of pre-REP, the dissociated tumor is plated at a density of 5e5 cells per well together with 2.5-5e5 B cells (B cell primed). B cells are either non-transfected or transfected with mRNA encoding for neo-antigens. Subsequently, half of the medium was replaced every 2-3 days and TILs maintained at a density of 1-2e6/ml. T cell reactivity against predicted neo-antigen was tested by IFNγ ELISpot on pre-REP TILs. When described, culture media was supplemented with 10 μg/mL anti-PD1 mAb (eBiosciences) and 10 μg/mL anti-CTLA-4 mAb (Ipilimumab, Bristol-Myers) during the whole period of TIL culture (i.e., FIGS. 10, 12, 14 (only row 3 and 4) and 15 (CDCl20 and SGOLI).

electroporated APCs (i.e., TMG-APCs) as compared to the pulsed APCs (i.e., pre-loaded with peptide) during the pre-REP phase. As highlighted by FIG. 8A, depicting representative experiments, the level of antigen stimulation generated by TMG-APCs during the pre-REP phase was similar to that of APC pulsed with 1 μM MelanA peptide (routine class I peptide pulsing concentration) during the pre-REP phase. Indeed, IFNγ spot numbers and percentages of T cell clones with upregulated activation marker CD137 were in the same range for both prepared pools of APC.

However, as model cells used in FIG. 8A were ELA clones, the next step was to challenge the sensitivity of the TMG approach with a tumor sample—ovarian polyclonal COPG2$_{T371}$ peptide primed TILs (i.e., neo-antigen TILs for which pre-REP was performed with addition of peptide pools) from patient CTE-009 (FIG. 8B). Once again, similar levels of antigen stimulation was generated by both the

TABLE 2

Exemplary Tandem Minigenes (TMGs) used in Example 2. Underlined amino acids denote the mutated amino acid.

Figure 9A:
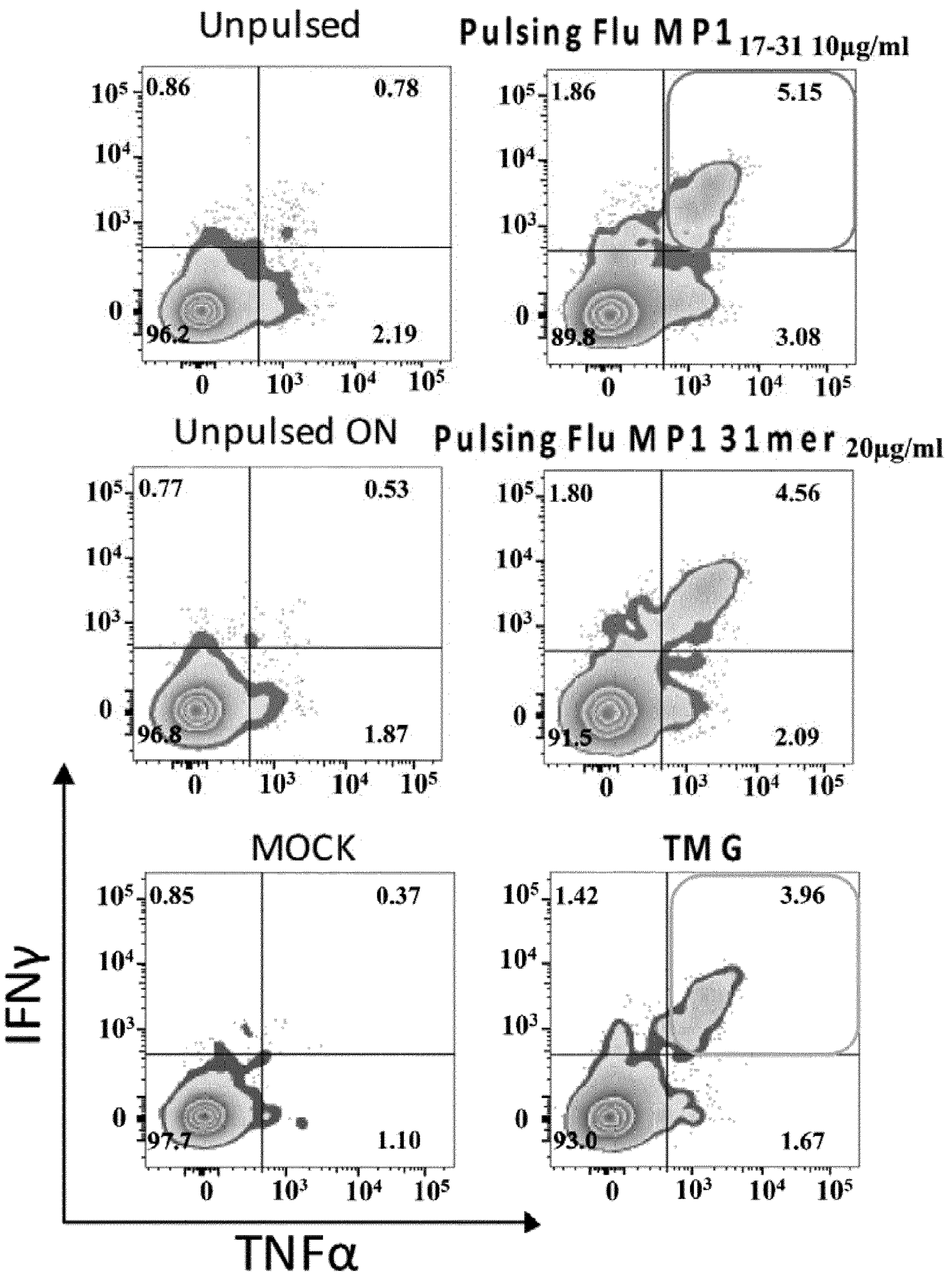
FIG. 9A-9B examines the processing and presentation of HLA class II antigens using viral and tumor-associated neo-antigens. The B cells were either pulsed (i.e., preloaded/incubated; Peptide) or transfected with tandem minigenes (TMG).
Figure 9B:
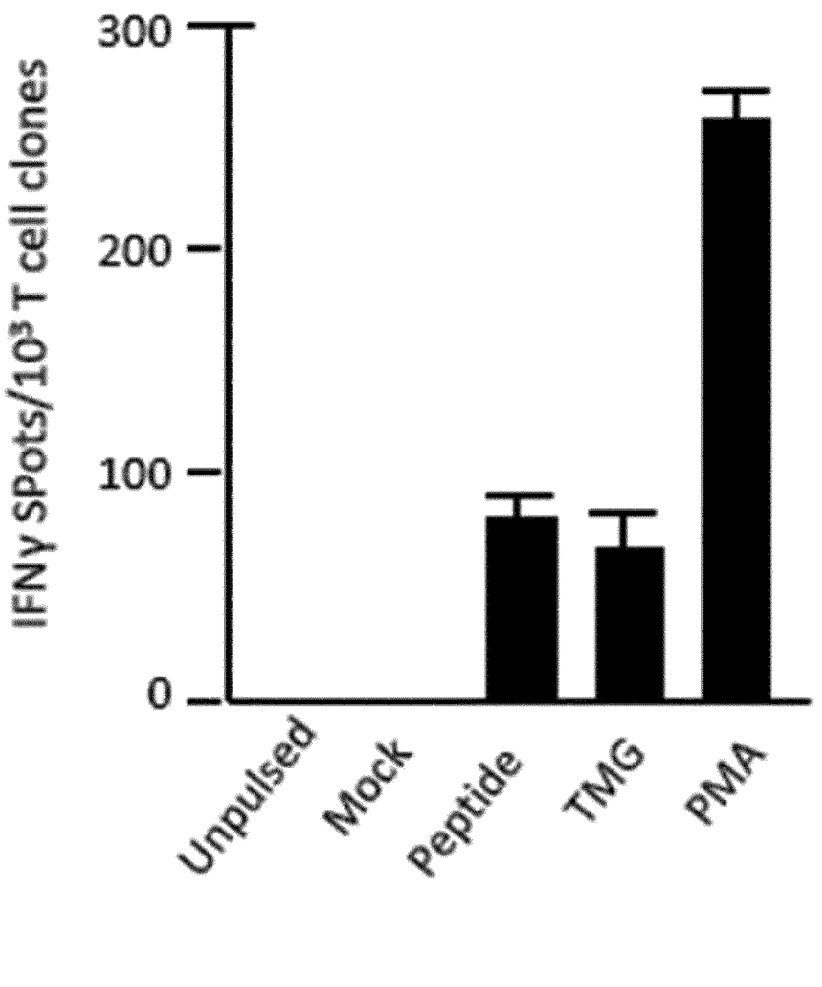
Figure 10B:
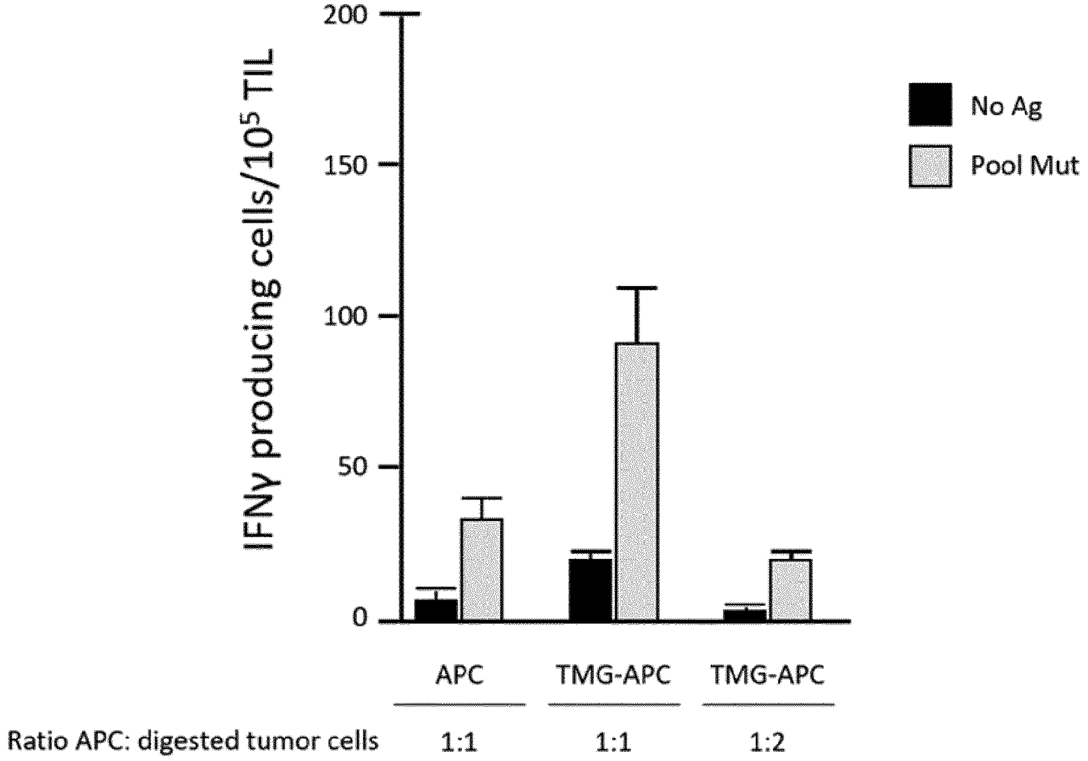

| TMG | TAA/Mutated Gene | (Mutated Minigene) Amino Acid Sequence | SEQ ID NO: | TMG Amino Acid Sequence | SEQ ID NO: | Corresponding Figure |
|---|---|---|---|---|---|---|
| 103 | MAGE-A3(111-126) | SEFQAALSRKVAELVHFLLLKYRAREPVTKA | 238 | SEFQAALSRKVAELVHFLLLKYRAREPVTKAGGSGGGGS | 258 | Fig. 8A, 9A, 9B |
| | FLU MP1(17-31) | TYVLSIVPSGPLKAEIAQRLEDVFAGKNTDL | 239 | GGTYVLSIVPSGPLKAEIAQRLEDVFAGKNTDLGGSGGG | | |
| | FLU MP1(58-66) | KTRPILSPLTKGILGFVFTLTVPSERGLQRR | 240 | GSGGKTRPILSPLTKGILGFVFTLTVPSERGLQRRGGSGG | | |
| | MelanA(25-36) | KGHGHSYTTAEEAAGIGILTVILGVLLLIGCW | 241 | GGSGGKGHGHSYTTAEEAAGIGILTVILGVLLLIGCWGGS | | |
| | FLU HA(307-319) | NKITYGACPKYVKQNTLKLATGMRNVPEKQT | 242 | GGGGSGGNKITYGACPKYVKQNTLKLATGMRNVPEKQT | | |
| 105 | PWWP2A | AAKQLTPEVRALLTQYET | 243 | AAKQLTPEVRALLTQYETGGSGGGGSGGGGFVLGLLFL | 259 | Fig. 8B, 12, 14 |
| | HLA-DRB1 | GGFVLGLLFLGAGLFLYFRNQKGHSGLQPTG | 244 | GAGLFLYFRNQKGHSGLQPTGGGSGGGGSGGTDLCFLN | | |
| | SGOL1 | TDLCFLNSPIFKQKKNLRRSKKRALEVSPAK | 245 | SPIFKQKKNLRRSKKRALEVSPAKGGSGGGGSGGEDADE | | |
| | HS6ST1 | EDADEPGRVPTEDYMIHIIEKW | 246 | PGRVPTEDYMIHIIEKWGGSGGGGSGGLEKSAVLQEARI | | |
| | COPG2 | LEKSAVLQEARIFNEIPINPRRCLHILTKIL | 247 | FNEIPINPRRCLHILTKIL | | |
| 106 | ABI2 | ERPVRYIRKPIDYTIVDDIGHGVKWLLRFKV | 248 | ERPVRYIRKPIDYTIVDDIGHGVKWLLRFKVGGSGGGGS | 260 | Fig. 10B, 14 |
| | CDC20 | ILQLLQMEQPGEYISCVAWIKEGNYLAVGTS | 249 | GGILQLLQMEQPGEYISCVAWIKEGNYLAVGTSGGSGGG | | |
| | USP47 | GPLPREGSGGSTSDYLSQSYSYSSILNKSET | 250 | GSGGGPLPREGSGGSTSDYLSQSYSYSSILNKSETGGSGG | | |
| | ABHD4 | RFRPDFKRKFADFFEMDTISEYIYHCNAQNP | 251 | GGSGGRFRPDFKRKFADFFEMDTISEYIYHCNAQNPGGS | | |
| | MST1 | WWVTVQPPARRMGWLSLLLLLTQCLGVPGQR | 252 | GGGGSGGWWVTVQPPARRMGWLSLLLLLTQCLGVPGQR | | |
| 108 | SYNP02 | PPRPVNAASPTNVQALSVYSVPAYTSPPSFF | 253 | AAKQLTPEVRALLTQYETGGSGGGGSGGGGFVLGLLFL | 259 | Fig. 14 |
| | NBEA | VGVGTSYGLPQARRILLATPRQLYKSSNMTQ | 254 | GAGLFLYFRNQKGHSGLQPTGGGSGGGGSGGTDLCFLN | | |
| | CES2 | HVKGANAGVQTFLGISFAKPPLGPLRFAPPE | 255 | SPIFKQKKNLRRSKKRALEVSPAKGGSGGGGSGGEDADE | | |
| | PHLPP2 | ATFSSNQSDNGLDSDYDQPVEGVITNGSKVE | 256 | PGRVPTEDYMIHIIEKWGGSGGGGSGGLEKSAVLQEARI | | |
| | NUP210 | SGQKKLHGLQAILVHVASGTTAITATATGYQ | 257 | FNEIPINPRRCLHILTKIL | | |

Results and Discussion

First, the processing and presentation of HLA class I and class II model antigens by transfected APCs was validated by comparing the level of antigen stimulation generated by CD40-activated B cells pulsed with 1 μM peptide and by the mRNA-transfected B cells. The latter cellular assays provided evidence of HLA class I antigen processing and presentation of the mutation-containing 31-mers introduced via TMG mRNA.

In order to demonstrate processing and presentation of HLA class II antigens, model antigens were used: viral and tumor-associated antigens. Similar to the method applied for HLA class I antigens, the level of antigen stimulation generated by pulsed-APCs and electroporated-APCs was compared. As illustrated by FIG. 9A and FIG. 9B, the processing and presentation of viral antigens (FIG. 9A) and of the tumor-associated antigen Mage-A3 (FIG. 9B) was achieved. Importantly, this demonstrates that the TMG methodology can be used to screen for HLA class I and class II neo-antigen reactivity. This allows one, not only to be independent from prediction algorithms, but also to have additional evidence of the processing of the putative neoantigens by autologous APCs.

Next, the addition of TMG-transfected autologous CD40-activated B cells at the initiation of pre-REP was tested, in comparison to the already established enrichment methodology based on peptide-priming (addition of peptide pools). To generate TILs from patient CTE-006, the addition of a pool of 3 peptides at 1 μg/ml each (FIG. 10A) was compared with the addition of CD40-activated B cells (APC, FIG. 10B) and with the addition of B cells electroporated with mRNA encoding the same three neo-antigens (TMG B cells). The enrichment with the peptide pool was revealed by ~70 IFNγ spots per 100,000 pre-REP TILs (FIG. 10A, grey bars). Of note, by adding TMG-electroporated B cells at day 0 (D0) to the pre-REP TILs at 1:1 ratio (TMG B cells 1:1 FIG. 10B), neo-antigen-specific T cells could further be enriched, as shown by ~100 IFNγ-secreting cells over 100,000 pre-REP TILs, two-fold higher than with incubation with neo-antigen pool alone.

It should be noted that the latter (i.e., TMG-B cell, 1:1 ratio) was the best condition, and there was no further enrichment with a second round of stimulation with TMG-B cells 1:1 at D5 of pre-REP (TMG B cells 1:1 R FIG. 10A). Interestingly, neo-antigen-specific TILs could also be enriched (although to a lower extent) by adding unstimulated (non-transfected) autologous CD40-activated B cells (FIG. 10B, APC). Without being bound by theory, it may be possible that activation of B cells is sufficient to improve the process. However, the process is better when neoantigen peptides or TMG are used and even better when costimulatory molecules (OX40L, 41BBL, IL12) are used.

Figure 11:
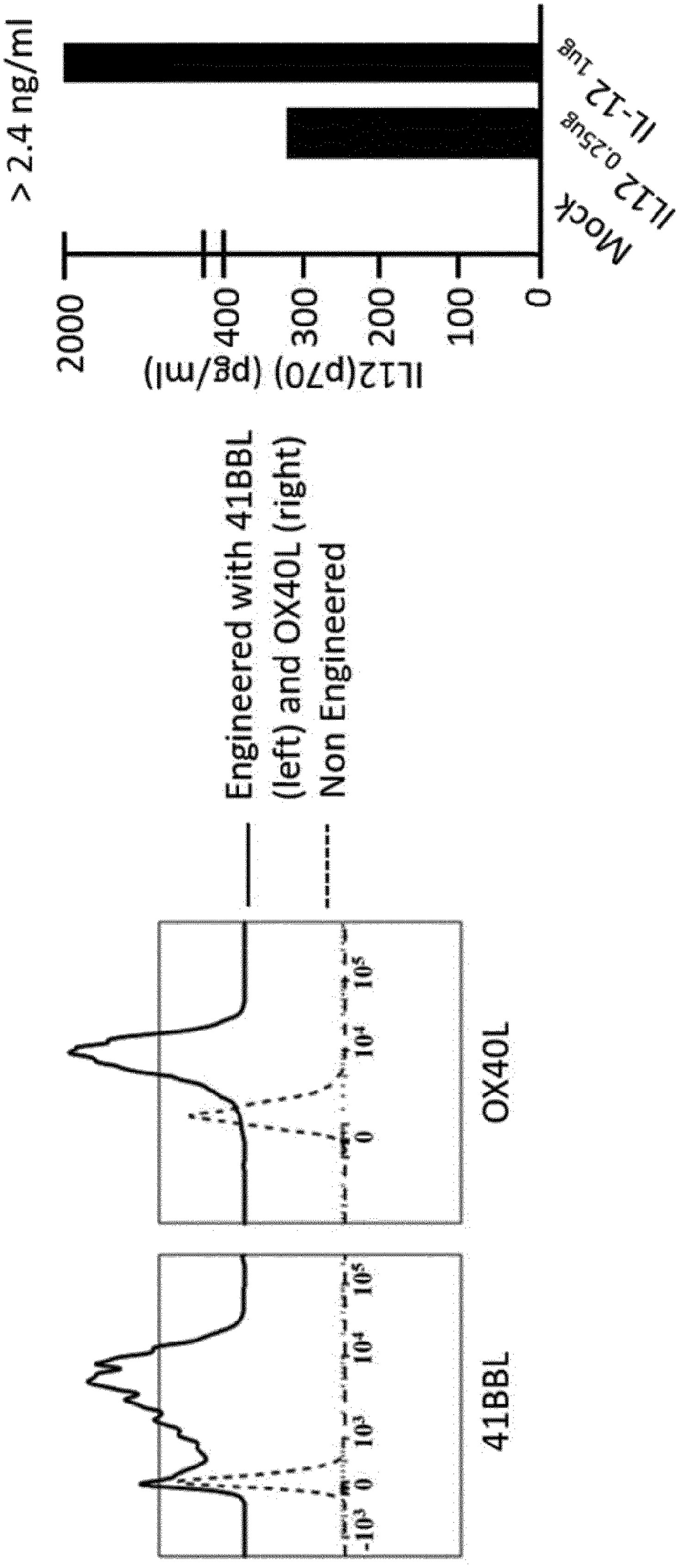
FIG. 11 shows analysis of engineered B cells and detection of 41BBL, OX40L, and IL12. On the left is flow cytometry analysis of 4-1BBL or OX40L expression after electroporation. CD40-activated B cells were electroporated with 1 μg of OX40L or 41BBL mRNA. On the right, analysis of IL-12 production by B cells by ELISA after electroporation with 0.25 μg or 1 μg of IL-12 mRNA. Assay was run 4-8 hours after transfection.

Engineered B cells successfully expressed OX40L and 41BBL and secreted a significant amount of IL-12 (FIG. 11).

The use of B cells co-electroporated with mRNA encoding OX40L, 41BBL and IL-12, in addition to TMG, lead to a further increase in the frequency of neo-antigen-specific T cells (FIG. 12: comparison between TMG-APC and Engineered TMG-APC). Also, a re-stimulation step at day 10 after initiation of the pre-REP with B cells co-electroporated with mRNA encoding OX40L, 41BBL and IL-12 together with TMG enables a further increase in the frequency of neo-antigen-specific T cells (FIGS. 12&14). Of note, neo-antigen-specific T cells could also be enriched by the addition of B cells together with the long peptide containing the neo-antigen at the initiation of TIL culture (FIG. 12).

Importantly, the addition of B cells during TIL generation appears to improve the pre-REP yield, as illustrated by the increase in fold expansion in the presence of B cells (engineered or not, FIG. 13).

Finally, the enrichment of TIL cultures in neo-antigen-specific T cells was achieved in different tumor types, with distinct sources of tumor cells. In particular, enrichment was consistently observed in patients with ovarian (CTE-006 and CTE-007) and colorectal cancer (CrCp5) as well as melanoma (Me10011) (FIG. 14). Furthermore, both dissociated tumor cells (ovarian cancer: FIG. 14, third and fourth rows; FIG. 15, CDC120 and SGOL1) as well as tumor fragments (melanoma: FIG. 14, first row; FIG. 15, NBEA; colorectal cancer: FIG. 14, second row; FIG. 15, PHLPP2) proved to be suitable for TIL enrichment (FIG. 14-15).

Taken together, the data indicate that TIL enrichment in neo-antigen-specific T cells is: 1) achieved with soluble peptides alone; 2) improved with the addition of B cells; 3) improved with the addition of B cells pulsed with peptides; 4) improved with the addition of B cells electroporated with TMG encoding neo-antigens; 5) improved with the addition of B cells engineered with vectors encoding OS40L, 41BBL, and/or IL-12; 6) improved with the addition or multiple rounds of simulation with B cells; 7) suitable to dissociated tumor cells or tumor fragments; 8) suitable to diverse tumor indications including, but not limited to, ovarian, colorectal, and melanoma; and 9) suitable with the addition of anti-PD1 and/or anti-CTLA-4 antibody treatment.

Example 3

Analysis of TILs Exhaustion

The methods as disclosed herein, lead to a lower occurrence of TIL exhaustion. In some embodiments, the presence of the neo-antigens (either direct or via APCs) lead to a lower frequency of TIL exhaustion.

In order to evaluate exhaustion in the TILs, the global gene expression profile can be used to compare TILs generated by conventional means (e.g., only IL-2 in the pre-REP phase) as compared to those generated by conventional means with the addition of neo-antigens (e.g., enriched). Analysis of gene expression profiles using consensus hierarchical clustering can show distinct clusters of enriched and conventional samples which correspond almost exactly to non-exhausted and exhausted TILs, indicating that the embodiments here described improve the quality of the TILs since the pre-REP phase. The analysis of gene expression profiles will show results very similar to microarray. It is expected that enriched and conventional TILs will show distinct clusters of gene expression and that these clusters will correspond to non-exhausted and exhausted TILs, respectively. Inspection of the list of differentially expressed genes may reveal genes with known roles in T cell biology including increased expression of the inhibitory receptors PD-1 and CTLA-4, which are upregulated with exhaustion.

In order to identify biological processes that were differentially active in primed vs. conventional TILs, gene set enrichment analysis using the Gene Ontology collection of gene sets can be performed.

In addition, expression of cell surface proteins can be analyzed for the presence of T cell exhaustion markers. T cell exhaustion is associated with i) expression of multiple inhibitory receptors like PD-1, CTLA-4, LAG-3, TIM-3, 2B4/CD244/SLAMF4, CD160, TIGIT, TCF1, CD39, BATF; ii) loss of IL-2 production, proliferative capacity, cytolytic activity; iii) impairment in the production of TNFalpha, IFNgamma, and cc (beta) chemokines; iv) degranulation and expression of high levels of granzyme B; v) poor responsiveness to IL-7, or IL-15; vi) altered expression of GATA-3, Bcl-6, and Helios; vii) alteration of T cell phenotype (e.g. T cells show a T follicular helper phenotype); and viii) cell death.

Thus, the comparative analysis of these exhaustion markers in pre-REP TILs generated by the methods as described herein and conventional methods can be performed, to determine which group is more or less exhausted.

The ability of primed vs. conventional TILs to further expand can be determined in vitro by labelling TILs with a cell proliferation tracker such as CFSE prior to stimulation.

The ability of primed vs. conventional TILs to further expand can be determined in vivo by adoptively transferring TILs into mouse models.

The fitness and stemness of primed vs. conventional TILs can be determined using different surface and intracellular markers such as TMRM or mitotracker.

Example 4

Dilution Effect of TILs

Conventional methods for TIL production of neo-antigen-specific TILs is limited in that such methods may not efficiently expand just neo-antigen-specific TILs and thus neo-antigen-specific TILs become diluted.

During the pre-REP phase of conventional methods, the TILs are expanded over tumor and other cells without enrichment. This causes a dramatic increase in number of TILs reactive against shared or immunodominant antigens with a limited effect on TILs reacting against neo-antigens.

Because of this issue, conventional methods require a means for selecting the TILs reacting against the neo-antigens (such as determining reactivity of TILs aliquots). Thus, the methods described herein do not need a means for selecting the TILs as there no dilution effect. For example, with conventional TIL expansion protocols, neo-antigen-reactive TILs tend to expand but less than other lymphocytes, and hence, get diluted. In the disclosed method, neo-antigen-specific lymphocytes are specifically stimulated, expand better, and reach higher frequencies at the end of pre-REP and ultimately REP.

To better understand this concept, it can be assumed that at day 0 a TIL culture has 18 T cells recognizing known antigen A, 9 T cells recognizing known antigen B, 2 T cells recognizing neoantigen X, and 3 T cells recognizing neoantigen Y. Given an exponential cell growth of 2×10^3, in conventional methods the TILs culture would have 5832 T cells for known antigen A, 729 T cells for known antigen B, 8 T cells for neoantigen X, and 27 T cells for neoantigen Y. Thus, the fractions reactive against neoantigens X and Y would have been diluted in the cell culture in favor of the known antigen A and B. However, the methods disclosed herein provide for enrichment of the neoantigens reactive T cells, and thus the fractions reactive against neoantigens X and Y are not diluted.

In order to demonstrate and determine the reduction and/or absence of this dilution effect (observed in conventional method), immune cells that stably express a fluorescence protein can be injected in an immunocompromised animal model (e.g., transplanting them in an immunocompromised mouse model). The animal model will have a traceable immune system via fluorescent protein. The animal model will then be subjected to tumor challenge by injection of tumor cells such as B16 melanoma. The fluorescent immune cells will reach the tumor site for infiltrating the tissue.

Tumor fragments with fluorescent tumor infiltrating lymphocytes can now be processed with the methods described herein and frequency of antigen-specific TILs as well as fold increase can be determined. For example, cells can be labelled with fluorescent dyes which allow one to determine proliferation history and to compare proliferation history of antigen-specific cells to that of other lymphocytes. The relative proliferation of neoantigen-specific will indicate whether of neoantigen-specific did proliferate less (i.e., got diluted) or not as compared to other lymphocytes. The results will show that in the conventional method the frequency of neoantigen-specific cells is reduced "diluted".

Neo-antigen-specific TILs identified at the end of pre-REP can be purified and analyzed for their composition in terms of T cell receptor (TCR) sequences. Specific TCRsequences from neo-antigen-specific TILs can then be detected and quantified in primary tumor to estimate their frequency. In other words, after adaptive transfer into patients, enriched TILs would better infiltrate tumors than TILs expanded under conventional methods. One way to demonstrate this is to determine TCR sequences of lymphocytes obtained from TILs expanded with conventional or enriched conditions and to determine the relative and absolute frequency of such TCR in tumor biopsies from patients. The relative fold expansion of TCRsequences from neo-antigen-specific TILs using conventional vs. primed methods can be compared after adoptive transfer in patients.

REFERENCES

1. Rosenberg, S. A. et al. Durable Complete Responses in Heavily Pretreated Patients with Metastasic Melanoma Using T Cell Transfer Immunotherapy. *Clin. Cancer Res.* 17, 4550-4557 (2011).
2. Hacohen, N., Fritsch, E. F., Carter, T. A., Lander, E. S. & Wu, C. J. Getting Personal with Neoantigen-Based Therapeutic Cancer Vaccines. *Cancer Immunol. Res.* 1, 11-15 (2013).
3. Schumacher, T. N. & Schreiber, R. D. Neoantigens in cancer immunotherapy. *Science* (80-.). 348, 69-74 (2015).
4. Schumacher, T. N. & Hacohen, N. Neoantigens encoded in the cancer genome. *Current Opinion in Immunology* 41, 98-103 (2016).
5. Rizvi, N. A. et al. Mutational landscape determines sensitivity to PD-1 blockade in non-small cell lung cancer. *Science* (80-.). 348, 124-128 (2015).
6. Yarchoan, M., Johnson, B. A., Lutz, E. R., Laheru, D. A. & Jaffee, E. M. Targeting neoantigens to augment antitumour immunity. *Nat. Rev. Cancer* (2017). doi:10.1038/nrc.2016.154
7. McGranahan, N. et al. Clonal neoantigens elicit T cell immunoreactivity and sensitivity to immune checkpoint blockade. *Science* (80-.). 351(6280), 1463-9 (2016).
8. Prickett, T. D. et al. Durable Complete Response from Metastatic Melanoma after Transfer of Autologous T Cells Recognizing 10 Mutated Tumor Antigens. *Cancer Immunol. Res.* 4, 669-678 (2016).
9. Zhou, J., Dudley, M. E., Rosenberg, S. a & Robbins, P. F. Persistence of multiple tumor-specific T cell clones is associated with complete tumor regression in a melanoma patient receiving adoptive cell transfer therapy. *J. Immunother.* 28, 53-62 (2005).
10. Tran, E. et al. Cancer Immunotherapy Based on Mutation-Specific CD4+ T Cells in a Patient with Epithelial Cancer. *Science* (80-.). 9, 641-645 (2014).
11. Sahin, U. et al. Personalized RNA mutanome vaccines mobilize poly-specific therapeutic immunity against cancer. *Nature* (2017). doi:10.1038/nature23003
12. Ott, P. A. et al. An immunogenic personal neoantigen vaccine for patients with melanoma. *Nature* (2017). doi:10.1038/nature22991
13. Rosenberg, S. A. & Restifo, N. P. Adoptive cell transfer as personalized immunotherapy for human cancer. *Science* (80-.). 348, 62-68 (2015).

14. Bobisse, S. et al. Sensitive and frequent identification of high avidity neo-epitope specific CD8+ T cells in immunotherapy-naive ovarian cancer. *Nat. Commun.* 9, 1092 (2018).
15. Linnemann, C. et al. High-throughput epitope discovery reveals frequent recognition of neo-antigens by CD4+ T cells in human melanoma. *Nat Med* 21, 81-85 (2015).
16. Diekmann, J. et al. Mutant MHC class II epitopes drive therapeutic immune responses to cancer. Nature 250, 692-696 (2015).
17. Stevanović, S. et al. Landscape of immunogenic tumor antigens in successful immunotherapy of virally induced epithelial cancer. *Science* (80-.). 356, 200 LP-205 (2017).
18. Parkhurst, M., Robbins, P. & Rosenberg, S. Isolation of T cell receptors specifically reactive with mutated tumor associated antigens. *Clin. Cancer Res.* 2, (2016).
19. Holtkamp, S. et al. Modification of antigen encoding RNA increases stability, translational efficacy and T cell stimulatory capacity of dendritic cells Modification of antigen encoding RNA increases stability, translational efficacy and T cell stimulatory capacity of dendr. *Blood* 108, 4009-4018 (2006).
20. Kreiter, S. et al. Increased Antigen Presentation Efficiency by Coupling Antigens to MHC Class I Trafficking Signals. *J. Immunol.* 180, 309-318 (2007).
21. Tran, E. et al. Immunogenicity of somatic mutations in human gastrointestinal cancers.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

---

What is claimed is:

1. A method for preferentially expanding tumor antigen-specific tumor infiltrating lymphocytes (TILs) ex vivo comprising:

expanding TILs in a sample obtained from a subject or TILs isolated from such sample, wherein the sample is an untreated tumor fragment, an enzymatically treated tumor fragment, or dissociated/suspended tumor cells, wherein expanding comprises at least two phases of expansion, wherein during at least the first phase of expansion, the TILs are cultured in the presence of an antigen-presenting cell (APC) presenting one or more tumor antigen(s), wherein the APC is an autologous B cell engineered to express OX40L, 4-1BBL and IL-12, and wherein tumor antigen-specific TILs are preferentially expanded over other lymphocytes present during the expansion resulting in an enrichment of tumor antigen-specific TILs.

2. The method of claim 1, wherein the second phase of expansion is conducted in the presence of at least one of CD3 complex agonist, mitogens, or feeder cells.

3. The method of claim 2, wherein the CD3 complex agonist is an anti-CD3 complex agonist antibody.

4. The method of claim 1, wherein the first phase of expansion is repeated at least twice and the lymphocytes from each first phase of expansion are pooled together prior to the second phase of expansion.

5. The method of claim 1, wherein one or more peptides are presented on the surface of the APC.

6. The method of claim 5, wherein the one or more peptides are present in a pool of about 2 to about 100 different peptides, about 20 to about 50 different peptides, about 2 to about 10 different peptides, or about 2 to about 5 different peptides.

7. The method of claim 1, wherein the APC has been preincubated with one or more peptides in a soluble form.

8. The method of claim 7, wherein the one or more peptides are present in a pool of about 2 to about 100 different peptides, about 20 to about 50 different peptides, about 2 to about 10 different peptides, or about 2 to about 5 different peptides.

9. The method of claim 1, wherein the APC has been engineered to express one or more peptides on its surface.

10. The method of claim 1, wherein the first phase of expansion comprises expanding the TILs in the presence of at least one expansion-promoting agent, wherein the expansion-promoting agent is an immunomodulatory agent, a cytokine, a soluble molecule, and antibody favoring the expansion of lymphocytes, or any combination thereof.

11. The method of claim 10, wherein the cytokine is at least one of interleukin-2 (IL-2), interleukin-4 (IL-4), interleukin-7 (IL-7), interleukin-15 (IL-15), interleukin-17 (IL-17), or interleukin-21 (IL-21).

12. The method of claim 10, wherein at least one of the expansion-promoting agents is IL-2.

13. The method of claim 1, wherein:

the first phase of expansion comprises preferentially expanding TILs in a tumor sample obtained from the subject or TILs isolated from the tumor sample in the presence of (i) interleukin-2 (IL-2) and (ii) autologous B cells engineered to express OX40L, 4-1BBL and IL-12, and the second phase of expansion comprises expanding the TILs expanded in the first phase of expansion in the presence of (i) anti-CD3 complex agonist antibody, (ii) autologous or allogeneic feeder cells, and (iii) IL-2.

14. The method of claim 13, wherein the first phase of expansion is performed at least twice and the TILs expanded in each first phase of expansion are pooled together prior to the second phase of expansion.

15. The method of claim 13, wherein the first phase of expansion further comprises up to 100 different peptides.

* * * * *

SEQUENCE LISTING

<160> NUMBER OF SEQ ID NOS: 275

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 1

Ile Pro Ile Asn Pro Arg Arg Cys Leu
1 5

<210> SEQ ID NO 2
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 2

Arg Lys Val Ala Glu Leu Val His Phe Leu Leu Leu Lys Tyr Arg Ala
1 5 10 15

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 3

Lys Gln Trp Leu Val Trp Leu Leu Leu
1 5

<210> SEQ ID NO 4
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

```
      Synthetic peptide"

<400> SEQUENCE: 4

Ser Ile Leu Glu Gln Met Arg Arg Lys
1               5


<210> SEQ ID NO 5
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Leu Pro Gln Ala Arg Arg Ile Ser Leu
1               5


<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Thr Pro Ile Asn Pro Arg Arg Cys Leu
1               5


<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Glu Tyr Ile Ser Ser Val Ala Trp
1               5


<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ser Pro Ile Phe Lys Gln Lys Lys Asp Leu
1               5                   10


<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9
```

Lys Gln Trp Leu Val Trp Leu Phe Leu
1 5

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Leu Gln Leu Tyr Arg Val Leu Gln Cys Ala
1 5 10

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 11

Val Val Leu Pro Pro Glu Thr Arg Pro Ile
1 5 10

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 12

Tyr Ile Met Leu Leu Thr Asn Trp Arg Phe
1 5 10

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 13

Leu Thr Asn Trp Arg Phe Thr Arg Gly Val
1 5 10

<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 14

Trp Leu Val Trp Leu Phe Leu Gly His Met
1 5 10

```
<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Leu Val Trp Leu Phe Leu Gly His Met Val
1               5                   10


<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Trp Leu Val Trp Leu Leu Leu Gly Pro Met
1               5                   10


<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Leu Val Trp Leu Leu Leu Gly Pro Met Val
1               5                   10


<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Thr Val Leu Leu Ser Ala Thr Ile Phe Leu
1               5                   10


<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Val Leu Leu Ser Ala Thr Ile Phe Leu Val
1               5                   10


<210> SEQ ID NO 20
<211> LENGTH: 10
<212> TYPE: PRT
<213> ORGANISM: Artificial Sequence
```

<220> FEATURE:
<221> NAME/KEY: source
<223> OTHER INFORMATION: /note="Description of Artificial Sequence:
Synthetic peptide"

<400> SEQUENCE: 20

Ile Ala Ile Ser Cys Ser Tyr Gly Gln Val
1 5 10

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 21

Cys Ser Cys Gly Gln Val Leu Phe Ala Val
1 5 10

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 22

Cys Ser Tyr Gly Arg Val Leu Phe Ala Val
1 5 10

<210> SEQ ID NO 23
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 23

Gly Gln Val Leu Phe Ala Val Tyr Arg Met
1 5 10

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 24

Gly Gln Ala Leu Ala Glu Phe Ala Ala Leu
1 5 10

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 25

Leu Leu Val Ala Leu Leu Asp Gly Gly Leu
1 5 10

<210> SEQ ID NO 26
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 26

Val Ala Leu Leu Asp Gly Gly Leu Pro Ala
1 5 10

<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 27

Phe Ser Leu Ser Thr Ile His Leu Arg Leu
1 5 10

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

Trp Pro Pro Pro Pro Ala Thr Thr Pro Phe
1 5 10

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

Ser Ile Leu Glu Gln Met His Arg Lys
1 5

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

Thr Ile Ala Ala Thr Glu Arg Arg Val Lys 1 5 10

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

Phe Val Ala Gly Ala Val Gly Pro His Lys
1 5 10

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

Ser Ile Ser Ser Ala Ala Thr Pro Tyr Arg
1 5 10

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

Ser Ser Ala Ala Thr Pro Tyr Arg Ile Arg
1 5 10

<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 34

Ala Thr Pro Tyr Arg Ile Arg Phe Pro Arg
1 5 10

<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 35

Val Gln Phe Ser Gln Leu Gln Glu Leu Lys
1 5 10

<210> SEQ ID NO 36

<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

Ser Gln Leu Gln Glu Leu Lys Asn Leu Lys
1 5 10

<210> SEQ ID NO 37
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

Gly Ala Gly Gly Val Gln Ser Ile Ala Lys
1 5 10

<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Gln Ser Ile Ala Lys Lys Ser Gly Gln Lys
1 5 10

<210> SEQ ID NO 39
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

Asp Ser Phe Val Gly Ala Asp Leu Gln Lys
1 5 10

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 40

Phe Val Gly Ala Asp Leu Gln Lys Phe Lys
1 5 10

<210> SEQ ID NO 41
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 41

Phe Val Gly Ala Asp Leu Lys Asn Phe Lys
1 5 10

<210> SEQ ID NO 42
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 42

Met Phe Tyr Lys Ile Leu His Ser Phe Lys
1 5 10

<210> SEQ ID NO 43
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 43

Phe Leu Gln Glu Tyr Val Thr Leu His Lys
1 5 10

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 44

Thr Gln Leu Asn Pro Ser Ser Arg Gln Lys
1 5 10

<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 45

Gly Val Leu Tyr Val Val Arg Ser Leu Tyr
1 5 10

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 46

Ser Leu Ser Ala Ile Arg Thr Val Ala Lys
1 5 10

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 47

Gly Ala Ala Ser Glu Ser Pro Ser Leu Lys
1 5 10

<210> SEQ ID NO 48
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 48

Tyr Thr Pro Gln Thr Ser Gly Leu Ala Lys
1 5 10

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 49

Ile Thr Phe Gln Ser Trp Pro Asn Ser Lys
1 5 10

<210> SEQ ID NO 50
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

Leu Pro Gln Ala Arg Arg Ile Leu Leu
1 5

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 51

Phe Ser Asp Phe Tyr Gly Tyr Ile Gln Tyr
1 5 10

<210> SEQ ID NO 52
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 52

Arg Tyr Ile Pro Thr Gln Ala Leu Asn Phe
1 5 10

<210> SEQ ID NO 53
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 53

Ser Pro Ala Glu Pro Ala Pro Thr Ser Leu
1 5 10

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 54

Leu Tyr Pro Pro Pro Pro Ser Ser Ser Phe
1 5 10

<210> SEQ ID NO 55
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 55

Ser Pro Ser Lys Ser Ile Ile Asn Ser Met
1 5 10

<210> SEQ ID NO 56
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 56

Val Pro Asp Gly Met Gly Gln Trp Arg Tyr
1 5 10

<210> SEQ ID NO 57
<211> LENGTH: 10

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 57

Ala Met Asn Lys Asp Lys Lys Ser Lys Phe
1 5 10

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 58

Ser Pro Ala Trp Arg Ile Tyr Val Thr Leu
1 5 10

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 59

Gln Gln Arg Arg Glu Phe Ser Leu Lys Tyr
1 5 10

<210> SEQ ID NO 60
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 60

Thr Ser Asp Arg Glu Asp Gly Leu Leu Lys
1 5 10

<210> SEQ ID NO 61
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 61

Ser Pro Ser Thr Gln Pro Gly Asp Ser Phe
1 5 10

<210> SEQ ID NO 62
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Tyr Val Asp Val Val Lys Glu Leu
1               5

<210> SEQ ID NO 63
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Pro Pro Ala Gly Gly Cys Arg Ser Pro Leu
1               5                   10

<210> SEQ ID NO 64
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Ser Pro Arg Arg His Asp His Glu Pro Ala
1               5                   10

<210> SEQ ID NO 65
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ala Pro Gly Ile Thr Ser Val Glu Ile
1               5

<210> SEQ ID NO 66
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Phe Pro Phe Ile Ala Ile Ser Cys Ser Tyr
1               5                   10

<210> SEQ ID NO 67
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

```
Phe Pro Phe Ile Gly Ile Ser Cys Ser Cys
1               5                   10


<210> SEQ ID NO 68
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Leu Pro Val Thr Asp Thr Ser Ser Val Ser
1               5                   10


<210> SEQ ID NO 69
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Phe Pro Tyr Ser Arg Arg Lys Phe Pro Ala
1               5                   10


<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Leu Thr Gly Leu Pro His Ala Pro Ala Leu
1               5                   10


<210> SEQ ID NO 71
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Thr His Val Ser Asp Met Ser Val Val Leu
1               5                   10


<210> SEQ ID NO 72
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Tyr Arg Val Leu Gln Cys Ala Asn Leu Leu
1               5                   10
```

<210> SEQ ID NO 73
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 73

Val Gln Ser Ala Gly Pro Gly Arg Pro Leu
1 5 10

<210> SEQ ID NO 74
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 74

Gly Ala Val Ala Gly Glu Gly Arg Ala Leu
1 5 10

<210> SEQ ID NO 75
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 75

Ala Ala Pro Thr Ala Val Gly Pro Pro Leu
1 5 10

<210> SEQ ID NO 76
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 76

Thr Val Ala Ser Gly Glu Asn Met Thr Leu
1 5 10

<210> SEQ ID NO 77
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 77

Val Ala Ser Gly Glu Asn Met Thr Leu Leu
1 5 10

<210> SEQ ID NO 78
<211> LENGTH: 10
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 78

Tyr Lys Tyr Glu Glu Cys Lys Asp Val Ile
1 5 10

<210> SEQ ID NO 79
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 79

Phe Leu Gly His Met Val Val Ser Gln Met
1 5 10

<210> SEQ ID NO 80
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 80

Phe Ala Val Tyr Arg Met Lys Ser Ala Glu
1 5 10

<210> SEQ ID NO 81
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

Phe Arg Leu Leu His Pro His His Pro Leu
1 5 10

<210> SEQ ID NO 82
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

Ala Leu Asp Ala Pro Leu Phe Gly Ile
1 5

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 83

Gln Leu Tyr Arg Val Leu Gln Cys Ala
1 5

<210> SEQ ID NO 84
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 84

Arg Val Leu Gln Cys Ala Asn Leu Leu
1 5

<210> SEQ ID NO 85
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 85

Ser Glu Asp Ser Gly Asn Phe Ser Val
1 5

<210> SEQ ID NO 86
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 86

Gly Phe Leu Cys Val Phe Ser Ile Thr Lys
1 5 10

<210> SEQ ID NO 87
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 87

Arg Trp Met Lys Val Asn Phe Glu Val Phe
1 5 10

<210> SEQ ID NO 88
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 88

Arg Phe Phe Ser Leu Val Lys Gln Met Ile
1 5 10

<210> SEQ ID NO 89
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 89

Val Phe Ser Ile Thr Lys Met Glu Ser Phe
1 5 10

<210> SEQ ID NO 90
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 90

Arg Tyr Tyr Ile Cys Thr Ala Gln Asn Leu
1 5 10

<210> SEQ ID NO 91
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 91

Gln Glu Tyr Val Thr Leu His Lys Gly Cys
1 5 10

<210> SEQ ID NO 92
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 92

Lys Glu Ala Val Thr Phe Lys Asp Leu Ala
1 5 10

<210> SEQ ID NO 93
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 93

Lys Glu Ile Glu Val Leu Glu Arg Gly Ala
1 5 10

```
<210> SEQ ID NO 94
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Glu Glu Leu Glu Val His Phe Lys Ile Ser
1               5                   10


<210> SEQ ID NO 95
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gln Glu Ser Val Pro Ile Gly Thr Ala Val
1               5                   10


<210> SEQ ID NO 96
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Ser Glu Tyr Trp Arg Gly Gln Arg Glu Ala
1               5                   10


<210> SEQ ID NO 97
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Ala Glu His Glu Glu Val Val Leu Glu Glu
1               5                   10


<210> SEQ ID NO 98
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Arg Glu Gln Tyr Gln Leu Val Ile Gln Ala
1               5                   10


<210> SEQ ID NO 99
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 99

Phe Arg His Gln Ala His Trp Asp Arg Tyr
1               5                   10


<210> SEQ ID NO 100
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Arg His Gln Ala His Trp Asp Arg Tyr Met
1               5                   10


<210> SEQ ID NO 101
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ala His Trp Asp Arg Tyr Met Gly Thr Leu
1               5                   10


<210> SEQ ID NO 102
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gln Arg Thr Glu Pro Pro Gly Thr Phe Leu
1               5                   10


<210> SEQ ID NO 103
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Thr His Lys Glu Asn Pro Val Val Asp Val
1               5                   10


<210> SEQ ID NO 104
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 104

Met Arg Arg Ala Ser Ser Ser Ser Ser Leu
1 5 10

<210> SEQ ID NO 105
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 105

Val Arg Leu Pro Thr Gly Gly Pro Leu Leu
1 5 10

<210> SEQ ID NO 106
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 106

Thr His Arg Ala Thr Pro Val Phe Leu Val
1 5 10

<210> SEQ ID NO 107
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 107

Lys Phe Tyr Ser Ser Ser Ser Asn Thr Leu
1 5 10

<210> SEQ ID NO 108
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 108

Lys Pro Met Thr Asn Asn Ala Arg Gln Met
1 5 10

<210> SEQ ID NO 109
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 109

Ala Ser Arg Arg Ala His Tyr Thr Ser Tyr 1 5 10

<210> SEQ ID NO 110
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 110

Leu Leu Thr Ile Met Ser Tyr Asp Arg Tyr
1 5 10

<210> SEQ ID NO 111
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 111

Arg Ile Arg Ser Lys Lys Lys Lys Thr Leu
1 5 10

<210> SEQ ID NO 112
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 112

Arg Pro Phe Ile His Ala Ser Ser Ser Met
1 5 10

<210> SEQ ID NO 113
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 113

Phe Gln His Lys Met Ser Gln Glu Gly Phe
1 5 10

<210> SEQ ID NO 114
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 114

Ser Pro Ser Ser Met Pro Leu His Pro Leu
1 5 10

<210> SEQ ID NO 115

<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Lys Tyr Val Asn Ile Phe Glu Asn Phe
1               5

<210> SEQ ID NO 116
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Arg Tyr Leu Asp Ile Lys Lys Ile Leu
1               5

<210> SEQ ID NO 117
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Arg Leu Ser Ser Leu Ser Ala Ala Tyr
1               5

<210> SEQ ID NO 118
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Asp Ala Glu Arg Phe Ser Asp Phe Tyr
1               5

<210> SEQ ID NO 119
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Asn Pro Asp Ser Val Asn Ala Ser Leu
1               5

<210> SEQ ID NO 120
<211> LENGTH: 9
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 120

Leu Pro Tyr Gly Leu Pro Thr Gly Leu
1 5

<210> SEQ ID NO 121
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 121

Arg Ser Gln Arg Val Arg Ala Ala Met
1 5

<210> SEQ ID NO 122
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 122

Ile Val Asp Asp Ile Gly His Gly Val
1 5

<210> SEQ ID NO 123
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 123

Thr Ile Val Asp Asp Ile Gly His Gly Val
1 5 10

<210> SEQ ID NO 124
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 124

Gly Glu Tyr Ile Ser Cys Val Ala Trp
1 5

<210> SEQ ID NO 125
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 125

Tyr Pro Pro Val Pro Gly Asn Lys Leu
1 5

<210> SEQ ID NO 126
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 126

Ser Pro Ile Phe Lys Gln Lys Lys Asn Leu
1 5 10

<210> SEQ ID NO 127
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 127

Asn Leu Arg Arg Ser Lys Lys Arg Ala Leu
1 5 10

<210> SEQ ID NO 128
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 128

Ala Pro Ala Ala Ala Ala Thr Ala Ala
1 5

<210> SEQ ID NO 129
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 129

Trp Leu Phe Leu Gly His Met Val Val
1 5

<210> SEQ ID NO 130
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 130

Trp Leu Leu Leu Gly Pro Met Val Val
1 5

<210> SEQ ID NO 131
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 131

Trp Val Tyr Glu Gly Thr Val Leu Leu
1               5

<210> SEQ ID NO 132
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 132

Val Leu Leu Ser Ala Thr Ile Phe Leu
1               5

<210> SEQ ID NO 133
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 133

Leu Leu Ser Ala Thr Ile Phe Leu Val
1               5

<210> SEQ ID NO 134
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 134

Phe Leu Val Phe Pro Phe Ile Ala Ile
1               5

<210> SEQ ID NO 135
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 135

Ala Ile Ser Cys Ser Tyr Gly Gln Val
1               5

<210> SEQ ID NO 136
<211> LENGTH: 9

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Ser Tyr Gly Arg Val Leu Phe Ala Val
1               5


<210> SEQ ID NO 137
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Arg Val Leu Phe Ala Val Tyr His Met
1               5


<210> SEQ ID NO 138
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Gly Gln Ala Leu Ala Glu Phe Ala Ala
1               5


<210> SEQ ID NO 139
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Gly Gln Ala Arg Gln Ser Arg Pro Val
1               5


<210> SEQ ID NO 140
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Arg Leu Leu His Pro His His Pro Leu
1               5


<210> SEQ ID NO 141
<211> LENGTH: 9
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 141

Ala Leu Leu Asp Gly Gly Leu Pro Ala
1               5

<210> SEQ ID NO 142
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Leu Leu Asp Gly Gly Leu Pro Ala Gly
1               5

<210> SEQ ID NO 143
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Phe Ile Ser Gly Arg Phe Pro Tyr Ser
1               5

<210> SEQ ID NO 144
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

His Ala Pro Ala Leu Asp Ala Pro Leu
1               5

<210> SEQ ID NO 145
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Ala Pro Ala Leu Asp Ala Pro Leu Phe
1               5

<210> SEQ ID NO 146
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

His Val Ser Asp Met Ser Val Val Leu
1 5

<210> SEQ ID NO 147
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 147

Val Pro Cys Val Cys Ala Val Arg Tyr
1 5

<210> SEQ ID NO 148
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 148

Thr Pro Trp Pro Pro Pro Pro Ala Thr
1 5

<210> SEQ ID NO 149
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 149

Gln Arg Trp Met Lys Val Asn Phe Glu Val
1 5 10

<210> SEQ ID NO 150
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 150

Ser Arg Phe Phe Ser Leu Val Lys Gln Met
1 5 10

<210> SEQ ID NO 151
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 151

Glu His Glu Glu Val Val Leu Glu Glu Leu
1 5 10

<210> SEQ ID NO 152
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 152

Asn Arg Glu Asn Arg Glu Gln Tyr Gln Leu
1 5 10

<210> SEQ ID NO 153
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 153

Ala Ala Ala Ala Leu His Met Gln Arg
1 5

<210> SEQ ID NO 154
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 154

Val Ala Gly Ala Val Gly Pro His Lys
1 5

<210> SEQ ID NO 155
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 155

Ser Ile Ser Ser Ala Ala Thr Pro Tyr
1 5

<210> SEQ ID NO 156
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 156

Ile Ser Ser Ala Ala Thr Pro Tyr Arg
1 5

<210> SEQ ID NO 157
<211> LENGTH: 9
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 157

Ser Ile Ala Lys Lys Ser Gly Gln Lys
1 5

<210> SEQ ID NO 158
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 158

Asp Leu Gln Lys Phe Lys Phe Leu Lys
1 5

<210> SEQ ID NO 159
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 159

Lys Thr Gln Leu Asn Pro Ser Ser Arg
1 5

<210> SEQ ID NO 160
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 160

Gln Leu Asn Pro Ser Ser Arg Gln Lys
1 5

<210> SEQ ID NO 161
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 161

Gly Ala Ser Ala Pro Ala Thr Ala Lys
1 5

<210> SEQ ID NO 162
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 162

Val Leu Tyr Val Val Arg Ser Leu Tyr
1 5

<210> SEQ ID NO 163
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 163

Leu Ser Ala Ile Arg Thr Val Ala Lys
1 5

<210> SEQ ID NO 164
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 164

Arg Ala Leu Phe Asn Arg Ala Gln Lys
1 5

<210> SEQ ID NO 165
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 165

Ala Ala Ser Glu Ser Pro Ser Leu Lys
1 5

<210> SEQ ID NO 166
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 166

Gly Asn Ser Ser Gly Ala Leu Leu Lys
1 5

<210> SEQ ID NO 167
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 167

Phe Leu Cys Val Phe Ser Ile Thr Lys
1 5

<210> SEQ ID NO 168
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 168

Met Phe Tyr Lys Ile Leu His Ser Phe
1 5

<210> SEQ ID NO 169
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 169

Arg Trp Met Lys Val Asn Phe Glu Val
1 5

<210> SEQ ID NO 170
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 170

Ser Val Ala Gly Phe Leu Ser Ser Leu
1 5

<210> SEQ ID NO 171
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 171

Ser Pro Thr Ala Leu Arg Pro Arg Leu
1 5

<210> SEQ ID NO 172
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 172

Ser Ile Phe Glu Glu Arg Thr Arg Tyr
1 5

<210> SEQ ID NO 173
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 173

Ala Thr Ser Ser Gln Thr Ser Val Tyr
1               5

<210> SEQ ID NO 174
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 174

Phe Tyr Ser Ser Ser Ser Asn Thr Leu
1               5

<210> SEQ ID NO 175
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 175

Leu Tyr Leu Ala Thr His Arg Arg Ile
1               5

<210> SEQ ID NO 176
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 176

Leu Thr Ile Met Ser Tyr Asp Arg Tyr
1               5

<210> SEQ ID NO 177
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 177

Gln Thr Asp Lys Asn Val Phe Arg Lys
1               5

<210> SEQ ID NO 178
<211> LENGTH: 9
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 178

Ser Pro Met Phe Lys Asn Thr Ser Val
1               5


<210> SEQ ID NO 179
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Arg Ala His Phe Ser Pro Ala Ser Leu
1               5


<210> SEQ ID NO 180
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Arg Pro Lys Gly Pro Trp Ser Ser Thr
1               5


<210> SEQ ID NO 181
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

His Val Lys Val Asn Gly Arg Val Tyr
1               5


<210> SEQ ID NO 182
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Ala Pro Ala Ala Ala Ala Thr Ala Ala Thr
1               5                   10


<210> SEQ ID NO 183
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 183

Ser Pro Gly Pro Arg Asn Ala Pro Ala
1               5

<210> SEQ ID NO 184
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 184

Ser Pro Gly Pro Arg Asn Ala Pro Ala Ala
1               5                   10

<210> SEQ ID NO 185
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 185

Glu Val Arg Ala Leu Leu Thr Gln Tyr
1               5

<210> SEQ ID NO 186
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 186

Pro Pro Pro Pro Ala Thr Thr Pro Phe
1               5

<210> SEQ ID NO 187
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 187

Ala Pro Thr Ala Val Gly Pro Pro Leu
1               5

<210> SEQ ID NO 188
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 188

Leu Val Trp Leu Leu Leu Gly Pro Met 1 5

<210> SEQ ID NO 189
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 189

Thr Val Leu Leu Ser Ala Thr Ile Phe
1 5

<210> SEQ ID NO 190
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 190

Phe Pro Phe Ile Ala Ile Ser Cys Ser
1 5

<210> SEQ ID NO 191
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 191

Thr Pro Glu Glu Gly Gly Gln Ala Leu
1 5

<210> SEQ ID NO 192
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 192

Leu Pro Val Thr Asp Thr Ser Ser Val
1 5

<210> SEQ ID NO 193
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 193

Ile Met Leu Leu Thr Asn Trp Arg Phe
1 5

<210> SEQ ID NO 194

<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 194

Arg Gly Ala Arg Ala Pro Ala Ala Trp
1 5

<210> SEQ ID NO 195
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 195

Tyr Ser Arg Arg Lys Phe Pro Ala Trp
1 5

<210> SEQ ID NO 196
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 196

Thr Gly Leu Pro His Ala Pro Ala Leu
1 5

<210> SEQ ID NO 197
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 197

Tyr Arg Val Leu Gln Cys Ala Asn Leu
1 5

<210> SEQ ID NO 198
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 198

Gln Ser Ala Gly Pro Gly Arg Pro Leu
1 5

<210> SEQ ID NO 199
<211> LENGTH: 9
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 199

Ala Val Ala Gly Glu Gly Arg Ala Leu
1 5

<210> SEQ ID NO 200
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 200

Val Ala Ser Gly Glu Asn Met Thr Leu
1 5

<210> SEQ ID NO 201
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 201

Thr Trp Val Tyr Glu Gly Thr Val Leu
1 5

<210> SEQ ID NO 202
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 202

Ile Ser Cys Ser Cys Gly Gln Val Leu
1 5

<210> SEQ ID NO 203
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 203

Ile Ser Cys Ser Tyr Gly Arg Val Leu
1 5

<210> SEQ ID NO 204
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 204

Phe Ala Val Tyr Arg Met Lys Ser Ala
1 5

<210> SEQ ID NO 205
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 205

Ala Glu Gly Glu Thr Glu Gly Ser Val
1 5

<210> SEQ ID NO 206
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 206

Met Glu Ala Gly Ala Gly Arg Asp Ser
1 5

<210> SEQ ID NO 207
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 207

Gly Glu Leu Met Val Val Thr Ala Ser
1 5

<210> SEQ ID NO 208
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 208

Lys Glu Asn Pro Val Val Asp Val Val
1 5

<210> SEQ ID NO 209
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 209

Cys Glu Gly Leu Asn Leu Leu Thr Ala
1 5

<210> SEQ ID NO 210
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 210

Arg Glu Lys Pro Tyr Asp Cys Met Ala
1 5

<210> SEQ ID NO 211
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 211

Leu Glu Arg Gly Ala Ser Ala Pro Ala
1 5

<210> SEQ ID NO 212
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 212

Glu Glu Leu Glu Val His Phe Lys Ile
1 5

<210> SEQ ID NO 213
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 213

Gln Glu Ser Val Pro Ile Gly Thr Ala
1 5

<210> SEQ ID NO 214
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 214

Ala Glu His Glu Glu Val Val Leu Glu
1 5

<210> SEQ ID NO 215
<211> LENGTH: 9

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 215

Glu Gln Tyr Gln Leu Val Ile Gln Ala
1 5

<210> SEQ ID NO 216
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 216

Val Gln Phe Ser Gln Leu Gln Glu Leu
1 5

<210> SEQ ID NO 217
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 217

Arg Arg Ala Ser Ser Ser Ser Ser Leu
1 5

<210> SEQ ID NO 218
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 218

Gln Lys Ser Asp Glu Asn Gln Tyr Leu
1 5

<210> SEQ ID NO 219
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 219

Thr His Arg Ala Thr Pro Val Phe Leu
1 5

<210> SEQ ID NO 220
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 220

His Arg Ala Thr Pro Val Phe Leu Val
1 5

<210> SEQ ID NO 221
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 221

Leu Arg Asp Gly Gln Ile Leu Glu Phe
1 5

<210> SEQ ID NO 222
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 222

Ser Arg Gln Lys Leu Phe Arg Glu Val
1 5

<210> SEQ ID NO 223
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 223

Ala Leu Phe Asn Arg Ala Gln Lys Leu
1 5

<210> SEQ ID NO 224
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 224

Gln Arg Glu Ala Leu Arg Gln Leu Leu
1 5

<210> SEQ ID NO 225
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 225

Asn Arg Glu Gln Tyr Gln Leu Val Ile
1 5

<210> SEQ ID NO 226
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 226

Lys Gln Pro Pro Ser Val Ser His Phe
1 5

<210> SEQ ID NO 227
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 227

Ala Pro Ser Leu Asp Leu Ser Asp Leu
1 5

<210> SEQ ID NO 228
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 228

Ser Pro Val Gly Pro Pro Phe Gly Leu
1 5

<210> SEQ ID NO 229
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 229

Met Ser Asn Leu Phe Leu Gly Ser Tyr
1 5

<210> SEQ ID NO 230
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 230

Arg Phe Leu Met Ser Met Arg Arg Leu
1 5

<210> SEQ ID NO 231
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 231

Gly Tyr Val Gln Gln Arg Arg Glu Phe
1 5

<210> SEQ ID NO 232
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 232

Asn Val Ala Ser Ala Ala Pro Ser Leu
1 5

<210> SEQ ID NO 233
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 233

Ala Met Gly Gly Glu Val Glu Arg Phe
1 5

<210> SEQ ID NO 234
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 234

Leu Gln Arg Glu Met Met Ser Asn Leu
1 5

<210> SEQ ID NO 235
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 235

Leu Leu Ala Thr Pro Arg Gln Leu Tyr
1 5

<210> SEQ ID NO 236
<211> LENGTH: 9
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 236

Glu Ser Phe Lys Leu Ser Asp Ser Tyr
1 5

<210> SEQ ID NO 237
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 237

Tyr Trp Ile Thr Tyr Glu Gln Thr Leu
1 5

<210> SEQ ID NO 238
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 238

Ser Glu Phe Gln Ala Ala Leu Ser Arg Lys Val Ala Glu Leu Val His
1 5 10 15

Phe Leu Leu Leu Lys Tyr Arg Ala Arg Glu Pro Val Thr Lys Ala
20 25 30

<210> SEQ ID NO 239
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 239

Thr Tyr Val Leu Ser Ile Val Pro Ser Gly Pro Leu Lys Ala Glu Ile
1 5 10 15

Ala Gln Arg Leu Glu Asp Val Phe Ala Gly Lys Asn Thr Asp Leu
20 25 30

<210> SEQ ID NO 240
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 240

Lys Thr Arg Pro Ile Leu Ser Pro Leu Thr Lys Gly Ile Leu Gly Phe
1 5 10 15

Val Phe Thr Leu Thr Val Pro Ser Glu Arg Gly Leu Gln Arg Arg
20 25 30

<210> SEQ ID NO 241
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 241

Lys Gly His Gly His Ser Tyr Thr Thr Ala Glu Glu Ala Ala Gly Ile
1 5 10 15

Gly Ile Leu Thr Val Ile Leu Gly Val Leu Leu Leu Ile Gly Cys Trp
20 25 30

<210> SEQ ID NO 242
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 242

Asn Lys Ile Thr Tyr Gly Ala Cys Pro Lys Tyr Val Lys Gln Asn Thr
1 5 10 15

Leu Lys Leu Ala Thr Gly Met Arg Asn Val Pro Glu Lys Gln Thr
20 25 30

<210> SEQ ID NO 243
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 243

Ala Ala Lys Gln Leu Thr Pro Glu Val Arg Ala Leu Leu Thr Gln Tyr
1 5 10 15

Glu Thr

<210> SEQ ID NO 244
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 244

Gly Gly Phe Val Leu Gly Leu Leu Phe Leu Gly Ala Gly Leu Phe Leu
1 5 10 15

Tyr Phe Arg Asn Gln Lys Gly His Ser Gly Leu Gln Pro Thr Gly
20 25 30

<210> SEQ ID NO 245
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 245

Thr Asp Leu Cys Phe Leu Asn Ser Pro Ile Phe Lys Gln Lys Lys Asn
1 5 10 15

Leu Arg Arg Ser Lys Lys Arg Ala Leu Glu Val Ser Pro Ala Lys
20 25 30

<210> SEQ ID NO 246
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 246

Glu Asp Ala Asp Glu Pro Gly Arg Val Pro Thr Glu Asp Tyr Met Ile
1 5 10 15

His Ile Ile Glu Lys Trp
20

<210> SEQ ID NO 247
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 247

Leu Glu Lys Ser Ala Val Leu Gln Glu Ala Arg Ile Phe Asn Glu Ile
1 5 10 15

Pro Ile Asn Pro Arg Arg Cys Leu His Ile Leu Thr Lys Ile Leu
20 25 30

<210> SEQ ID NO 248
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 248

Glu Arg Pro Val Arg Tyr Ile Arg Lys Pro Ile Asp Tyr Thr Ile Val
1 5 10 15

Asp Asp Ile Gly His Gly Val Lys Trp Leu Leu Arg Phe Lys Val
20 25 30

<210> SEQ ID NO 249
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 249

Ile Leu Gln Leu Leu Gln Met Glu Gln Pro Gly Glu Tyr Ile Ser Cys
1 5 10 15

Val Ala Trp Ile Lys Glu Gly Asn Tyr Leu Ala Val Gly Thr Ser
20 25 30

<210> SEQ ID NO 250
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 250

Gly Pro Leu Pro Arg Glu Gly Ser Gly Gly Ser Thr Ser Asp Tyr Leu
1 5 10 15

Ser Gln Ser Tyr Ser Tyr Ser Ser Ile Leu Asn Lys Ser Glu Thr
20 25 30

<210> SEQ ID NO 251
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 251

Arg Phe Arg Pro Asp Phe Lys Arg Lys Phe Ala Asp Phe Phe Glu Met
1 5 10 15

Asp Thr Ile Ser Glu Tyr Ile Tyr His Cys Asn Ala Gln Asn Pro
20 25 30

<210> SEQ ID NO 252
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 252

Trp Trp Val Thr Val Gln Pro Pro Ala Arg Arg Met Gly Trp Leu Ser
1 5 10 15

Leu Leu Leu Leu Leu Thr Gln Cys Leu Gly Val Pro Gly Gln Arg
20 25 30

<210> SEQ ID NO 253
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 253

Pro Pro Arg Pro Val Asn Ala Ala Ser Pro Thr Asn Val Gln Ala Leu
1 5 10 15

Ser Val Tyr Ser Val Pro Ala Tyr Thr Ser Pro Pro Ser Phe Phe
20 25 30

<210> SEQ ID NO 254
<211> LENGTH: 31

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 254

Val Gly Val Gly Thr Ser Tyr Gly Leu Pro Gln Ala Arg Arg Ile Leu
1               5                   10                  15

Leu Ala Thr Pro Arg Gln Leu Tyr Lys Ser Ser Asn Met Thr Gln
            20                  25                  30


<210> SEQ ID NO 255
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 255

His Val Lys Gly Ala Asn Ala Gly Val Gln Thr Phe Leu Gly Ile Ser
1               5                   10                  15

Phe Ala Lys Pro Pro Leu Gly Pro Leu Arg Phe Ala Pro Pro Glu
            20                  25                  30


<210> SEQ ID NO 256
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Ala Thr Phe Ser Ser Asn Gln Ser Asp Asn Gly Leu Asp Ser Asp Tyr
1               5                   10                  15

Asp Gln Pro Val Glu Gly Val Ile Thr Asn Gly Ser Lys Val Glu
            20                  25                  30


<210> SEQ ID NO 257
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 257

Ser Gly Gln Lys Lys Leu His Gly Leu Gln Ala Ile Leu Val His Val
1               5                   10                  15

Ala Ser Gly Thr Thr Ala Ile Thr Ala Thr Ala Thr Gly Tyr Gln
            20                  25                  30


<210> SEQ ID NO 258
<211> LENGTH: 196
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 258

Ser Glu Phe Gln Ala Ala Leu Ser Arg Lys Val Ala Glu Leu Val His
1 5 10 15

Phe Leu Leu Leu Lys Tyr Arg Ala Arg Glu Pro Val Thr Lys Ala Gly
20 25 30

Gly Ser Gly Gly Gly Gly Ser Gly Gly Thr Tyr Val Leu Ser Ile Val
35 40 45

Pro Ser Gly Pro Leu Lys Ala Glu Ile Ala Gln Arg Leu Glu Asp Val
50 55 60

Phe Ala Gly Lys Asn Thr Asp Leu Gly Gly Ser Gly Gly Gly Gly Ser
65 70 75 80

Gly Gly Lys Thr Arg Pro Ile Leu Ser Pro Leu Thr Lys Gly Ile Leu
85 90 95

Gly Phe Val Phe Thr Leu Thr Val Pro Ser Glu Arg Gly Leu Gln Arg
100 105 110

Arg Gly Gly Ser Gly Gly Gly Gly Ser Gly Gly Lys Gly His Gly His
115 120 125

Ser Tyr Thr Thr Ala Glu Glu Ala Ala Gly Ile Gly Ile Leu Thr Val
130 135 140

Ile Leu Gly Val Leu Leu Leu Ile Gly Cys Trp Gly Gly Ser Gly Gly
145 150 155 160

Gly Gly Ser Gly Gly Asn Lys Ile Thr Tyr Gly Ala Cys Pro Lys Tyr
165 170 175

Val Lys Gln Asn Thr Leu Lys Leu Ala Thr Gly Met Arg Asn Val Pro
180 185 190

Glu Lys Gln Thr
195

<210> SEQ ID NO 259
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 259

Ala Ala Lys Gln Leu Thr Pro Glu Val Arg Ala Leu Leu Thr Gln Tyr
1 5 10 15

Glu Thr Gly Gly Ser Gly Gly Gly Gly Ser Gly Gly Gly Gly Phe Val
20 25 30

Leu Gly Leu Leu Phe Leu Gly Ala Gly Leu Phe Leu Tyr Phe Arg Asn
35 40 45

Gln Lys Gly His Ser Gly Leu Gln Pro Thr Gly Gly Gly Ser Gly Gly
50 55 60

Gly Gly Ser Gly Gly Thr Asp Leu Cys Phe Leu Asn Ser Pro Ile Phe
65 70 75 80

Lys Gln Lys Lys Asn Leu Arg Arg Ser Lys Lys Arg Ala Leu Glu Val
85 90 95

Ser Pro Ala Lys Gly Gly Ser Gly Gly Gly Gly Ser Gly Gly Glu Asp
100 105 110

Ala Asp Glu Pro Gly Arg Val Pro Thr Glu Asp Tyr Met Ile His Ile
115 120 125

Ile Glu Lys Trp Gly Gly Ser Gly Gly Gly Gly Ser Gly Gly Leu Glu
130 135 140

```
Lys Ser Ala Val Leu Gln Glu Ala Arg Ile Phe Asn Glu Ile Pro Ile
145                 150                 155                 160

Asn Pro Arg Arg Cys Leu His Ile Leu Thr Lys Ile Leu
                165                 170


<210> SEQ ID NO 260
<211> LENGTH: 195
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 260

Glu Arg Pro Val Arg Tyr Ile Arg Lys Pro Ile Asp Tyr Thr Ile Val
1               5                   10                  15

Asp Asp Ile Gly His Gly Val Lys Trp Leu Leu Arg Phe Lys Val Gly
            20                  25                  30

Gly Ser Gly Gly Gly Gly Ser Gly Gly Ile Leu Gln Leu Leu Gln Met
        35                  40                  45

Glu Gln Pro Gly Glu Tyr Ile Ser Cys Val Ala Trp Ile Lys Glu Gly
    50                  55                  60

Asn Tyr Leu Ala Val Gly Thr Ser Gly Gly Ser Gly Gly Gly Gly Ser
65                  70                  75                  80

Gly Gly Gly Pro Leu Pro Arg Glu Gly Ser Gly Gly Ser Thr Ser Asp
                85                  90                  95

Tyr Leu Ser Gln Ser Tyr Ser Tyr Ser Ser Ile Leu Asn Lys Ser Glu
            100                 105                 110

Thr Gly Gly Ser Gly Gly Gly Gly Ser Gly Gly Arg Phe Arg Pro Asp
        115                 120                 125

Phe Lys Arg Lys Phe Ala Asp Phe Phe Glu Met Asp Thr Ile Ser Glu
    130                 135                 140

Tyr Ile Tyr His Cys Asn Ala Gln Asn Pro Gly Gly Ser Gly Gly Gly
145                 150                 155                 160

Gly Ser Gly Gly Trp Trp Val Thr Val Gln Pro Pro Ala Arg Arg Met
                165                 170                 175

Gly Trp Leu Ser Leu Leu Leu Leu Leu Thr Gln Cys Leu Gly Val Pro
            180                 185                 190

Gly Gln Arg
        195


<210> SEQ ID NO 261
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Asp Gly Gln Arg Leu His Ile His Ser Phe Thr Ala Asn Ser Phe Arg
1               5                   10                  15

Gly Leu Thr Gly His Ser His Arg Ser
            20                  25


<210> SEQ ID NO 262
<211> LENGTH: 26
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Met Arg Val Thr Ala Pro Arg Thr Leu Ile Leu Leu Leu Ser Gly Ala
1               5                   10                  15

Leu Ala Leu Thr Glu Thr Trp Ala Gly Ser
            20                  25


<210> SEQ ID NO 263
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Gly Gly Ser Gly Gly Gly Gly Ser Gly Gly
1               5                   10


<210> SEQ ID NO 264
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Gly Gly Ser Leu Gly Gly Gly Gly Ser Gly
1               5                   10


<210> SEQ ID NO 265
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 265

Ile Val Gly Ile Val Ala Gly Leu Ala Val Leu Ala Val Val Val Ile
1               5                   10                  15

Gly Ala Val Val Ala Thr Val Met Cys Arg Arg Lys Ser Ser Gly Gly
            20                  25                  30

Lys Gly Gly Ser Tyr Ser Gln Ala Ala Ser Ser Asp Ser Ala Gln Gly
        35                  40                  45

Ser Asp Val Ser Leu Thr Ala
    50                  55


<210> SEQ ID NO 266
<211> LENGTH: 262
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 266
gctcgctttc ttgctgtcca atttctatta aaggttcctt tgttccctaa gtccaactac 60
taaactgggg gatattatga agggccttga gcatctggat tctgcctaat aaaaaacatt 120
tattttcatt ggctcgcttt cttgctgtcc aatttctatt aaaggttcct ttgttcccta 180
agtccaacta ctaaactggg ggatattatg aagggccttg agcatctgga ttctgcctaa 240
taaaaaacat ttattttcat tg 262

<210> SEQ ID NO 267
<211> LENGTH: 897
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 267
atgagagtga cagcccctag aacactgatc ctgctgctgt ctggtgccct ggctctgaca 60
gaaacatggg ctggaagctc tagaggagga tctggcggag gtggtagtgg cggatctgaa 120
tttcaggccg ctctgtccag aaaggtggcc gagctggtgc actttctgct gctgaagtac 180
cgggccagag aacccgtgac aaaagctggt ggttctggcg gtggcggtag cggaggaaca 240
tacgtgctga gcattgtgcc tagcggccct ctgaaggccg agattgctca gagactggaa 300
gatgtgttcg ccggcaagaa caccgatctc ggaggcagcg gcggaggcgg ctctggtgga 360
aaaacaagac ccattctgag ccctctgacc aagggcatcc tgggcttcgt gttcaccctg 420
acagtgccat ctgagagagg cctgcagaga agaggtggca gcggaggcgg tggatcaggc 480
ggaaaaggac acggccacag ctacaccaca gccgaagaag ccgccggaat cggaatcctg 540
accgtgattc tgggagtgct gctgctcatc ggctgttggg gcggaagtgg tggcggtgga 600
agcggcggaa acaagatcac atatggcgcc tgtcctaaat acgtgaagca gaacaccctg 660
aagctggcca ccggcatgag aaacgtgcca gagaaacaga caggcggcag ccttggaggc 720
ggaggtagtg gaatcgtggg aattgtggct ggcctggctg tgctggccgt ggtggttatt 780
ggagctgtgg tggccacagt gatgtgcaga agaaagtcca gcggcggcaa aggcggaagc 840
tattctcagg ccgccagcag cgattctgcc cagggatctg atgtgtccct gaccgct 897

<210> SEQ ID NO 268
<211> LENGTH: 299
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 268

Met Arg Val Thr Ala Pro Arg Thr Leu Ile Leu Leu Leu Ser Gly Ala
1 5 10 15

Leu Ala Leu Thr Glu Thr Trp Ala Gly Ser Ser Arg Gly Gly Ser Gly
20 25 30

Gly Gly Gly Ser Gly Gly Ser Glu Phe Gln Ala Ala Leu Ser Arg Lys
35 40 45

Val Ala Glu Leu Val His Phe Leu Leu Leu Lys Tyr Arg Ala Arg Glu
50 55 60

Pro Val Thr Lys Ala Gly Gly Ser Gly Gly Gly Gly Ser Gly Gly Thr

```
65                  70                  75                  80

Tyr Val Leu Ser Ile Val Pro Ser Gly Pro Leu Lys Ala Glu Ile Ala
                85                  90                  95

Gln Arg Leu Glu Asp Val Phe Ala Gly Lys Asn Thr Asp Leu Gly Gly
            100                 105                 110

Ser Gly Gly Gly Gly Ser Gly Gly Lys Thr Arg Pro Ile Leu Ser Pro
        115                 120                 125

Leu Thr Lys Gly Ile Leu Gly Phe Val Phe Thr Leu Thr Val Pro Ser
    130                 135                 140

Glu Arg Gly Leu Gln Arg Arg Gly Gly Ser Gly Gly Gly Gly Ser Gly
145                 150                 155                 160

Gly Lys Gly His Gly His Ser Tyr Thr Thr Ala Glu Glu Ala Ala Gly
                165                 170                 175

Ile Gly Ile Leu Thr Val Ile Leu Gly Val Leu Leu Leu Ile Gly Cys
            180                 185                 190

Trp Gly Gly Ser Gly Gly Gly Gly Ser Gly Gly Asn Lys Ile Thr Tyr
        195                 200                 205

Gly Ala Cys Pro Lys Tyr Val Lys Gln Asn Thr Leu Lys Leu Ala Thr
    210                 215                 220

Gly Met Arg Asn Val Pro Glu Lys Gln Thr Gly Gly Ser Leu Gly Gly
225                 230                 235                 240

Gly Gly Ser Gly Ile Val Gly Ile Val Ala Gly Leu Ala Val Leu Ala
                245                 250                 255

Val Val Val Ile Gly Ala Val Val Ala Thr Val Met Cys Arg Arg Lys
            260                 265                 270

Ser Ser Gly Gly Lys Gly Gly Ser Tyr Ser Gln Ala Ala Ser Ser Asp
        275                 280                 285

Ser Ala Gln Gly Ser Asp Val Ser Leu Thr Ala
    290                 295
```

<210> SEQ ID NO 269
<211> LENGTH: 894
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 269

```
atgagagtga cagcccctcg gacactgatc ctgctgcttt ctggtgccct ggctctgaca     60

gaaacatggg ctggaagctc tagaggagga tctggcggag gtggaagtgg cggagaaaga    120

cccgtgcggt acatcagaaa gcccatcgac tacaccatcg tggacgacat cggacacggc    180

gtgaagtggc tgctgagatt caaagttggc ggctctggtg gcggaggcag cggaggaatt    240

ctgcagctgc tgcaaatgga acagcccggc gagtacatct cctgcgtggc ctggatcaaa    300

gagggcaact atctggccgt gggcacatca ggcggtagcg gcggaggcgg ctcaggcgga    360

ggacctttgc ctagagaagg ttctggcggc agcaccagcg attacctgag ccagagctac    420

agctacagca gcatcctgaa caagagcgag acaggcggaa gcggaggcgg aggaagcggt    480

ggaagattca gacccgactt caagcggaag ttcgccgact tcttcgagat ggacaccatc    540

agcgagtata tctaccactg caacgcccag aatcctggcg gatcaggtgg tggtggctcc    600

ggtggatggt gggttacagt tcagcctcct gccagaagaa tgggctggct gtctctgctg    660

ctgctcctga cacagtgtct gggagtgcca ggacagagag gcggatctct tggaggtggc    720
```

ggatctggca tcgtgggaat tgtggctgga ctggctgtgc tggcagtggt ggttattgga 780
gccgtggtgg ccacagtgat gtgcagaaga aagagcagcg gcggcaaagg cggcagctat 840
tctcaggccg cctctagcga ttctgcccag ggctctgatg tgtctctgac agct 894

<210> SEQ ID NO 270
<211> LENGTH: 298
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 270

Met Arg Val Thr Ala Pro Arg Thr Leu Ile Leu Leu Leu Ser Gly Ala
1 5 10 15

Leu Ala Leu Thr Glu Thr Trp Ala Gly Ser Ser Arg Gly Gly Ser Gly
20 25 30

Gly Gly Gly Ser Gly Gly Glu Arg Pro Val Arg Tyr Ile Arg Lys Pro
35 40 45

Ile Asp Tyr Thr Ile Val Asp Asp Ile Gly His Gly Val Lys Trp Leu
50 55 60

Leu Arg Phe Lys Val Gly Gly Ser Gly Gly Gly Gly Ser Gly Gly Ile
65 70 75 80

Leu Gln Leu Leu Gln Met Glu Gln Pro Gly Glu Tyr Ile Ser Cys Val
85 90 95

Ala Trp Ile Lys Glu Gly Asn Tyr Leu Ala Val Gly Thr Ser Gly Gly
100 105 110

Ser Gly Gly Gly Gly Ser Gly Gly Gly Pro Leu Pro Arg Glu Gly Ser
115 120 125

Gly Gly Ser Thr Ser Asp Tyr Leu Ser Gln Ser Tyr Ser Tyr Ser Ser
130 135 140

Ile Leu Asn Lys Ser Glu Thr Gly Gly Ser Gly Gly Gly Gly Ser Gly
145 150 155 160

Gly Arg Phe Arg Pro Asp Phe Lys Arg Lys Phe Ala Asp Phe Phe Glu
165 170 175

Met Asp Thr Ile Ser Glu Tyr Ile Tyr His Cys Asn Ala Gln Asn Pro
180 185 190

Gly Gly Ser Gly Gly Gly Gly Ser Gly Gly Trp Trp Val Thr Val Gln
195 200 205

Pro Pro Ala Arg Arg Met Gly Trp Leu Ser Leu Leu Leu Leu Leu Thr
210 215 220

Gln Cys Leu Gly Val Pro Gly Gln Arg Gly Gly Ser Leu Gly Gly Gly
225 230 235 240

Gly Ser Gly Ile Val Gly Ile Val Ala Gly Leu Ala Val Leu Ala Val
245 250 255

Val Val Ile Gly Ala Val Val Ala Thr Val Met Cys Arg Arg Lys Ser
260 265 270

Ser Gly Gly Lys Gly Gly Ser Tyr Ser Gln Ala Ala Ser Ser Asp Ser
275 280 285

Ala Gln Gly Ser Asp Val Ser Leu Thr Ala
290 295

<210> SEQ ID NO 271
<211> LENGTH: 828

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 271

atgagagtga cagcccctcg gacactgatc ctgctgcttt ctggtgccct ggctctgaca     60

gaaacatggg ctggaagctc tagaggagga tctggcggag gtggaagtgg cggagctgct    120

aaacagctga cacctgaagt tcgggccctg ctgacccagt atgagacagg cggttctggt    180

ggcggaggca gcggaggcgg aggatttgtt ctgggactgc tgtttctcgg agccggcctg    240

ttcctgtact tccggaatca gaagggccac agcggcctgc aacctactgg cggtggctca    300

ggtggtggtg gttctggcgg aaccgatctg tgcttcctga acagccccat cttcaagcag    360

aagaagaacc tgcggcggag caagaaaaga gccctggaag tctctcctgc caaaggcggt    420

agtggtggtg gcggatcagg cggagaagat gccgatgaac ctggcagagt gcccaccgag    480

gactacatga tccacatcat cgagaagtgg ggcggtagtg gcggcggagg aagcggtgga    540

cttgaaaaat ctgccgtgct gcaagaggcc cggatcttca acgagatccc catcaatccc    600

agacggtgcc tgcacatcct gaccaagatt ctcggcggct ctcttggagg tggcggctct    660

ggtattgtgg gaattgtggc tggactggcc gtgctggctg tggtggttat tggagcagtg    720

gtggccacag tgatgtgcag aagaaagagc agcggcggca aaggcggcag ctattctcag    780

gccgctagca gcgattctgc ccagggatct gatgtgtctc tgaccgct                 828


<210> SEQ ID NO 272
<211> LENGTH: 276
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 272

Met Arg Val Thr Ala Pro Arg Thr Leu Ile Leu Leu Leu Ser Gly Ala
1               5                   10                  15

Leu Ala Leu Thr Glu Thr Trp Ala Gly Ser Ser Arg Gly Gly Ser Gly
            20                  25                  30

Gly Gly Gly Ser Gly Gly Ala Ala Lys Gln Leu Thr Pro Glu Val Arg
        35                  40                  45

Ala Leu Leu Thr Gln Tyr Glu Thr Gly Gly Ser Gly Gly Gly Gly Ser
    50                  55                  60

Gly Gly Gly Gly Phe Val Leu Gly Leu Leu Phe Leu Gly Ala Gly Leu
65                  70                  75                  80

Phe Leu Tyr Phe Arg Asn Gln Lys Gly His Ser Gly Leu Gln Pro Thr
                85                  90                  95

Gly Gly Gly Ser Gly Gly Gly Gly Ser Gly Gly Thr Asp Leu Cys Phe
            100                 105                 110

Leu Asn Ser Pro Ile Phe Lys Gln Lys Lys Asn Leu Arg Arg Ser Lys
        115                 120                 125

Lys Arg Ala Leu Glu Val Ser Pro Ala Lys Gly Gly Ser Gly Gly Gly
    130                 135                 140

Gly Ser Gly Gly Glu Asp Ala Asp Glu Pro Gly Arg Val Pro Thr Glu
145                 150                 155                 160
```

```
Asp Tyr Met Ile His Ile Ile Glu Lys Trp Gly Gly Ser Gly Gly Gly
                165                 170                 175

Gly Ser Gly Gly Leu Glu Lys Ser Ala Val Leu Gln Glu Ala Arg Ile
            180                 185                 190

Phe Asn Glu Ile Pro Ile Asn Pro Arg Arg Cys Leu His Ile Leu Thr
        195                 200                 205

Lys Ile Leu Gly Gly Ser Leu Gly Gly Gly Gly Ser Gly Ile Val Gly
    210                 215                 220

Ile Val Ala Gly Leu Ala Val Leu Ala Val Val Val Ile Gly Ala Val
225                 230                 235                 240

Val Ala Thr Val Met Cys Arg Arg Lys Ser Ser Gly Gly Lys Gly Gly
                245                 250                 255

Ser Tyr Ser Gln Ala Ala Ser Ser Asp Ser Ala Gln Gly Ser Asp Val
            260                 265                 270

Ser Leu Thr Ala
        275
```

<210> SEQ ID NO 273
<211> LENGTH: 4137
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 273

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattgaagg aaggccgtca    360

aggccgcatc ggatccgcta gcgccaccat gtggcctcct ggatctgctt ctcagcctcc    420

tccatctcct gccgctgcta caggacttca tcctgccgca agacccgtgt ctctgcagtg    480

cagactgagc atgtgccccg ccagatctct gctgctggtg gctacactgg tgctgctgga    540

tcatctgagc ctggccagaa acctgccagt ggccacgcct gatcctggca tgtttccttg    600

tctgcaccac agccagaacc tgctgagagc cgtgtccaac atgctgcaga aggccagaca    660

gaccctggaa ttctacccct gcaccagcga ggaaatcgac cacgaggaca tcaccaagga    720

caagaccagc accgtggaag cctgcctgcc tctggaactg accaagaacg agagctgcct    780

gaacagcaga gagacatcct tcatcaccaa cggctcttgc ctggcctcca gaaagacctc    840

cttcatgatg gccctgtgcc tgagcagcat ctacgaggac ctgaagatgt accaggtgga    900

attcaagacc atgaacgcca agctgctgat ggaccccaag cggcagatct tcctggacca    960

gaatatgctg gccgtgatcg acgagctgat gcaggccctg aacttcaaca gcgagacagt   1020

gccccagaag tccagcctgg aagaacccga cttctacaag accaagatca agctgtgcat   1080

cctgctgcac gccttccgga tcagagccgt gaccatcgac agagtgatga gctacctgaa   1140

cgccagcccg cgggccacga acttctctct gttaaagcaa gcaggagacg tggaagaaaa   1200

ccccggtcct gctagcgcca ccatgtgtca ccagcagctg gtcatcagct ggttcagcct   1260

ggtgttcctg gcctctcctc tggtggccat ctgggagctg aagaaagacg tgtacgtggt   1320
```

```
ggaactggac tggtatcccg atgctcctgg cgagatggtg gtgctgacct gcgataccccc   1380
tgaagaggac ggcatcacct ggacactgga tcagtctagc gaggtgctcg gcagcggcaa   1440
gaccctgacc atccaagtga aagagtttgg cgacgccggc cagtacacct gtcacaaagg   1500
cggagaagtg ctgagccaca gcctgctgct gctccacaag aaagaggatg gcatttggag   1560
caccgacatc ctgaaggacc agaaagagcc caagaacaag accttcctga gatgcgaggc   1620
caagaactac agcggccggt tcacatgttg gtggctgacc accatcagca ccgacctgac   1680
cttcagcgtg aagtccagca gaggcagcag tgatcctcag ggcgttacat gtggcgccgc   1740
tacactgtct gccgaaagag tgcggggcga caacaaagaa tacgagtaca gcgtggaatg   1800
ccaagaggac agcgcctgtc cagccgccga agagtctctg cctatcgaag tgatggtgga   1860
cgccgtgcac aagctgaagt acgagaacta cacctccagc tttttcatcc gggacatcat   1920
caagcccgat cctccaaaga acctgcagct gaagcctctg aagaacagca gacaggtgga   1980
agtgtcctgg gagtaccccg acacctggtc tacaccccac agctacttca gcctgacctt   2040
ttgcgtgcaa gtgcagggca agtccaagcg cgagaaaaag gaccgggtgt tcaccgacaa   2100
gaccagcgcc accgtgatct gcagaaagaa cgccagcatc agcgtcagag cccaggaccg   2160
gtactacagc agctcttgga gcgaatgggc cagcgtgcca tgttctccgc ggctcgagta   2220
gtctagagct gggcctcatg ggccttcctt tcactgcccg ctttccagtc gggaaacctg   2280
tcgtgccagc tgcattaaca tggtcatagc tgtttccttg cgtattgggc gctctccgct   2340
tcctcgctca ctgactcgct gcgctcggtc gttcgggtaa agcctggggt gcctaatgag   2400
caaaaggcca gcaaaaggcc aggaaccgta aaaaggccgc gttgctggcg tttttccata   2460
ggctccgccc ccctgacgag catcacaaaa atcgacgctc aagtcagagg tggcgaaacc   2520
cgacaggact ataaagatac caggcgtttc cccctggaag ctccctcgtg cgctctcctg   2580
ttccgaccct gccgcttacc ggatacctgt ccgcctttct cccttcggga agcgtggcgc   2640
tttctcatag ctcacgctgt aggtatctca gttcggtgta ggtcgttcgc tccaagctgg   2700
gctgtgtgca cgaacccccc gttcagcccg accgctgcgc cttatccggt aactatcgtc   2760
ttgagtccaa cccggtaaga cacgacttat cgccactggc agcagccact ggtaacagga   2820
ttagcagagc gaggtatgta ggcggtgcta cagagttctt gaagtggtgg cctaactacg   2880
gctacactag aagaacagta tttggtatct gcgctctgct gaagccagtt accttcggaa   2940
aaagagttgg tagctcttga tccggcaaac aaaccaccgc tggtagcggt ggtttttttg   3000
tttgcaagca gcagattacg cgcagaaaaa aaggatctca agaagatcct ttgatctttt   3060
ctacggggtc tgacgctcag tggaacgaaa actcacgtta agggattttg gtcatgagat   3120
tatcaaaaag gatcttcacc tagatccttt taaattaaaa atgaagtttt aaatcaatct   3180
aaagtatata tgagtaaact tggtctgaca gttattagaa aaattcatcc agcagacgat   3240
aaaacgcaat acgctggcta tccggtgccg caatgccata cagcaccaga aaacgatccg   3300
cccattcgcc gcccagttct tccgcaatat cacgggtggc cagcgcaata tcctgataac   3360
gatccgccac gcccagacgg ccgcaatcaa taaagccgct aaaacggcca ttttccacca   3420
taatgttcgg caggcacgca tcaccatggg tcaccaccag atcttcgcca tccggcatgc   3480
tcgctttcag acgcgcaaac agctctgccg gtgccaggcc ctgatgttct tcatccagat   3540
catcctgatc caccaggccc gcttccatac gggtacgcgc acgttcaata cgatgtttcg   3600
cctgatgatc aaacggacag gtcgccgggt ccagggtatg cagacgacgc atggcatccg   3660
```

ccataatgct cactttttct gccggcgcca gatggctaga cagcagatcc tgacccggca 3720
cttcgcccag cagcagccaa tcacggcccg cttcggtcac cacatccagc accgccgcac 3780
acggaacacc ggtggtggcc agccagctca gacgcgccgc ttcatcctgc agctcgttca 3840
gcgcaccgct cagatcggtt ttcacaaaca gcaccggacg accctgcgcg ctcagacgaa 3900
acaccgccgc atcagagcag ccaatggtct gctgcgccca atcatagcca aacagacgtt 3960
ccacccacgc tgccgggcta cccgcatgca ggccatcctg ttcaatcata ctcttccttt 4020
ttcaatatta ttgaagcatt tatcagggtt attgtctcat gagcggatac atatttgaat 4080
gtatttagaa aaataaacaa ataggggttc cgcgcacatt tccccgaaaa gtgccac 4137

<210> SEQ ID NO 274
<211> LENGTH: 5657
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 274
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagt 900
taagcttggt accgagctcg gatctatgga aagggtccaa cccctggaag agaatgtggg 960
aaatgcagcc aggccaagat tcgagaggaa caagctattg ctggtggcct ctgtaattca 1020
gggactgggg ctgctcctgt gcttcaccta catctgcctg cacttctctg ctcttcaggt 1080
atcacatcgg tatcctcgaa ttcaaagtat caaagtacaa tttaccgaat ataagaagga 1140
gaaaggtttc atcctcactt cccaaaagga ggatgaaatc atgaaggtgc agaacaactc 1200
agtcatcatc aactgtgatg ggttttatct catctccctg aagggctact tctcccagga 1260
agtcaacatt agccttcatt accagaagga tgaggagccc ctcttccaac tgaagaaggt 1320
caggtctgtc aactccttga tggtggcctc tctgacttac aaagacaaag tctacttgaa 1380
tgtgaccact gacaatacct ccctggatga cttccatgtg aatggcggag aactgattct 1440
tatccatcaa aatcctggtg aattctgtgt cctttgagaa ttctgcagat atccagcaca 1500
gtggcggccg ctcgaggtca cccattcgaa caaaaactca tctcagaaga ggatctgaat 1560

```
atgcataccg gtcatcatca ccatcaccat tgagtttaaa cccgctgatc agcctcgact   1620
gtgccttcta gttgccagcc atctgttgtt tgcccctccc ccgtgccttc cttgaccctg   1680
gaaggtgcca ctcccactgt cctttcctaa taaaatgagg aaattgcatc gcattgtctg   1740
agtaggtgtc attctattct ggggggtggg gtggggcagg acagcaaggg ggaggattgg   1800
gaagacaata gcaggcatgc tggggatgcg gtgggctcta tggcttctga ggcggaaaga   1860
accagctggg gctctagggg gtatccccac gcgccctgta gcggcgcatt aagcgcggcg   1920
ggtgtggtgg ttacgcgcag cgtgaccgct acacttgcca gcgccctagc gcccgctcct   1980
ttcgctttct tcccttcctt tctcgccacg ttcgccggct ttccccgtca agctctaaat   2040
cgggggctcc ctttagggtt ccgatttagt gctttacggc acctcgaccc caaaaaactt   2100
gattagggtg atggttcacg tagtgggcca tcgccctgat agacggtttt tcgccctttg   2160
acgttggagt ccacgttctt taatagtgga ctcttgttcc aaactggaac aacactcaac   2220
cctatctcgg tctattcttt tgatttataa gggattttgc cgatttcggc ctattggtta   2280
aaaaatgagc tgatttaaca aaaatttaac gcgaattaat tctgtggaat gtgtgtcagt   2340
tagggtgtgg aaagtcccca ggctccccag caggcagaag tatgcaaagc atgcatctca   2400
attagtcagc aaccaggtgt ggaaagtccc caggctcccc agcaggcaga agtatgcaaa   2460
gcatgcatct caattagtca gcaaccatag tcccgcccct aactccgccc atcccgcccc   2520
taactccgcc cagttccgcc cattctccgc cccatggctg actaattttt tttatttatg   2580
cagaggccga ggccgcctct gcctctgagc tattccagaa gtagtgagga ggcttttttg   2640
gaggcctagg cttttgcaaa aagctcccgg gagcttgtat atccattttc ggatctgatc   2700
agcacgtgtt gacaattaat catcggcata gtatatcggc atagtataat acgacaaggt   2760
gaggaactaa accatggcca agcctttgtc tcaagaagaa tccaccctca ttgaaagagc   2820
aacggctaca atcaacagca tccccatctc tgaagactac agcgtcgcca gcgcagctct   2880
ctctagcgac ggccgcatct tcactggtgt caatgtatat cattttactg ggggaccttg   2940
tgcagaactc gtggtgctgg gcactgctgc tgctgcggca gctggcaacc tgacttgtat   3000
cgtcgcgatc ggaaatgaga acaggggcat cttgagcccc tgcggacggt gccgacaggt   3060
gcttctcgat ctgcatcctg ggatcaaagc catagtgaag gacagtgatg gacagccgac   3120
ggcagttggg attcgtgaat tgctgccctc tggttatgtg tgggagggct aagcacttcg   3180
tggccgagga gcaggactga cacgtgctac gagatttcga ttccaccgcc gccttctatg   3240
aaaggttggg cttcggaatc gttttccggg acgccggctg gatgatcctc cagcgcgggg   3300
atctcatgct ggagttcttc gcccacccca acttgtttat tgcagcttat aatggttaca   3360
aataaagcaa tagcatcaca aatttcacaa ataaagcatt tttttcactg cattctagtt   3420
gtggtttgtc caaactcatc aatgtatctt atcatgtctg tataccgtcg acctctagct   3480
agagcttggc gtaatcatgg tcatagctgt ttcctgtgtg aaattgttat ccgctcacaa   3540
ttccacacaa catacgagcc ggaagcataa agtgtaaagc ctggggtgcc taatgagtga   3600
gctaactcac attaattgcg ttgcgctcac tgcccgcttt ccagtcggga aacctgtcgt   3660
gccagctgca ttaatgaatc ggccaacgcg cggggagagg cggtttgcgt attgggcgct   3720
cttccgcttc ctcgctcact gactcgctgc gctcggtcgt tcggctgcgg cgagcggtat   3780
cagctcactc aaaggcggta atacggttat ccacagaatc aggggataac gcaggaaaga   3840
acatgtgagc aaaaggccag caaaaggcca ggaaccgtaa aaaggccgcg ttgctggcgt   3900
```

```
ttttccatag gctccgcccc cctgacgagc atcacaaaaa tcgacgctca agtcagaggt   3960
ggcgaaaccc gacaggacta taaagatacc aggcgtttcc ccctggaagc tccctcgtgc   4020
gctctcctgt tccgaccctg ccgcttaccg gatacctgtc cgcctttctc ccttcgggaa   4080
gcgtggcgct ttctcatagc tcacgctgta ggtatctcag ttcggtgtag gtcgttcgct   4140
ccaagctggg ctgtgtgcac gaaccccccg ttcagcccga ccgctgcgcc ttatccggta   4200
actatcgtct tgagtccaac ccggtaagac acgacttatc gccactggca gcagccactg   4260
gtaacaggat tagcagagcg aggtatgtag gcggtgctac agagttcttg aagtggtggc   4320
ctaactacgg ctacactaga agaacagtat ttggtatctg cgctctgctg aagccagtta   4380
ccttcggaaa aagagttggt agctcttgat ccggcaaaca aaccaccgct ggtagcggtg   4440
gtttttttgt ttgcaagcag cagattacgc gcagaaaaaa aggatctcaa gaagatcctt   4500
tgatcttttc tacggggtct gacgctcagt ggaacgaaaa ctcacgttaa gggattttgg   4560
tcatgagatt atcaaaaagg atcttcacct agatcctttt aaattaaaaa tgaagtttta   4620
aatcaatcta aagtatatat gagtaaactt ggtctgacag ttaccaatgc ttaatcagtg   4680
aggcacctat ctcagcgatc tgtctatttc gttcatccat agttgcctga ctccccgtcg   4740
tgtagataac tacgatacgg gagggcttac catctggccc cagtgctgca atgataccgc   4800
gagacccacg ctcaccggct ccagatttat cagcaataaa ccagccagcc ggaagggccg   4860
agcgcagaag tggtcctgca actttatccg cctccatcca gtctattaat tgttgccggg   4920
aagctagagt aagtagttcg ccagttaata gtttgcgcaa cgttgttgcc attgctacag   4980
gcatcgtggt gtcacgctcg tcgtttggta tggcttcatt cagctccggt tcccaacgat   5040
caaggcgagt tacatgatcc cccatgttgt gcaaaaaagc ggttagctcc ttcggtcctc   5100
cgatcgttgt cagaagtaag ttggccgcag tgttatcact catggttatg gcagcactgc   5160
ataattctct tactgtcatg ccatccgtaa gatgcttttc tgtgactggt gagtactcaa   5220
ccaagtcatt ctgagaatag tgtatgcggc gaccgagttg ctcttgcccg gcgtcaatac   5280
gggataatac cgcgccacat agcagaactt taaaagtgct catcattgga aaacgttctt   5340
cggggcgaaa actctcaagg atcttaccgc tgttgagatc cagttcgatg taacccactc   5400
gtgcacccaa ctgatcttca gcatctttta ctttcaccag cgtttctggg tgagcaaaaa   5460
caggaaggca aaatgccgca aaaaagggaa taagggcgac acggaaatgt tgaatactca   5520
tactcttcct ttttcaatat tattgaagca tttatcaggg ttattgtctc atgagcggat   5580
acatatttga atgtatttag aaaaataaac aaataggggt tccgcgcaca tttccccgaa   5640
aagtgccacc tgacgtc                                                  5657
```

<210> SEQ ID NO 275
<211> LENGTH: 5643
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 275

```
aacaaaatat taacgcttac aatttccatt cgccattcag gctgcgcaac tgttgggaag     60
ggcgatcggt gcgggcctct tcgctattac gccagctggc gaaaggggga tgtgctgcaa    120
ggcgattaag ttgggtaacg ccagggtttt cccagtcacg acgttgtaaa acgacggcca    180
gtgccaagct gatctataca ttgaatcaat attggcaatt agccatatta gtcattggtt    240
```

```
atatagcata aatcaatatt ggctattggc cattgcatac gttgtatcta tatcataata    300
tgtacattta tattggctca tgtccaatat gaccgccatg ttgacattga ttattgacta    360
gttattaata gtaatcaatt acggggtcat tagttcatag cccatatatg gagttccgcg    420
ttacataact tacggtaaat ggcccgcctg gctgaccgcc caacgacccc cgcccattga    480
cgtcaataat gacgtatgtt cccatagtaa cgccaatagg gactttccat tgacgtcaat    540
gggtggagta tttacggtaa actgcccact tggcagtaca tcaagtgtat catatgccaa    600
gtccgccccc tattgacgtc aatgacggta aatggcccgc ctggcattat gcccagtaca    660
tgaccttacg ggactttcct acttggcagt acatctacgt attagtcatc gctattacca    720
tggtgatgcg gttttggcag tacaccaatg ggcgtggata gcggtttgac tcacggggat    780
ttccaagtct ccaccccatt gacgtcaatg ggagtttgtt ttggcaccaa aatcaacggg    840
actttccaaa atgtcgtaat aaccccgccc cgttgacgca aatgggcggt aggcgtgtac    900
ggtgggaggt ctatataagc agagctcgtt tagtgaaccg tcagaatttt gtaatacgac    960
tcactatagg gcggccggga attcgtcgac tggatccggt accgaggaga tctgccgccg   1020
cgatcgccat ggaatacgcc tctgacgctt cactggaccc cgaagccccg tggcctcccg   1080
cgccccgcgc tcgcgcctgc cgcgtactgc cttgggccct ggtcgcgggg ctgctgctgc   1140
tgctgctgct cgctgccgcc tgcgccgtct tcctcgcctg cccctgggcc gtgtccgggg   1200
ctcgcgcctc gcccggctcc gcggccagcc cgagactccg cgagggtccc gagctttcgc   1260
ccgacgatcc cgccggcctc ttggacctgc ggcagggcat gtttgcgcag ctggtggccc   1320
aaaatgttct gctgatcgat gggcccctga gctggtacag tgacccaggc ctggcaggcg   1380
tgtccctgac gggggggcctg agctacaaag aggacacgaa ggagctggtg gtggccaagg   1440
ctggagtcta ctatgtcttc tttcaactag agctgcggcg cgtggtggcc ggcgagggct   1500
caggctccgt ttcacttgcg ctgcacctgc agccactgcg ctctgctgct ggggccgccg   1560
ccctggcttt gaccgtggac ctgccacccg cctcctccga ggctcggaac tcggccttcg   1620
gtttccaggg ccgcttgctg cacctgagtg ccggccagcg cctgggcgtc catcttcaca   1680
ctgaggccag ggcacgccat gcctggcagc ttacccaggg cgccacagtc ttgggactct   1740
tccgggtgac ccccgaaatc ccagccggac tcccttcacc gaggtcggaa acgcgtacgc   1800
ggccgctcga gcagaaactc atctcagaag aggatctggc agcaaatgat atcctggatt   1860
acaaggatga cgacgataag gtttaaacgg ccggccgcgg tcatagctgt ttcctgaaca   1920
gatcccgggt ggcatccctg tgacccctcc ccagtgcctc tcctggccct ggaagttgcc   1980
actccagtgc ccaccagcct tgtcctaata aaattaagtt gcatcatttt gtctgactag   2040
gtgtccttct ataatattat ggggtggagg ggggtggtat ggagcaaggg gcaagttggg   2100
aagacaacct gtagggcctg cggggtctat tgggaaccaa gctggagtgc agtggcacaa   2160
tcttggctca ctgcaatctc cgcctcctgg gttcaagcga ttctcctgcc tcagcctccc   2220
gagttgttgg gattccaggc atgcatgacc aggctcagct aatttttgtt tttttggtag   2280
agacggggtt tcaccatatt ggccaggctg gtctccaact cctaatctca ggtgatctac   2340
ccaccttggc ctcccaaatt gctgggatta caggcgtgaa ccactgctcc cttccctgtc   2400
cttctgattt taaaataact ataccagcag gaggacgtcc agacacagca taggctacct   2460
ggccatgccc aaccggtggg acatttgagt tgcttgcttg gcactgtcct ctcatgcgtt   2520
gggtccactc agtagatgcc tgttgaattg ggtacgcggc cagcggcgag cggtatcagc   2580
```

-continued

```
tcactcaaag gcggtaatac ggttatccac agaatcaggg gataacgcag gaaagaacat   2640
gtgagcaaaa ggccagcaaa aggccaggaa ccgtaaaaag gccgcgttgc tggcgttttt   2700
ccataggctc cgcccccctg acgagcatca caaaaatcga cgctcaagtc agaggtggcg   2760
aaacccgaca ggactataaa gataccaggc gtttccccct ggaagctccc tcgtgcgctc   2820
tcctgttccg accctgccgc ttaccggata cctgtccgcc tttctccctt cgggaagcgt   2880
ggcgctttct catagctcac gctgtaggta tctcagttcg gtgtaggtcg ttcgctccaa   2940
gctgggctgt gtgcacgaac cccccgttca gcccgaccgc tgcgccttat ccggtaacta   3000
tcgtcttgag tccaacccgg taagacacga cttatcgcca ctggcagcag ccactggtaa   3060
caggattagc agagcgaggt atgtaggcgg tgctacagag ttcttgaagt ggtggcctaa   3120
ctacggctac actagaagaa cagtatttgg tatctgcgct ctgctgaagc cagttacctt   3180
cggaaaaaga gttggtagct cttgatccgg caaacaaacc accgctggta gcggtggttt   3240
ttttgtttgc aagcagcaga ttacgcgcag aaaaaaagga tctcaagaag atcctttgat   3300
cttttctacg gggtctgacg ctcagtggaa cgaaaactca cgttaaggga ttttggtcat   3360
gagattatca aaaaggatct tcacctagat ccttttaaat taaaaatgaa gttttaaatc   3420
aatctaaagt atatatgagt aacctgaggc tatggcaggg cctgccgccc cgacgttggc   3480
tgcgagccct gggccttcac ccgaacttgg ggggtggggt ggggaaaagg aagaaacgcg   3540
ggcgtattgg ccccaatggg gtctcggtgg ggtatcgaca gagtgccagc cctgggaccg   3600
aaccccgcgt ttatgaacaa acgacccaac accgtgcgtt ttattctgtc tttttattgc   3660
cgtcatagcg cgggttcctt ccggtattgt ctccttccgt gtttcagtta gcctcccccct   3720
agggtgggcg aagaactcca gcatgagatc cccgcgctgg aggatcatcc agccggcgtc   3780
ccggaaaacg attccgaagc ccaacctttc atagaaggcg gcggtggaat cgaaatctcg   3840
tgatggcagg ttgggcgtcg cttggtcggt catttcgaac cccagagtcc cgctcagaag   3900
aactcgtcaa gaaggcgata gaaggcgatg cgctgcgaat cgggagcggc gataccgtaa   3960
agcacgagga agcggtcagc ccattcgccg ccaagctctt cagcaatatc acgggtagcc   4020
aacgctatgt cctgatagcg atccgccaca cccagccggc cacagtcgat gaatccagaa   4080
aagcggccat tttccaccat gatattcggc aagcaggcat cgccatgggt cacgacgaga   4140
tcctcgccgt cgggcatgct cgccttgagc ctggcgaaca gttcggctgg cgcgagcccc   4200
tgatgctctt cgtccagatc atcctgatcg acaagaccgg cttccatccg agtacgtgct   4260
cgctcgatgc gatgtttcgc ttggtggtcg aatgggcagg tagccggatc aagcgtatgc   4320
agccgccgca ttgcatcagc catgatggat actttctcgg caggagcaag gtgagatgac   4380
aggagatcct gccccggcac ttcgcccaat agcagccagt cccttcccgc ttcagtgaca   4440
acgtcgagca cagctgcgca aggaacgccc gtcgtggcca gccacgatag ccgcgctgcc   4500
tcgtcttgca gttcattcag ggcaccggac aggtcggtct tgacaaaaag aaccgggcgc   4560
ccctgcgctg acagccggaa cacggcggca tcagagcagc cgattgtctg ttgtgcccag   4620
tcatagccga atagcctctc cacccaagcg gccggagaac ctgcgtgcaa tccatcttgt   4680
tcaatcatgc gaaacgatcc tcatcctgtc tcttgatcga tctttgcaaa agcctaggcc   4740
tccaaaaaag cctcctcact acttctggaa tagctcagag gccgaggcgg cctcggcctc   4800
tgcataaata aaaaaaatta gtcagccatg gggcggagaa tgggcggaac tgggcggagt   4860
taggggcggg atgggcggag ttaggggcgg gactatggtt gctgactaat tgagatgcat   4920
gctttgcata cttctgcctg ctggggagcc tggggacttt ccacacctgg ttgctgacta   4980
```

-continued

```
attgagatgc atgctttgca tacttctgcc tgctggggag cctggggact ttccacaccc   5040

taactgacac acattccaca gctggttctt tccgcctcag gactcttcct tttcaatat    5100

tattgaagca tttatcaggg ttattgtctc atgagcggat acatatttga atgtatttag   5160

aaaaataaac aaataggggt tccgcgcaca tttccccgaa aagtgccacc tgacgcgccc   5220

tgtagcggcg cattaagcgc ggcgggtgtg gtggttacgc gcagcgtgac cgctacactt   5280

gccagcgccc tagcgcccgc tcctttcgct ttcttccctt cctttctcgc cacgttcgcc   5340

ggctttcccc gtcaagctct aaatcggggg ctccctttag ggttccgatt tagtgcttta   5400

cggcacctcg accccaaaaa acttgattag ggtgatggtt cacgtagtgg gccatcgccc   5460

tgatagacgg tttttcgccc tttgacgttg gagtccacgt tctttaatag tggactcttg   5520

ttccaaactg gaacaacact caaccctatc tcggtctatt cttttgattt ataagggatt   5580

ttgccgattt cggcctattg gttaaaaaat gagctgattt aacaaaaatt taacgcgaat   5640

ttt                                                                 5643
```